US012599634B2

(12) United States Patent
Le et al.

(10) Patent No.: US 12,599,634 B2
(45) Date of Patent: Apr. 14, 2026

(54) NERVE GUIDANCE CONDUIT COMPRISING NEURAL CREST STEM-LIKE CELLS AND/OR SCHWANN CELL PRECURSOR-LIKE CELLS AND METHODS OF MAKING AND USING THE SAME

(71) Applicant: THE TRUSTEES OF THE UNIVERSITY OF PENNSYLVANIA, Philadelphia, PA (US)

(72) Inventors: Anh D. Le, Philadelphia, PA (US); Qunzhou Zhang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 717 days.

(21) Appl. No.: 17/950,446

(22) Filed: Sep. 22, 2022

(65) Prior Publication Data

US 2023/0086560 A1 Mar. 23, 2023

Related U.S. Application Data

(60) Provisional application No. 63/247,509, filed on Sep. 23, 2021.

(51) Int. Cl.
| | |
|---|---|
| *C12N 5/0797* | (2010.01) |
| *A61K 35/30* | (2015.01) |
| *A61K 38/18* | (2006.01) |
| *A61K 47/46* | (2006.01) |
| *A61P 25/02* | (2006.01) |
| *C12N 5/079* | (2010.01) |

(52) U.S. Cl.
CPC ............ *A61K 35/30* (2013.01); *A61K 38/185* (2013.01); *A61K 47/46* (2013.01); *A61P 25/02* (2018.01); *C12N 5/0622* (2013.01); *C12N 5/0623* (2013.01); *C12N 2506/1361* (2013.01); *C12N 2513/00* (2013.01); *C12N 2533/54* (2013.01); *C12N 2533/90* (2013.01)

(58) Field of Classification Search
None
See application file for complete search history.

(56) References Cited

U.S. PATENT DOCUMENTS

2020/0397947 A1* 12/2020 Syed-Picard ......... A61L 27/383

OTHER PUBLICATIONS

Zhang, Qunzhou; et al; "Neural Crest Stem-Like Cells Non-genetically Induced from Human Gingiva-Derived Mesenchymal Stem Cells Promote Facial Nerve Regeneration in Rats" Molecular Neurobiology, 55, 6965-6983, 2018 (Year: 2018).*

Caliari, et al., "Dimensionality and spreading influence MSC YAP/TAZ signaling in hydrogel environments", Biomaterials, Oct. 2016; 103:314-323. doi: 10.1016/j.biomaterials.2016.06.061. Epub Jun. 29, 2016. PMID: 27429252; PMCID: PMC4963302.

Long, et al., "A biomaterial approach to cell reprogramming and differentiation", J Mater Chem B, Apr. 7, 2017; 5 (13):2375-2379. doi: 10.1039/C6TB03130G. Epub Feb. 20, 2017. PMID: 28966790; PMCID: PMC5616208.

Sun, et al., "Conduits Harnessing Spatially Controlled Cell-Secreted Neurotrophic Factors Improve Peripheral Nerve Regeneration", Biomaterials, May 2019; 203:86-95. doi: 10.1016/j.biomaterials. 2019.01.038. Epub Feb. 19, 2019. PMID: 30857644.

Zhang, et al., "3D bio-printed scaffold-free nerve constructs with human gingivaderived mesenchymal stem cells promote rat facial nerve regeneration", Sci Rep., Apr. 26, 2018; 8(1):6634. doi: 10.1038/s41598-018-24888-w. PMID: 29700345; PMCID: PMC5919929.

Zhang, et al., "Harnessing 3D collagen hydrogel-directed conversion of human GMSCs into SCP-like cells to generate functionalized nerve conduits", NPJ Regen Med., Sep. 30, 2021;6(1):59. doi: 10.1038/s41536-021-00170-y. PMID: 34593823; PMCID: PMC8484485.

* cited by examiner

*Primary Examiner* — David W Berke-Schlessel
(74) *Attorney, Agent, or Firm* — Saul Ewing LLP; Kathryn Doyle; Justin Crotty

(57) ABSTRACT

The present invention includes a functionalized nerve guidance conduit (NGC), methods of making neurotrophic factor-expressing neural crest stem-like cells (NCSC) and/or Schwann cell precursor-like (SCP) cells, methods of making the functionalized nerve guidance conduit, and methods of treating nerve injury using the functionalized nerve guidance conduit.

10 Claims, 26 Drawing Sheets

FIG.23A                                                    FIG.23C

FIG.24B    S-100β          FIG.24C          β-tubulin III

NERVE GUIDANCE CONDUIT COMPRISING NEURAL CREST STEM-LIKE CELLS AND/OR SCHWANN CELL PRECURSOR-LIKE CELLS AND METHODS OF MAKING AND USING THE SAME

CROSS-REFERENCE TO RELATED APPLICATION

This application claims priority under 35 U.S.C. § 119(e) to U.S. Provisional Patent Application No. 63/247,509, filed Sep. 23, 2021, the disclosures of which is incorporated herein by reference in its entirety.

BACKGROUND OF THE INVENTION

Twenty million Americans suffer from peripheral nerve injuries (PNIs) caused by either trauma or medical disorders with the majority resulting from trauma. The gold standard for trauma-PNI repair is a nerve autograft wherein a healthy nerve is surgically removed from an unaffected site of the patient and implanted at the site of the nerve trauma. Major drawbacks are associated with this approach, such as severe donor-site morbidity and limited donor nerve source. A need exists for improved treatment for PNIs. The present invention addresses this need.

SUMMARY OF THE INVENTION

In one aspect, the invention provides a functionalized nerve guidance conduit (NGC) comprising: a wall matrix comprising a decellularized extracellular matrix; and neurotrophic factor-expressing neural crest stem-like cells (NCSC) and/or Schwann cell precursor-like (SCP) cells embedded in the wall matrix.

In another aspect, the invention provides a method of making neurotrophic factor-expressing neural crest stem-like cells (NCSC) and/or Schwann cell precursor-like (SCP) cells, the method comprising: providing gingiva-derived mesenchymal stem cells (GMSCs); and culturing the GMSCs in a 3D-collagen hydrogel, thereby making neurotrophic factor-expressing NCSC and/or SCP cells.

In yet another aspect, the invention provides a method of making a functionalized nerve guidance conduit (NGC), the method comprising: providing gingiva-derived mesenchymal stem cells (GMSCs); culturing the GMSCs in a 3D-collagen hydrogel, thereby making neurotrophic factor-expressing neural crest stem-like cells (NCSC) and/or Schwann cell precursor-like (SCP) cells; filling a nerve guidance conduit with the neurotrophic factor-expressing NCSC and/or SCP cells; and culturing the nerve guidance conduit in vitro, thereby forming a functionalized nerve guidance conduit.

In yet another aspect, the invention provides a method of treating a nerve injury in a subject in need thereof, the method comprising implanting the functionalized nerve guidance conduit according to claim 1 at a site of nerve injury in the subject, thereby treating the nerve injury.

In various embodiments, the neurotrophic factor-expressing NCSC and/or SCP cells are generated from gingiva-derived mesenchymal stem cells (GMSCs).

In various embodiments, the neurotrophic factor-expressing NCSC and/or SCP cells express at least one neurotrophic factor selected from glial cell-derived neurotrophic factor (GDNF) and brain-derived neurotrophic factor (BDNF).

In various embodiments, the neurotrophic factor-expressing NCSC and/or SCP cells further express at least one marker selected from the group consisting of Low Affinity Nerve Growth Factor Receptor (NGFR), SRY-Box Transcription Factor 9 (Sox9), ERBB Receptor Feedback Inhibitor I (ERRFI1), Neurotrophin 3 (Ntf3), Twist Family BHLH Transcription Factor 1 (Twist 1), S-100β, SRY-Box Transcription Factor 10 (Sox10), p75NTR, and Glial Fibrillary Acidic Protein (GFAP).

In various embodiments, the neurotrophic factor-expressing NCSC and/or SCP cells further express at least one NOTCH signaling pathway marker selected from the group consisting of DLL1, DLL4, JAG2, Notch3, Hes1, and Hey1.

In various embodiments, the neurotrophic factor-expressing NCSC and/or SCP cells are generated from GMSCs by culturing the GMSCs in a 3D-collagen hydrogel.

In various embodiments, the 3D-collagen hydrogel comprises about 3-5 mg/mL collagen in mesenchymal stem cell culture medium.

In various embodiments, the 3D-collagen hydrogel comprises about 4 mg/mL collagen in mesenchymal stem cell culture medium.

In various embodiments, the mesenchymal stem cell culture medium comprises alpha-Minimum Essential Medium (α-MEM) and Fetal Bovine Serum (FBS).

In various embodiments, the 3D-collagen hydrogel is methacrylated.

In various embodiments, the decellularized extracellular matrix comprises a porcine small intestine submucosal extracellular matrix (SIS-ECM).

In various embodiments, the nerve injury is a peripheral nerve injury.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A, GMSCs ($2 \times 10^6$/mL) were encapsulated in 3D-collagen hydrogel at different concentrations (2, 3, 4, 6 mg/mL) and cultured in complete α-minimum essential medium (α-MEM) for 48 h. FIG. 1B, The expression levels of Ngfr (p75), Sox9, Errfi1, Gdnf, and Ntf3 in GMSCs cultured in 3D collagen hydrogel were determined by qRT-PCR as compared to those in 2D-cultured GMSCs (2D-con). FIG. 1C, Immunofluorescence (IF) staining against p75 and SOX9 in cryosections of 3D-collagen hydrogel encapsulated with GMSCs. Nuclei were counterstained with 4', 6-diamidino-2-phenylindole (DAPI). Scale bar=20 μm (c). FIG. 1D, Quantification of IF intensity of p75 and SOX9. Data represented the mean±SD, n=3 biological replicates. *p<0.05; p<0.01; *p<0.001; ns, no significant; one-way ANOVA with the Tukey's post test (FIGS. 1B and 1D). 2D-con, GMSCs cultured in 2D-conditions; 3D, GMSCs cultured in 3D-collagen hydrogel with different concentrations.

FIG. 2A, Immunofluorescence staining against p75$^{NTR}$, and counterstaining of cell nuclei with 4', 6-diamidino-2-phenylindole (DAPI). Scale bar=20 μm. FIG. 2B, Quantification of Immunofluorescence (IF) intensity of p75. FIG. 2C, GMSCs were harvested from 2D-culture or recovered from 3D collagen hydrogel via digestion with collagenase I followed by immunofluorescence staining for p75$^{NTR}$, followed by incubation with Alexa Fluor 488-conjugated secondary antibodies. The cell samples were analyzed by a flow cytometer (FCM). FIG. 2D, The average of p75+ cells from FCM analysis. FIG. 2E, GMSCs encapsulated 3D collagen hydrogel were cultured for different time periods and the expression of p75$^{NTR}$ protein was determined by Western blot (WB). FIG. 2F, Quantification of the relative WB density of p75$^{NTR}$ with GAPDH as the internal control. Data represent the mean±SD, n=3 biological replicates. *p<0.05; p<0.01; *p<0.001; ns, no significant; Student's two-tailed unpaired t-test (FIG. 2B, FIG. 2D, FIG. 2F). 2D, GMSCs cultured in 2D-conditions; 3D, GMSC cultured in 3D-collagen hydrogel.

FIG. 3A, Heatmap illustrates NCSC/SCP-like cell-related genes that are significantly upregulated across all samples of GMSCs cultured in 3D collagen hydrogel as compared to the paired 2D-cultured GMSCs (triplicates in 2-pairs of GMSCs). The high expression and low expressions are represented. logFC, log 2 (fold change; 3D-cultured GMSCs over those 2D-cultured). FIG. 3B, The upregulation of several NCSC-related genes in GMSCs cultured in 3D-collagen hydrogel was confirmed by quantitative RT-PCR as compared to those in 2D-cultured GMSCs as controls (2Dcon). Data represent the mean±SD, n=3 biological replicates. *p<0.05; p<0.01; *p<0.001. Student's two-tailed unpaired t-test (FIG. 3B). 2D or 2D-con, GMSCs cultured in 2D-conditions; 3D, GMSC cultured in 3D-collagen hydrogel.

FIG. 4A, GMSCs were encapsulated in 3D-collagen hydrogel (4 mg/mL) at a cell density of 2×10$^6$/mL and cultured in complete α-MEM for 48 h. The mRNA expression of mesenchymal cell-associated genes, Cd90 (Thy1), Cd73, Col-I, Vcl, and β-actin, in 3D-cultured GMSCs was determined by quantitative RT-PCR as compared to those in 2D-cultured GMSCs. FIG. 4B, GMSCs were cultured under 2D culture or in 3D-collagen hydrogel for 48 h. Immunofluorescence (IF) staining for vinculin while the cytoskeleton (F-actin) was stained with tetramethylrhodamine (TRITC)-conjugated phalloidin, a high-affinity F-actin probe. Nuclei were counterstained with 4', 6-diamidino-2-phenylindole (DAPI). Scale bar=20 μm. FIG. 4C, Quantification of IF intensity of vinculin (VCL) and F-actin. FIG. 4D, GMSCs were harvested from 2D culture or recovered from 3D collagen hydrogel via digestion with collagenase I and then immunostained with specific antibodies for CD90 (THY1), followed by incubation with Alexa Fluor 488-conjugated secondary antibodies. The cell samples were analyzed by a flow cytometer (FCM). FIG. 4E, The average of CD90+ cells from FCM analysis. Data represent the mean±SD, n=3 biological replicates. *p<0.05; p<0.01; *p<0.001. Student's two-tailed unpaired t-test (FIGS. 4A,

4C, 4E). Col-I, type I collagen; Vcl, vinculin; 2D or 2D-con, GMSCs cultured in 2D-conditions; 3D, GMSC cultured in 3D-collagen hydrogel.

Figures 5A, 5B:
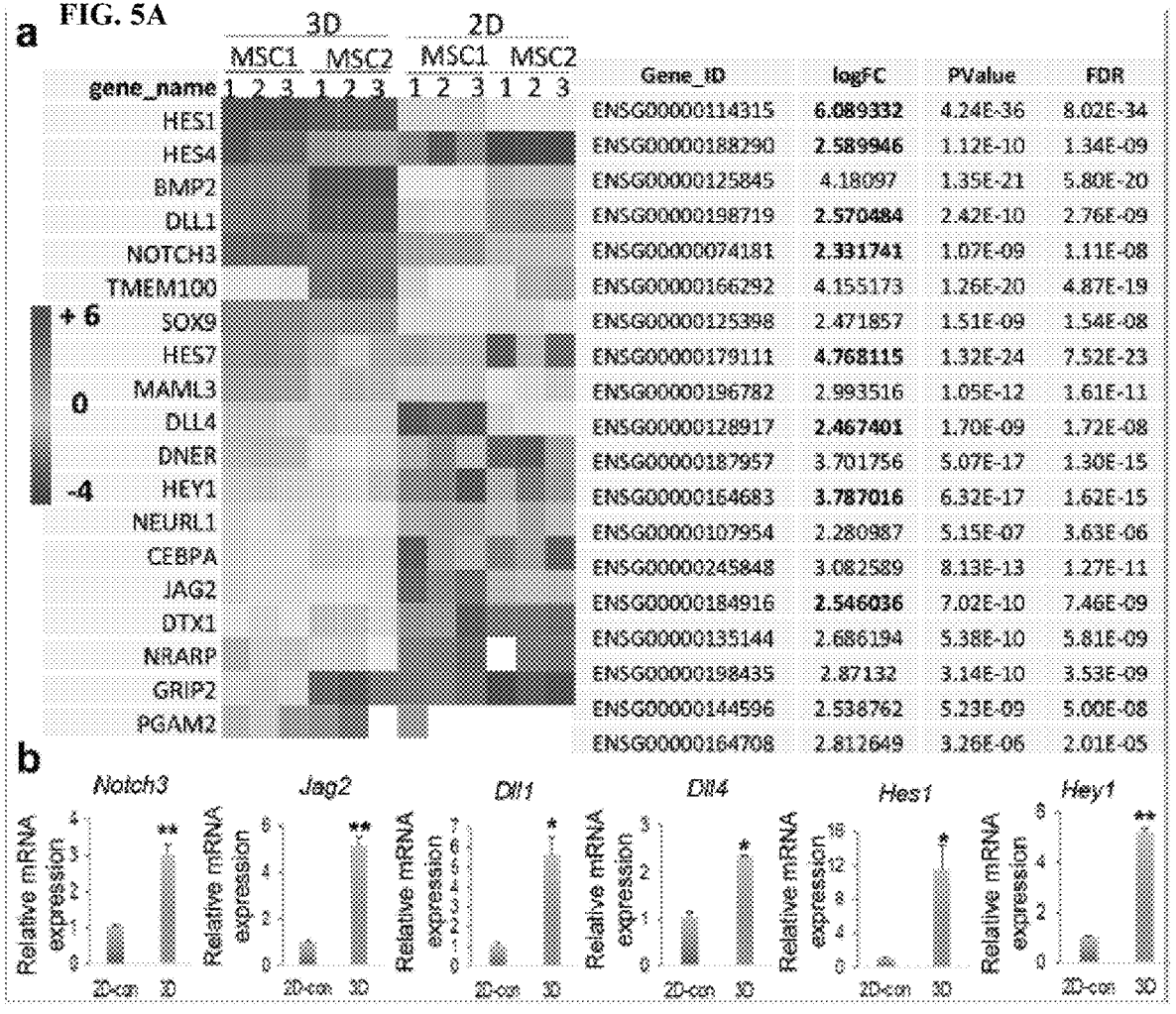

FIGS. 5A-5B show upregulated mRNA expression of a cluster of Notch signaling-related genes in GMSCs cultured in methacrylated 3D-collagen hydrogel. GMSCs were encapsulated in 3D-collagen hydrogel (4 mg/mL) at a cell density of 2×10$^6$/mL and cultured in complete α-MEM for 48 h. Total RNA was extracted from 2D- and 3D-cultured GMSCs for RNA-seq or qRT-PCR. FIG. 5A, Heatmap illustrates genes related to Notch signaling pathway that are significantly upregulated across all samples of GMSCs cultured in 3D collagen hydrogel as compared to the paired 2D-cultured GMSCs (triplicates in 2-pairs of GMSCs). The high expression and low expression are shown. logFC, log 2 (fold change; 3D-cultured GMSCs over those 2D-cultured). FIG. 5B, The upregulation of several Notch signaling genes in GMSCs cultured in 3D-collagen hydrogel was confirmed by quantitative RT-PCR as compared to those in 2D-cultured GMSCs. Data represent the mean±SD, n=3 biological replicates. *p<0.05; p<0.01. Student's two-tailed unpaired t-test (FIG. 5B**). 2D or 2D-con, GMSCs cultured in 2D-conditions; 3D, GMSC cultured in 3D-collagen hydrogel.

Figures 6A, 6B, 6C:
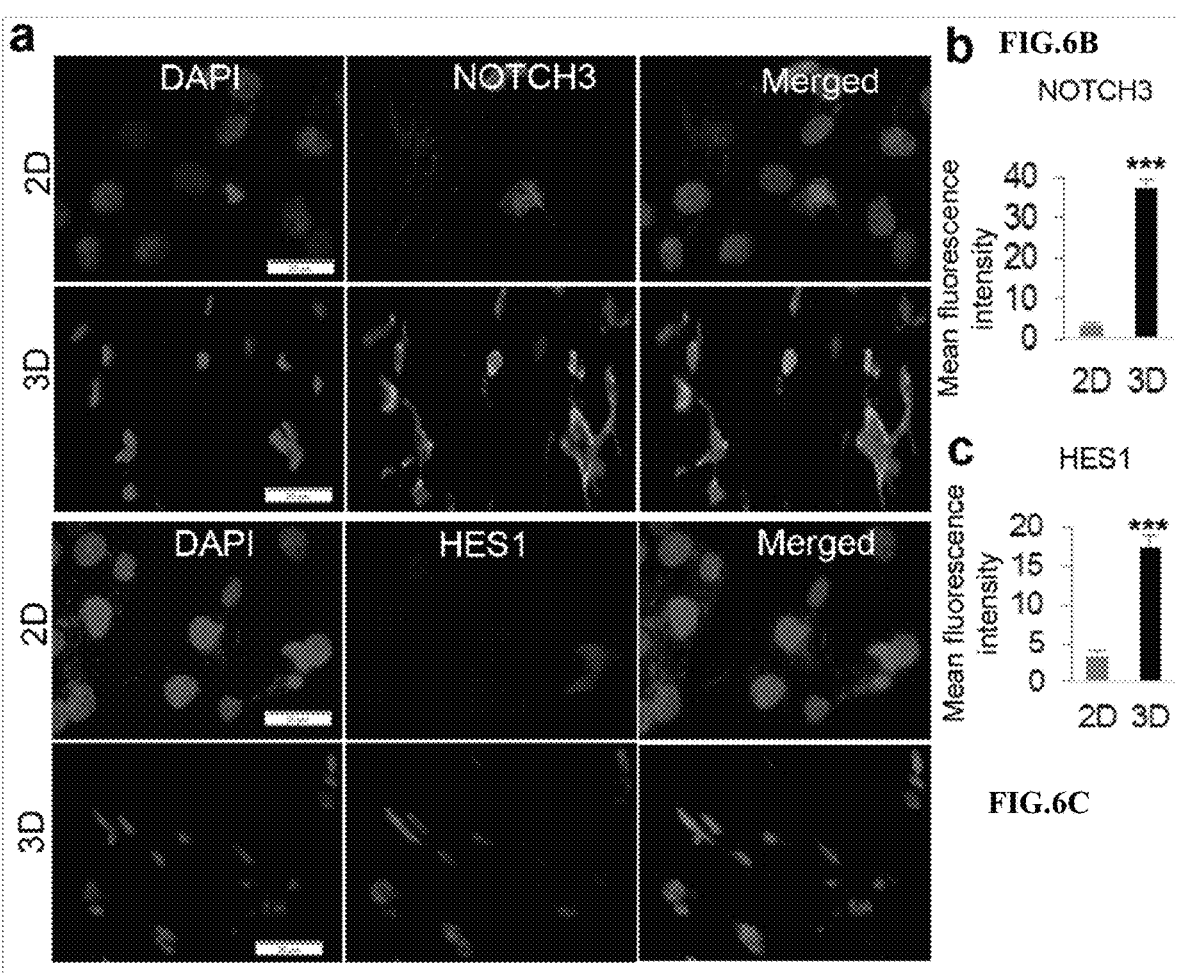
Figures 6D, 6E, 6F, 6G, 6H:
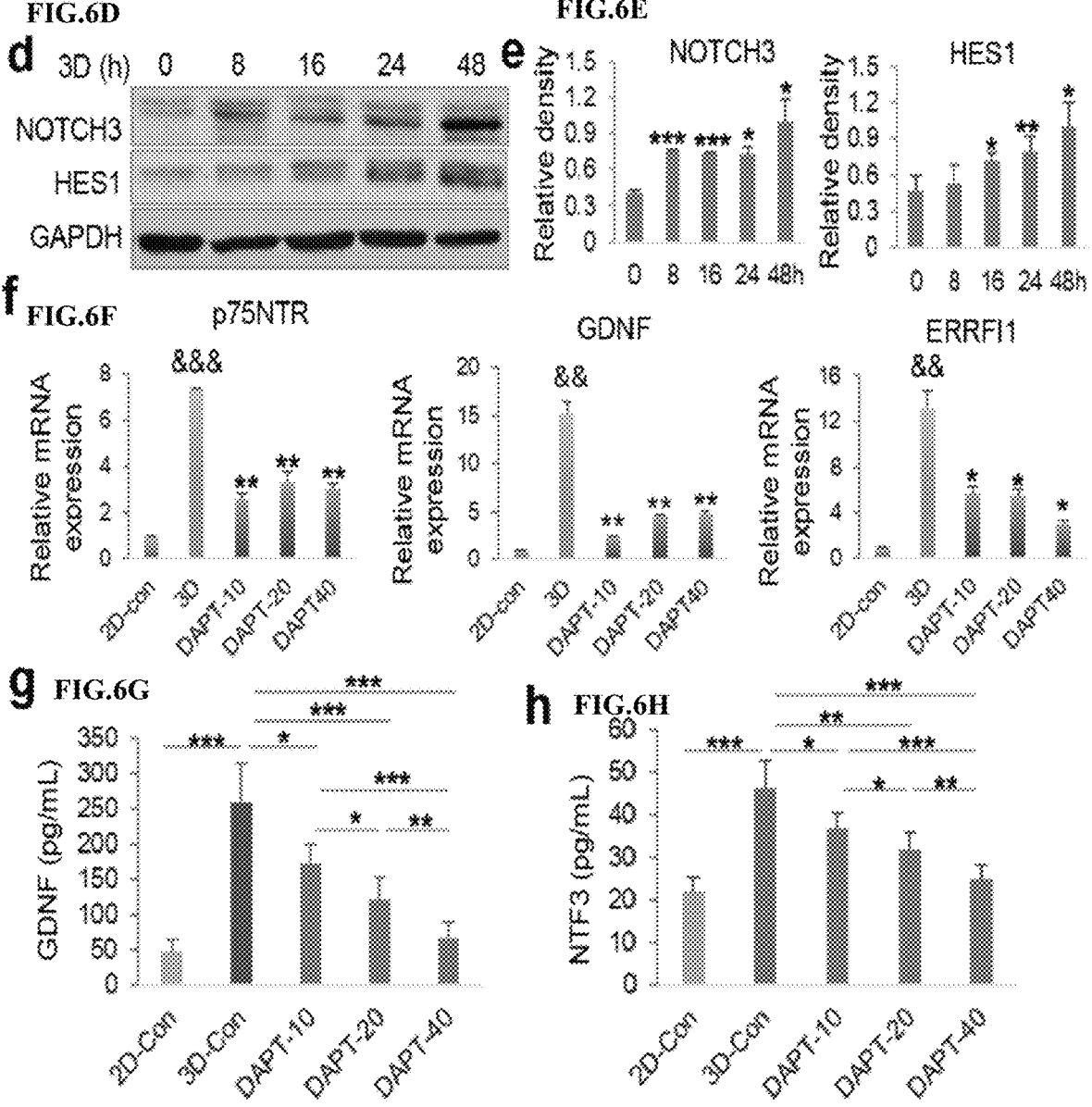

FIGS. 6A-6H show that blocking NOTCH signaling activation attenuated 3D collagen hydrogel-mediated upregulation of NCSC/SCP-related genes in GMSCs. GMSCs were encapsulated in 3D-collagen hydrogel (4 mg/mL) at a cell density of 2×10$^6$/mL and cultured in complete α-MEM for 48 h. FIG. 6A, Immunofluorescence (IF) staining for NOTCH3 and HES-1. Nuclei were counterstained with 4', 6-diamidino-2-phenylindole (DAPI). Scale bar=20 μm. FIG. 6B and FIG. 6C, Quantification of IF intensity of NOTCH3 (FIG. 6B) and HES1 (FIG. 6C). FIG. 6D, GMSCs encapsulated 3D collagen hydrogel were cultured for different time periods and the expression of NOTCH3 and HES1 proteins was determined by Western blot (WB). FIG. 6E, Quantification of the relative WB densities of NOTCH3 and HES1 with GAPDH as the internal control. FIGS. 6F-6H, GMSCs encapsulated in 3D-collagen hydrogel (4 mg/mL) at a cell density of 2×10$^6$/mL were cultured in complete α-MEM in the presence of different concentrations of DAPT (10, 20, 40 μmol/L), a specific inhibitor of NOTCH activity, for 48 h. The mRNA expression of p75$^{NTR}$, Gdnf, and Errfi1 genes in 3D-cultured GMSCs was determined by qRT-PCR as compared to those in 2D-cultured GMSCs (FIG. 6F). *p<0.05; p<0.01 (DAPT versus 3D control); &&p<0.01, &&&p<0.001 (3D versus 2D control). The secretion of GDNF (FIG. 6G) and NTF3 (FIG. 6H**) in the supernatants was determined by ELISA. *p<0.05; p<0.01; *p<0.001. Data represent the mean±SD, n=3 biological replicates. Student's two-tailed unpaired t-test (FIGS. 6B, 6C, 6E). One-way ANOVA with the Tukey's post test (FIGS. 6F, 6G, 6H). 2D or 2D-con, GMSCs cultured in 2D-conditions; 3D or 3D-Con, GMSC cultured in 3D-collagen hydrogel.

Figures 7A, 7B, 7C, 7D:
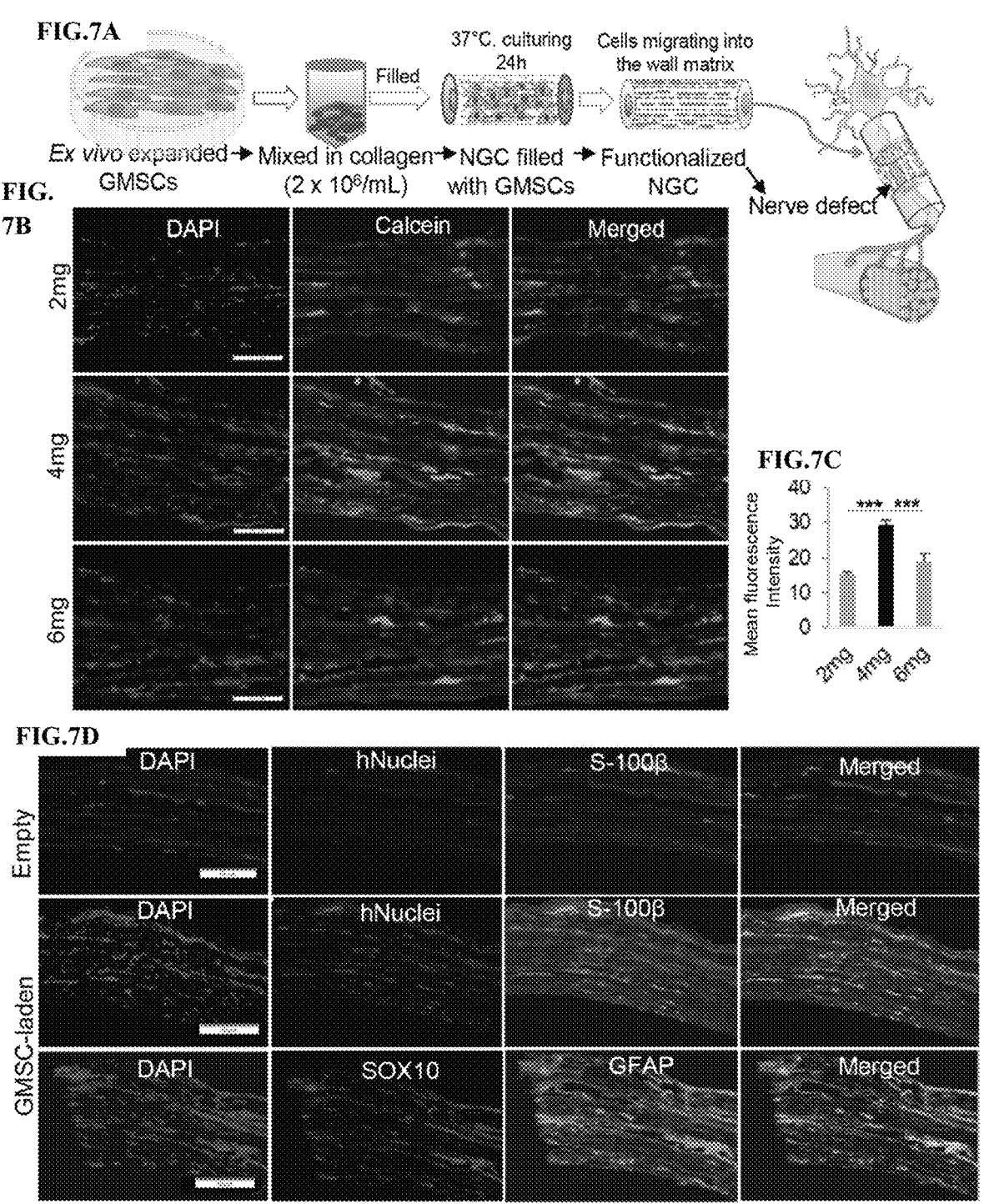

FIGS. 7A-7D show generation of functionalized NGCs by harnessing 3D collagen hydrogel-directed conversion of GMSCs into NCSC/SCP-like cells. FIG. 7A, GMSCs were encapsulated in 40 μl of 3D-collagen hydrogel at different concentrations (2, 4, 6 mg/mL) and a cell density of 2×10$^6$/mL and then filled into AxoGuard Nerve protector or connector (NGC) (10 mm in length and 2 mm in inner diameter). Then, the constructs (NGC containing 3D collagen hydrogel encapsulated with GMSCs) were cultured for 24 h in complete α-MEM. FIG. 7B, Before harvesting, the NGC constructs were labeled with 10 μM calcein-AM at 37° C.

for 30 min. Cryosections were cut and the migrated cells labeled with calcein-AM (green color) in the wall matrix were observed under a fluorescence microscope. Nuclei were counterstained with 4', 6-diamidino-2-phenylindole (DAPI). FIG. 7C, Quantification of IF intensity of calcein-AM. FIG. 7D, Cryosections of NGCs containing cell-free collagen hydrogel (Empty) or GMSC-laden collagen hydrogel at a concentration of 4 mg/mL (Cell-laden) were prepared for dual color immunostaining for human nuclei (hNuclei), SOX10, S-100β or GFAP. Nuclei were counterstained with 4', 6-diamidino-2-phenylindole (DAPI). Scale bar=50 μm (FIGS. 7B, 7D). *p<0.0001. Data represent the mean±SD, n=3 biological replicates. One-way ANOVA with the Tukey's post test (FIG. 7C**). NGC, nerve guidance conduit.

Figures 8A, 8B, 8C, 8D, 8E, 8F, 8G, 8H:
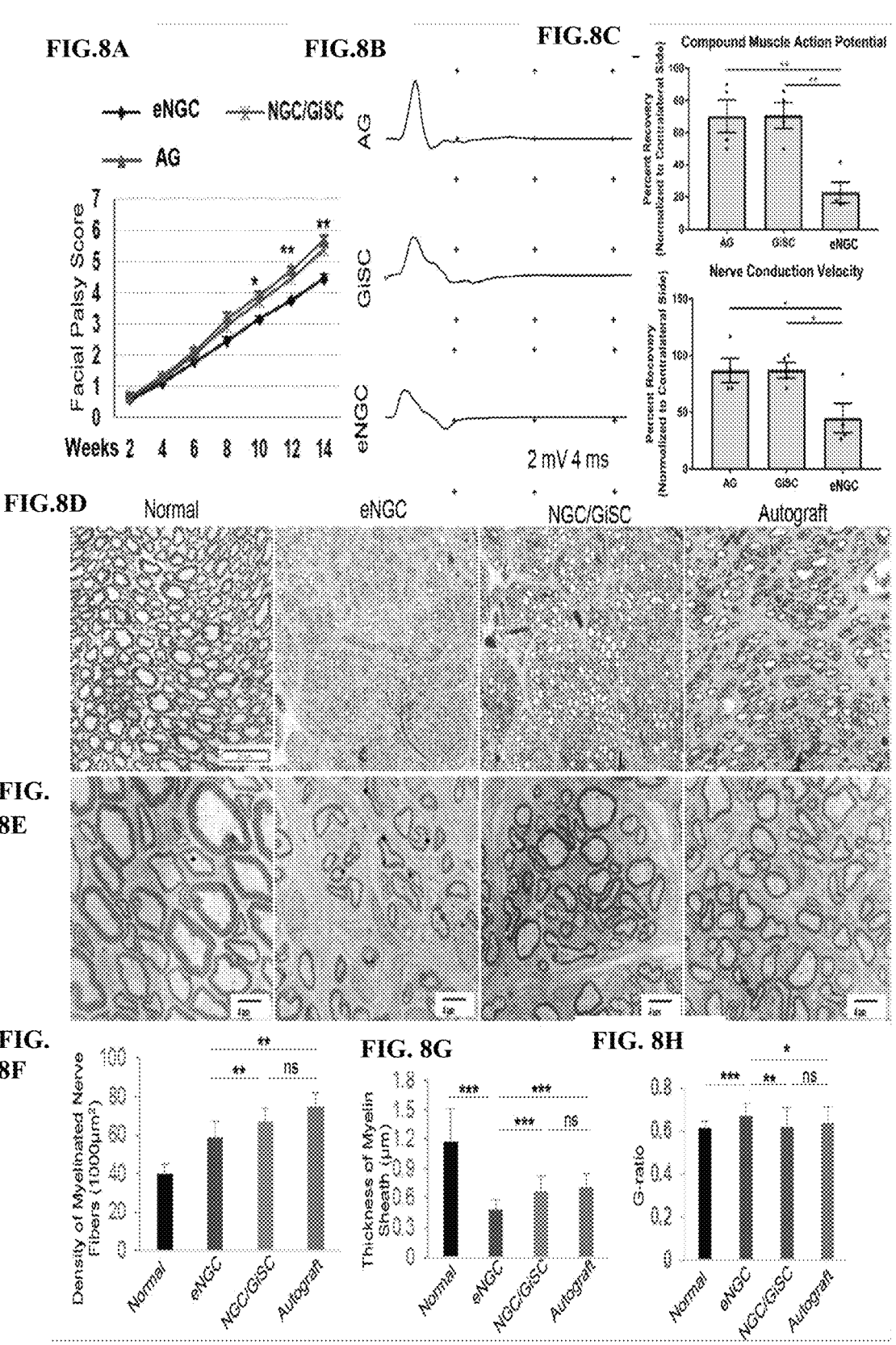

FIGS. 8A-8H show implantation of NGC/GiSCs promotes functional recovery and axonal regeneration of transected rat facial nerves. FIG. 8A, Longitudinal evaluation of facial palsy score in rats following implantation of empty nerve conduits (eNGC), nerve autograft (AG), or nerve conduits (NGC) laden with GiSCs for up to 14 weeks. Data represent the mean±SD (n=6 rats). *p<0.05, p<0.01 (NGC/GiSC vs eNGC). Student's two-tailed unpaired t-test (FIG. 8A). FIG. 8B and FIG. 8C**, Compound muscle action potential (CMAP) recordings of the vibrisal muscles of both the injury side and the contralateral normal side of rats following both proximal and distal stimulation. Motor nerve conduction velocity of both the injury side and the contralateral normal side of rats was calculated as described in Materials & Methods. Data represent the mean±SD (n=4 rats). *p<0.05, p<0.01. One-way ANOVA with the Tukey's post test (FIG. 8C). FIG. 8D, Toluidine blue staining of semi-thin sections of the newly regenerated facial nerves from different groups of rats at 14 weeks post-injury and implantation. Scale bar=20 μm. FIG. 8E, Transmission electron microscopy (TEM) of ultrathin sections of the newly regenerated facial nerves from different groups of rats at 14 weeks post-injury and implantation. Scale bars, 4 μm. FIG. 8F, Quantification of density of myelinated axons (the number of myelinated axons/1000 μm²). FIG. 8G, Quantification of the thickness of the myelin sheaths. FIG. 8H**, Calculation of the G-ratios (the inner axonal diameter/the outer myelinated fiber diameter). Data represent the mean±SD (n=3 rats). *p<0.05, p<0.01, *p<0.001; ns, no significance. One-way ANOVA with the Tukey's post test (FIGS. 8F, 8G, 8H). AG, autograft; eNGC, empty nerve conduit; NGC, nerve conduit; GiSC, GMSC-derived NCSC/SCP-like cells.

Figures 9A, 9B, 9C, 9D, 9E, 9F:
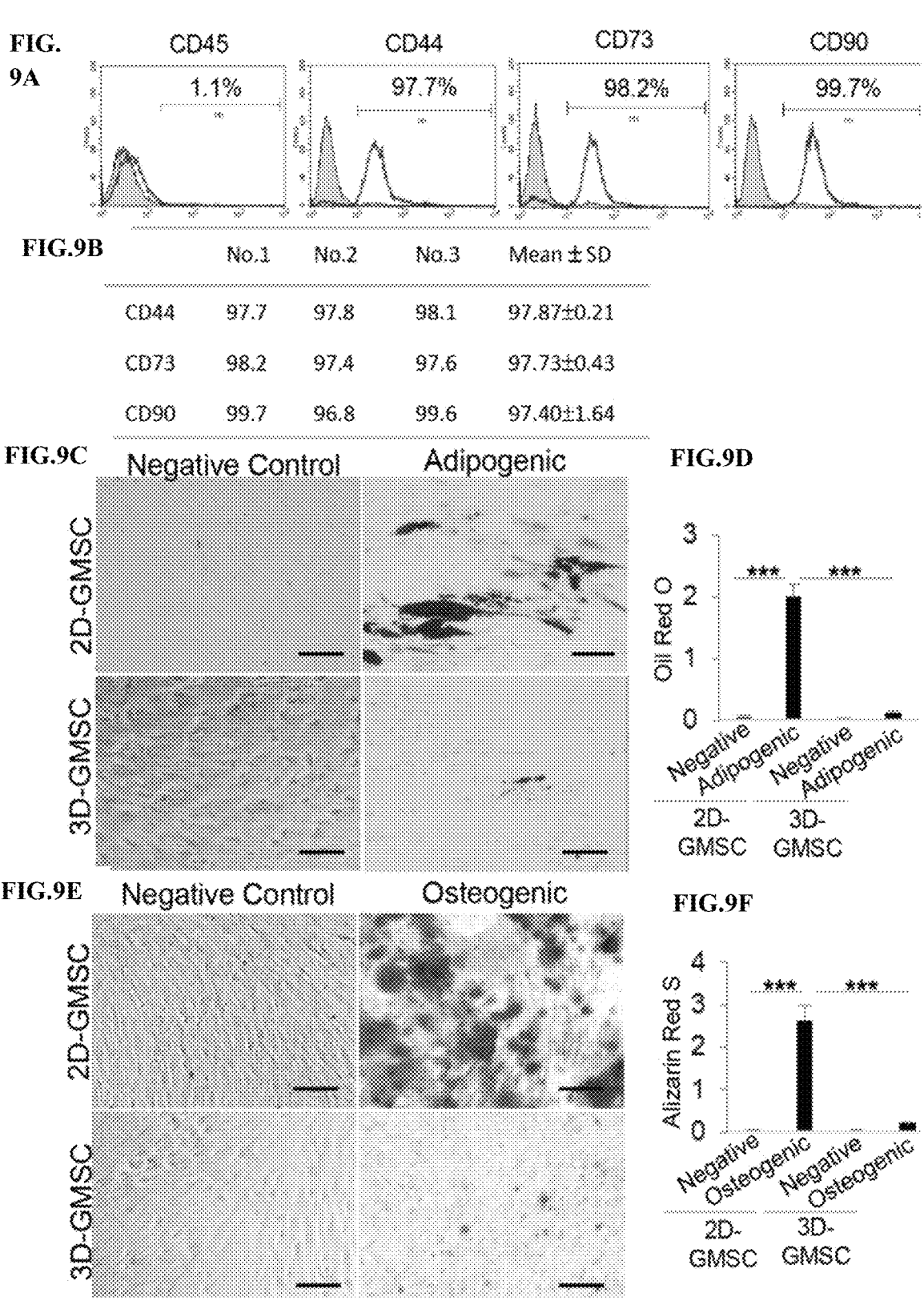

FIG. 9A-9F show characterization of gingiva-derived mesenchymal stem cells (GMSCs). FIG. 9A, Representative histograms of flow cytometric analysis of mesenchymal stem cell-related cell surface markers, CD44, CCD73, and CD90, in GMSCs. FIG. 9B, Expression of MSC-related cell surface markers in GMSCs derived from three healthy donors as determined by flow cytometry. FIG. 9C, Adipogenic differentiation of GMSCs cultured under 2D cultures or recovered following culturing in 3D-collagen hydrogel for 48 h. Adipocytes were determined by Oil Red O staining. FIG. 9D, Quantification of Oil Red O contents. FIG. 9E, Osteogenic differentiation of GMSCs cultured under 2D cultures or recovered following culturing in 3D-collagen hydrogel for 48 h. Osteocytes were determined by Alizarin Red S staining. FIG. 9F, Quantification of Alizarin Red S contents. Scale bar=50 μm (FIGS. 9C, 9E). Data represent the mean±SD, n=3 biological replicates. *p<0.001. Student's two-tailed unpaired t-test (FIGS. 9D, 9F**). 2D, GMSCs cultured in 2D-conditions; 3D, GMSC cultured in 3D-collagen hydrogel.

Figures 10A, 10B, 10C:
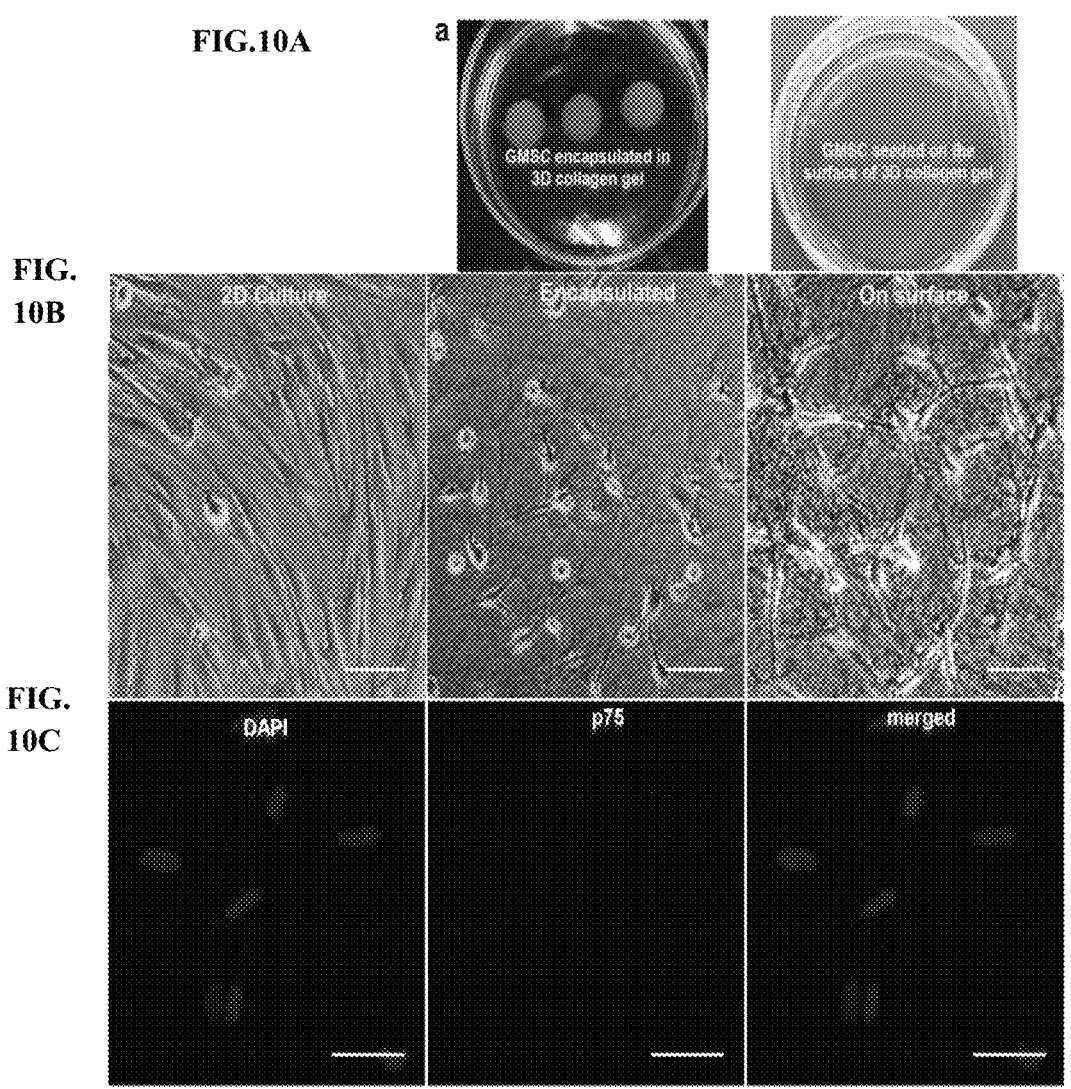

FIGS. 10A-10C show GMSCs cultured on the top surface of the methacrylated 3D-collagen hydrogel. FIG. 10A, The 2D plastic 4-well chambered cell culture slides were pre-coated with 4 mg/mL methacrylated collagen hydrogel. GMSCs then were seeded on the top surface of the solidified hydrogel and cultured in complete α-MEM for 48 h. FIG. 10B, The cellular morphology of GMSCs cultured under 2D plastic culture, encapsulation in 3D-collagen hydrogel, or on the top surface of the solidified hydrogel, respectively. FIG. 10C, Immunofluorescence staining showed no increase in the expression of p75$^{NTR}$ in GMSCs cultured on the top surface of the solidified collagen hydrogel. Scale bar=50 μm (FIGS. 10B, 10C). Images are representative of three independent experiments (biological replicates).

Figures 11A, 11B, 11C:
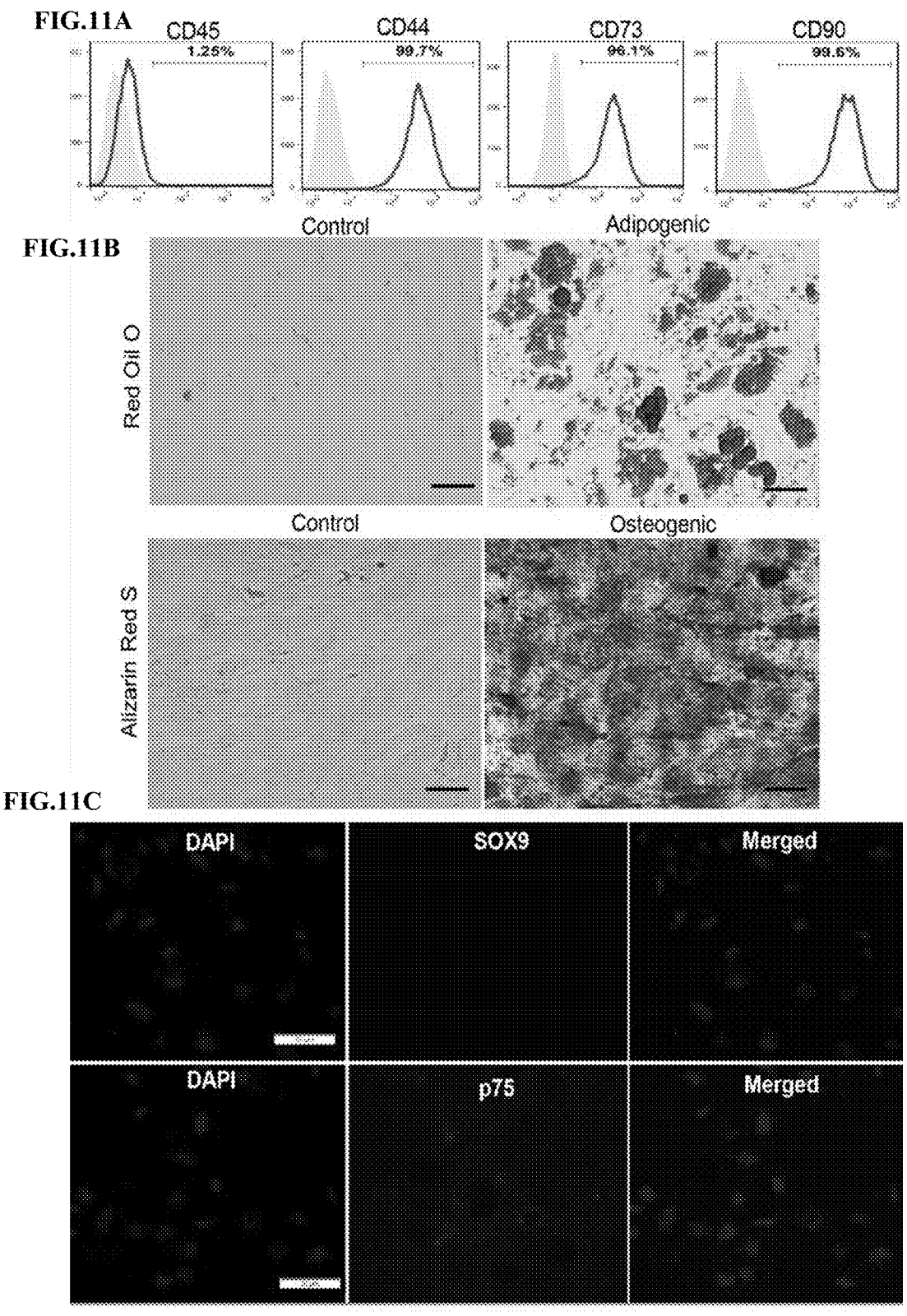

FIGS. 11A-11C show BMSCs cultured in methacrylated 3D-collagen hydrogel. FIG. 11A, Flow cytometric analysis of MSC-associated cell surface markers on human bone marrow-derived mesenchymal stem cells (hBMSCs). FIG. 11B, Adipogenic and osteogenic differentiation of hBMSCs as determined by Red Oil O and Alizarin Red S staining, respectively. Scale bar=50 μm. FIG. 11C, hBMSCs were encapsulated in 3D-collagen hydrogel (4 mg/mL) at a cell density of 2×10⁶/mL and cultured in complete α-MEM for 48 h. Cryosections of the 3D-collagen gels laden with hBMSCs were immunostained with a specific antibody for SOX9 or p75$^{NTR}$ followed by incubation with Alexa Fluor 488-conjugated secondary antibody. Nuclei were counterstained with 4', 6-diamidino-2-phenylindole (DAPI). Scale bar=20 μm. Data are representative of three independent experiments (biological replicates).

Figures 12A, 12B:
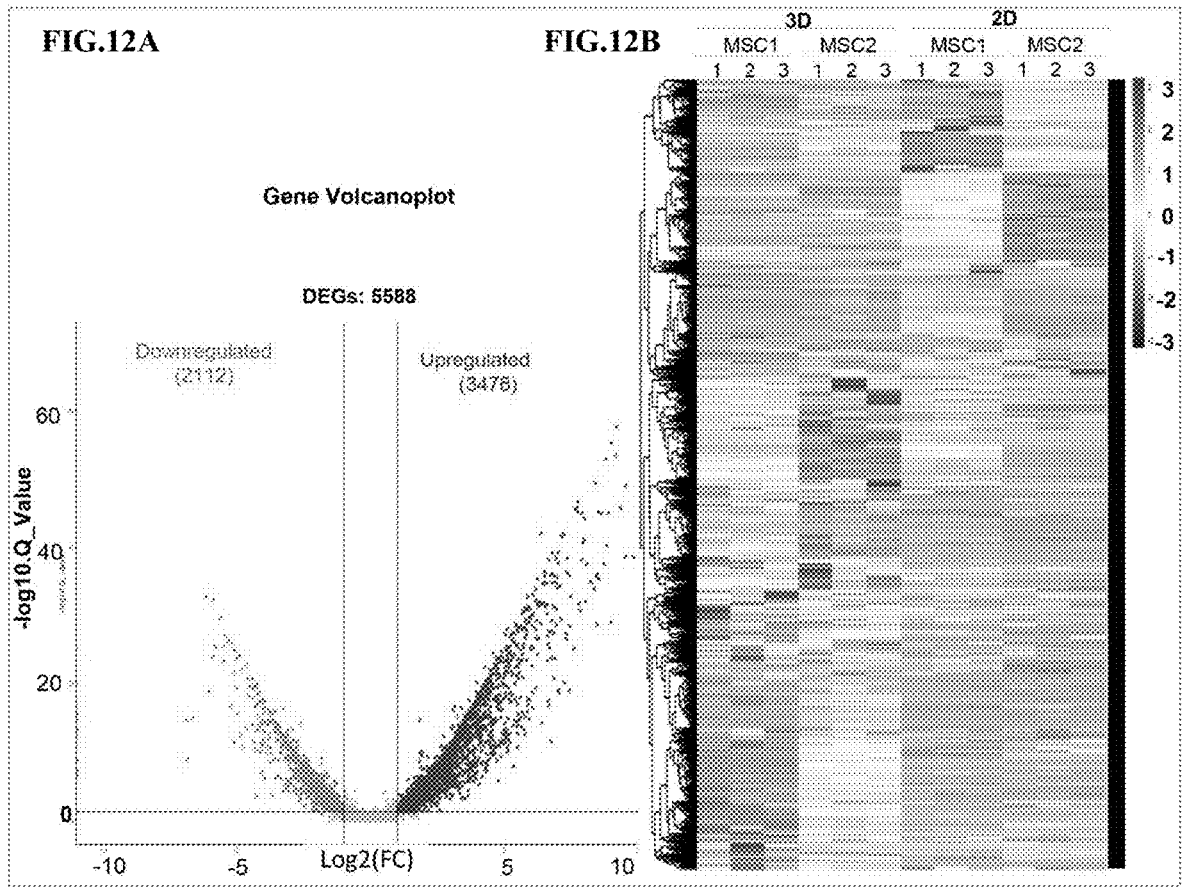

FIGS. 12A-12B show gene expression profiling by RNA-seq. GMSCs were cultured under 2D- and 3D-collagen hydrogel conditions for 48 h, respectively, and total RNA was extracted for RNA-seq. FIG. 12A, Volcano plot showing a total of 5588 differentially expressed genes (DEGs) with a fold change (FC)≥1 (3D-cultured GMSCs versus vs 2D-cultured counterparts). FIG. 12B, Heatmap showing relative representation of significant differentially expressed genes (DEGs) clustered according to expression pattern across samples (two biological replicates, GMSC1 and GMSC2; three technique replicates, 1, 2, 3). High expression low expressions are shown. DEGs, differentially expressed genes; 2D, GMSCs cultured in 2D-conditions; 3D, GMSC cultured in 3D-collagen hydrogel.

Figures 13A, 13B, 13C:
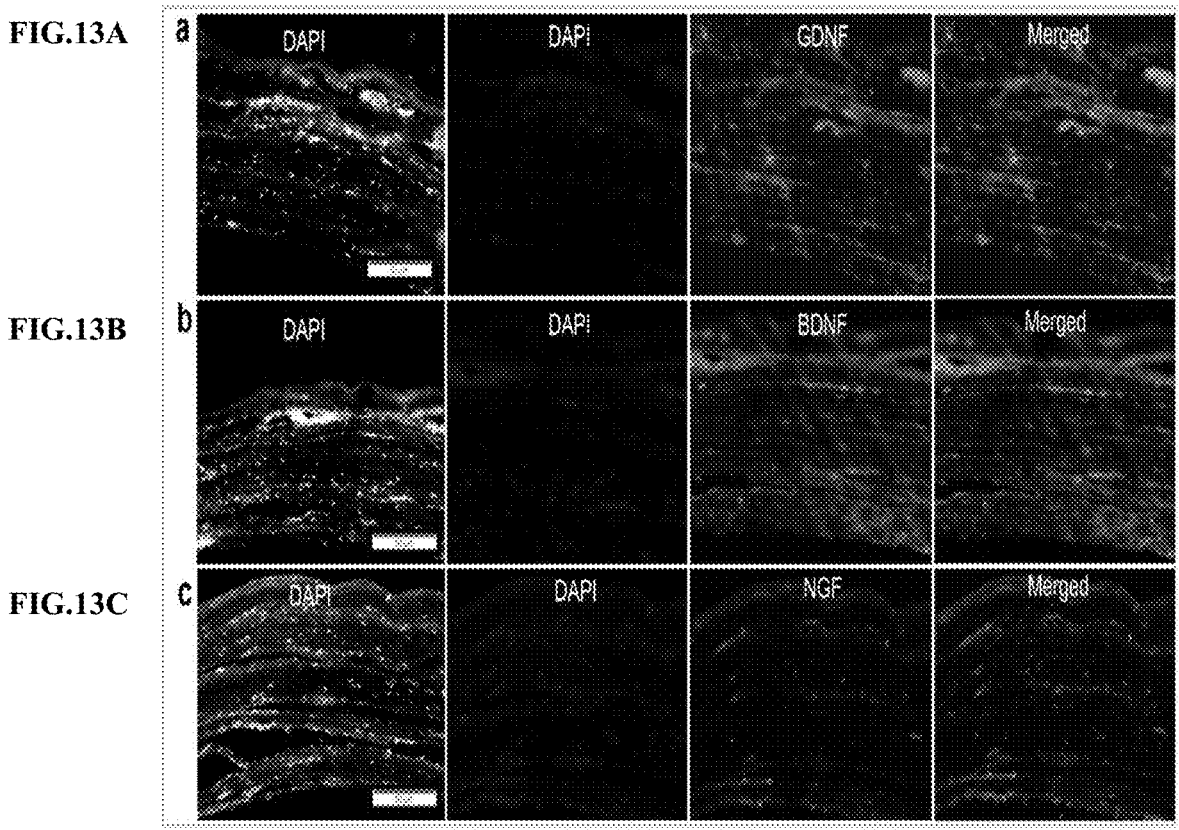

FIGS. 13A-13C show GMSC-derived NCSC/SCP-like cells encapsulated in 3D-collagen hydrogel transmigrated into the wall matrix of nerve conduits and expressed neurotrophic factors. GMSCs were encapsulated in 3D-collagen hydrogel at a final concentration of 4 mg/mL and a cell density of 2×10⁶/mL and filled into AxoGuard Nerve protector or connector (10 mm in length and 2 mm in inner diameter). Then, the constructs (nerve conduits containing 3D collagen hydrogel encapsulated with GMSCs) were cultured for 24 h in complete α-MEM for 24 h. Cryosections of nerve conduits were prepared for immunostaining with specific antibodies for GDNF (FIG. 13A), BDNF (FIG. 13B), or NGF (FIG. 13C), followed by incubation with Alexa Fluor 488-conjugated secondary antibodies. Nuclei were counterstained with 4', 6-diamidino phenylindole (DAPI). Scale bars=50 μm. Images are representative of three independent experiments (biological replicates).

Figures 14A, 14B, 14C:
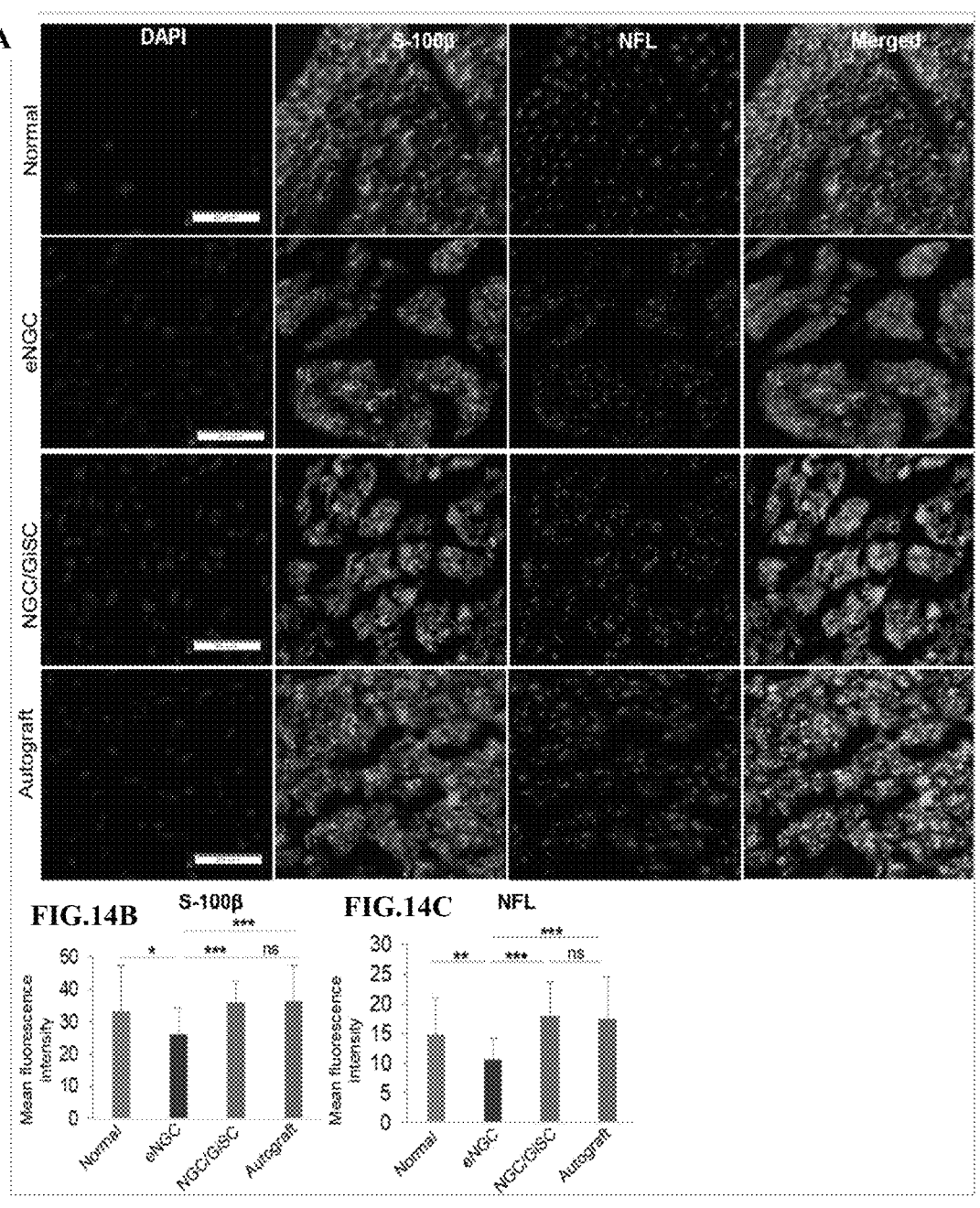

FIGS. 14A-14C show that implantation of NGC/GiSCs promotes axonal regeneration of transected facial nerves of rats. FIG. 14A, At 14 weeks post-injury and implantation, the newly regenerated facial nerves were harvested and cross-sectional cryosections (10 μm in thickness) were cut for immunofluorescence (IF) studies on the protein expression of S-100β and neurofilament (NFL). Nuclei were counterstained with 4', 6-diamidino-2-phenylindole (DAPI). Scale bars=50 μm. FIGS. 14B-14C: Quantification of the IF intensity of S-100β (FIG. 14B) and neurofilament (NFL) (FIG. 14C) expressions of 6 randomly selected regions of interest (ROIs). Data represent the mean±SD, n=3 rats. *p<0.05, p<0.01, *p<0.001; ns, no significance. One-way ANOVA with the Tukey's post test (FIG. 14B, 14C). NGC, nerve guidance conduit; eNGC, empty nerve conduit; GiSCs, GMSC-derived NCSC/SCP-like cells.

Figure 15:
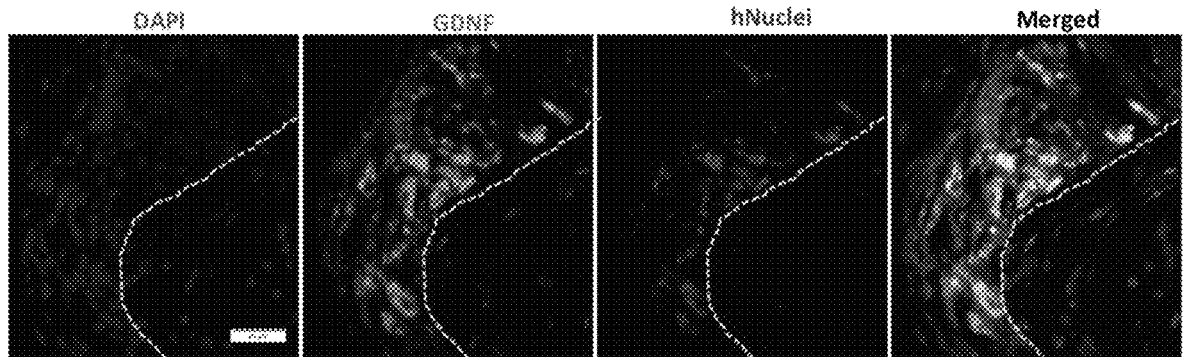

FIG. 15 depicts the fate of GiSCs integrated in the nerve conduits following implantation in vivo. 14 weeks post-injury and implantation, the newly regenerated facial nerves were harvested and cross-sectional cryosections (10 μm in thickness) were cut for immunofluorescence (IF) studies on expression of GDNF and human nuclei. Nuclei were counterstained with 4', 6-diamidino-2-phenylindole (DAPI). Scale bars=20 μm. Images are representative of three independent experiments. hNuclei, human nuclei.

Figures 2A, 2B, 2C, 2D, 2E, 2F:
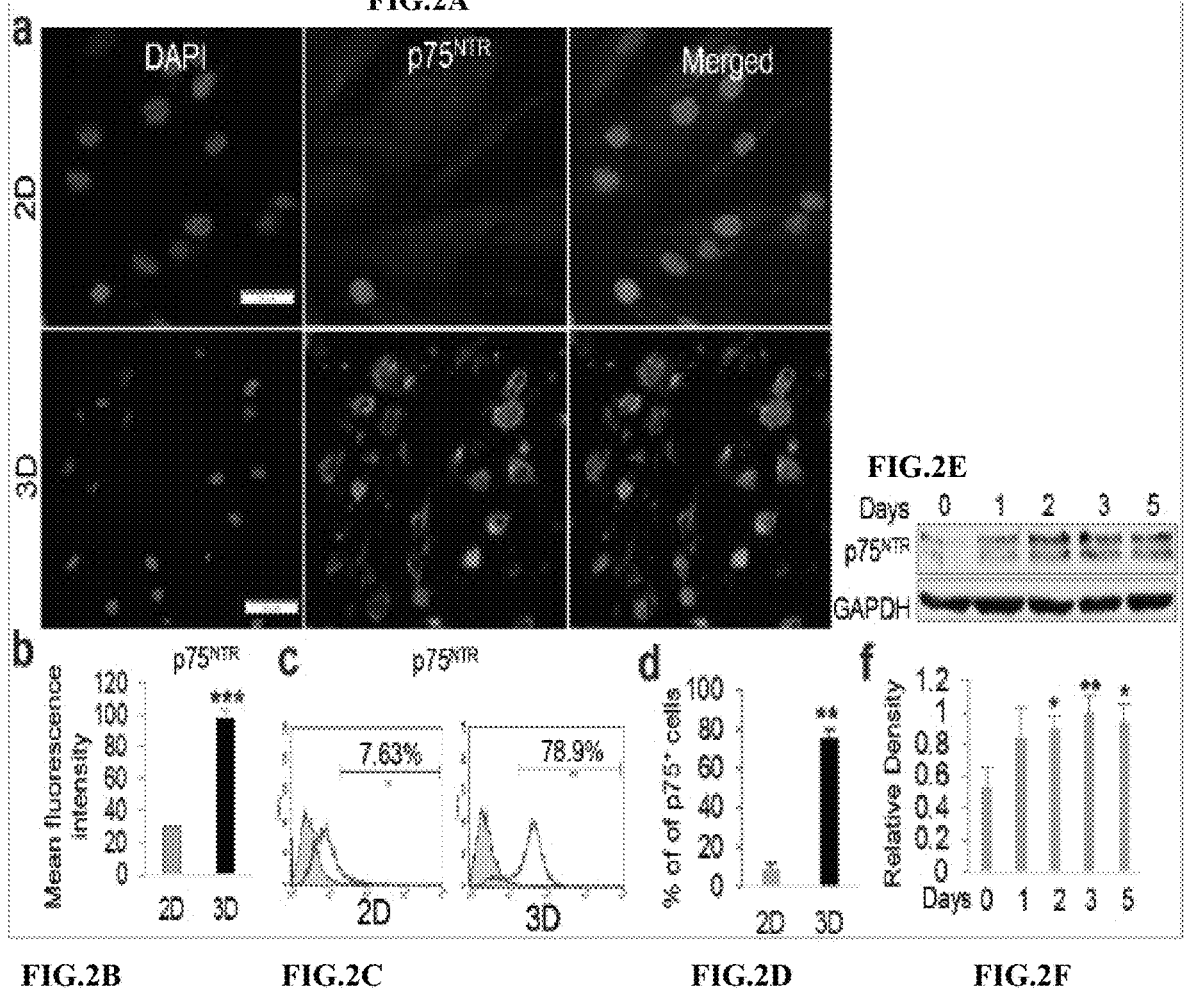
FIGS. 2A-2F show increased expression of $p75^{NTR}$ protein in GMSCs cultured in methacrylated 3D-collagen hydrogel. GMSCs were cultured under 2D cultures or in 3D-collagen hydrogel (at 4 mg/ml) in complete α-MEM for 48 h.
Figure 16:
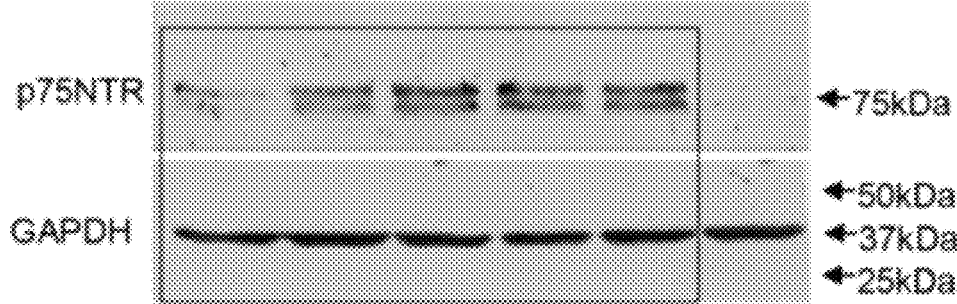
Figure 16:
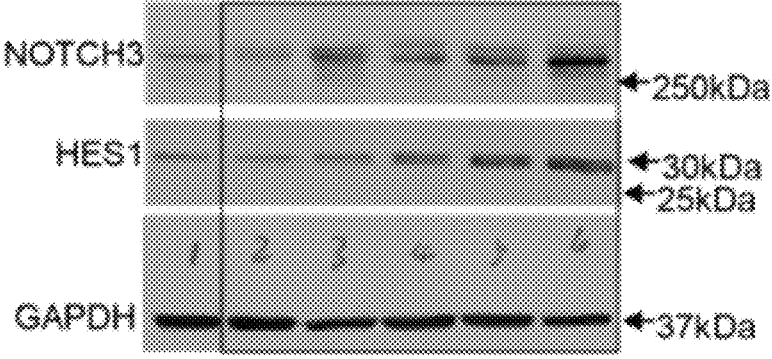

FIG. 16 show uncropped western blotting images for FIG. 2E (top blot) and FIG. 6D (bottom blot). All blots were derived from the same experiment and processed in parallel, where GAPDH was used as an internal loading control and the size markers were labeled.

Figures 17A, 17B, 17C, 17D:
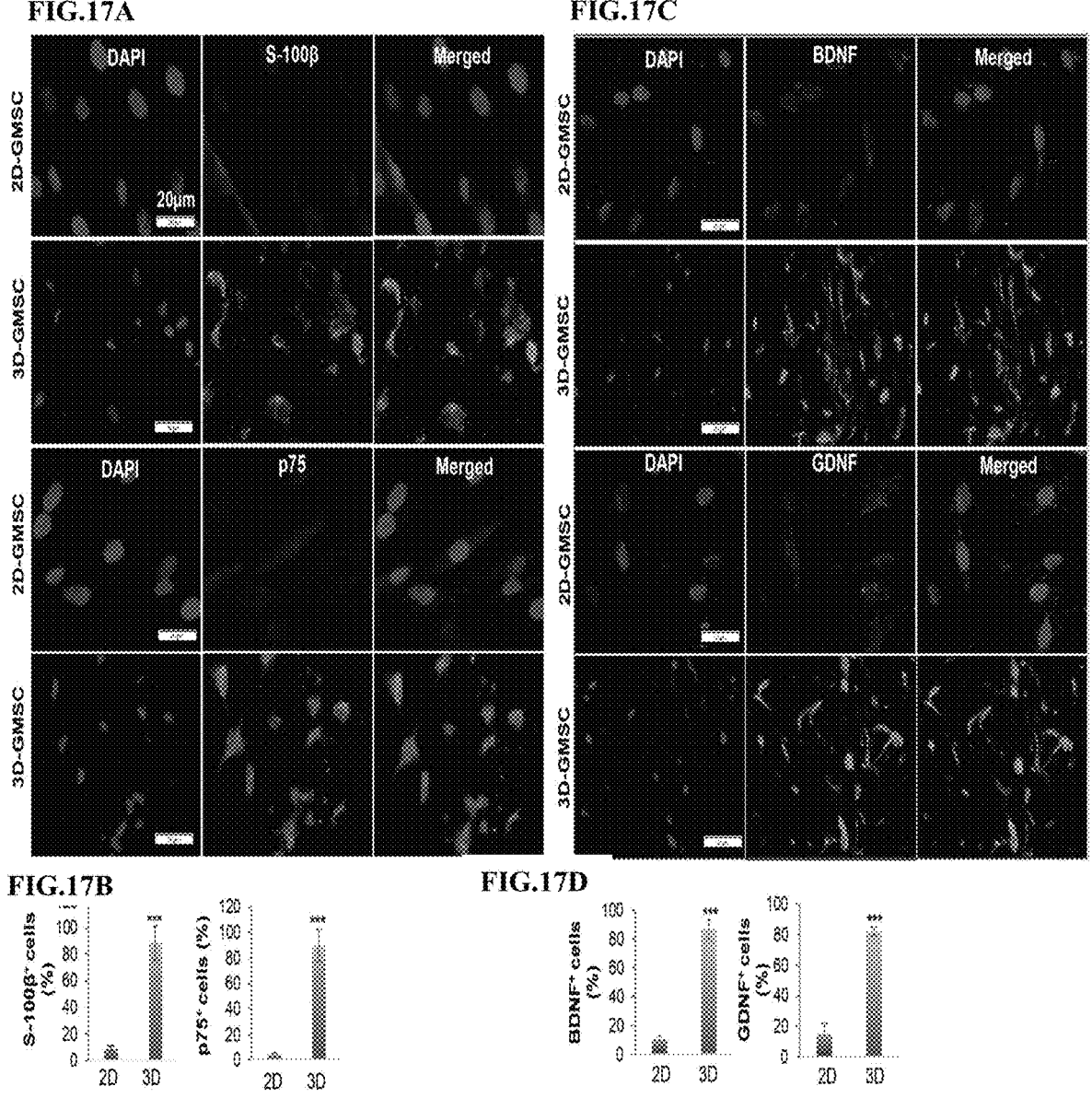

FIGS. 17A-17D depicts that 3D-collagen hydrogel directed the conversion of GMSCs into Schwann-like cells. GMSCs were cultured under 2D-culture conditions (2D-GMSC) or encapsulated in the methacrylated 3D-collagen hydrogel (4 mg/mL) at a cell density of $2\times10^6$/mL and allowed for gel formation at 37° C. for 20 min followed by culturing in complete α-MEM supplemented with 10% FBS for 48 h. FIG. 17A, 2D- or 3D-GMSCs that were immunostained with a specific antibody for S-100β or p75NTR followed by incubation with Alexa Fluor 488-conjugated secondary antibodies. Nuclei were counterstained with 4',6-diamidino-2-phenylindole (DAPI). Images were captured under a fluorescence microscope. Scale bars, 20 μm. FIG. 17B, is quantification of the percentage of S-100β⁺ and p75NTR⁺ cells. FIG. 17C, 2D- or 3D-GMSCs that were immunostained with a specific antibody for BDNF or GDNF followed by incubation with Alexa Fluor 488-conjugated secondary antibodies. Nuclei were counterstained with DAPI. Images were captured under a fluorescence microscope. Scale bars, 20 μm. FIG. 17D, Quantification of the percentage of BDNF⁺ and GDNF⁺ cells. Data represent the mean±SD. ***p<0.001 (3D vs. 2D); Student's two-tailed unpaired t test (FIGS. 17B, D). 2D, GMSCs cultured in 2D-conditions; 3D, GMSC cultured in the 3D-collagen hydrogel.

Figures 18A, 18B, 18C, 18D, 18E:
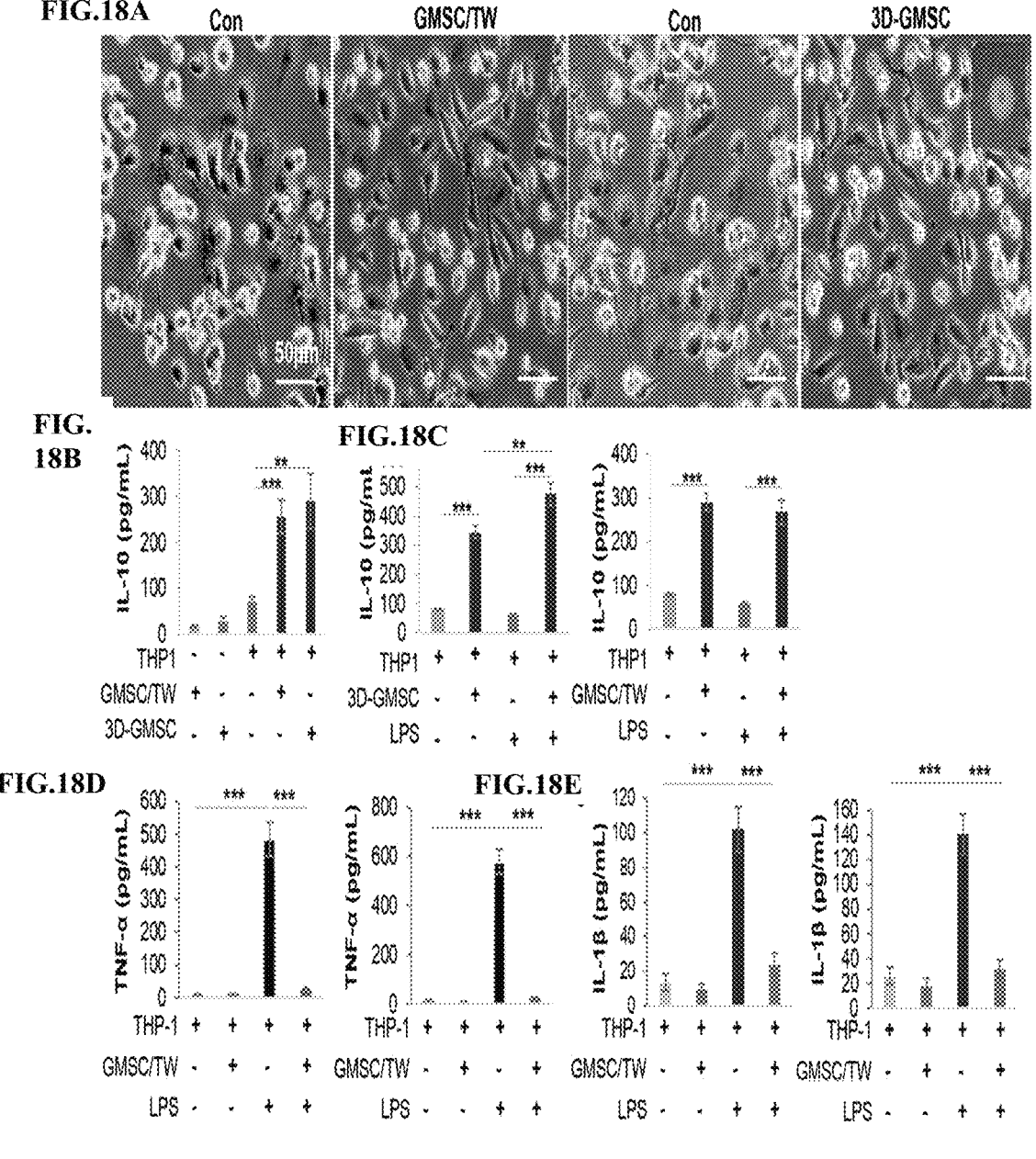

FIGS. 18A-18E show GMSCs encapsulated in the 3D-collagen hydrogel retain the immunomodulatory effects on macrophages. THP-1 macrophages were co-cultured with GMSCs either seeded in the upper chamber of a trans-well (TW) or encapsulated in the methacrylated 3D-collagen hydrogel (4 mg/mL) at a cell ratio of 2:1 (macrophages: GMSCs) for 48 h. FIG. 18A, The spindle-shaped morphological changes of THP-1 macrophages following co-culture with GMSCs. Scale bar, 50 μm. FIG. 18B, Following co-culture with MSCs for 48 h, the secretion of IL-10 in the culture media was determined by ELISA. FIGS. 18C-18E, Following co-culture with GMSCs for 48 h, THP-1 macrophages were stimulated with 100 ng/mL lipopolysaccharide (LPS) in fresh media for 3 h and the secretion of IL-10 (FIG. 18C), TNF-α (FIG. 18D), and IL-1β (FIG. 18E) was determined by ELISA, respectively. Data represent the mean±SD, n=3 biological replicates. p<0.01; *p<0.001; Student's two-tailed unpaired t test. TW, GMSCs cultured in a trans-well; 3D-GMSC, GMSC cultured in the 3D-collagen hydrogel.

Figures 19A, 19B, 19C, 19D:
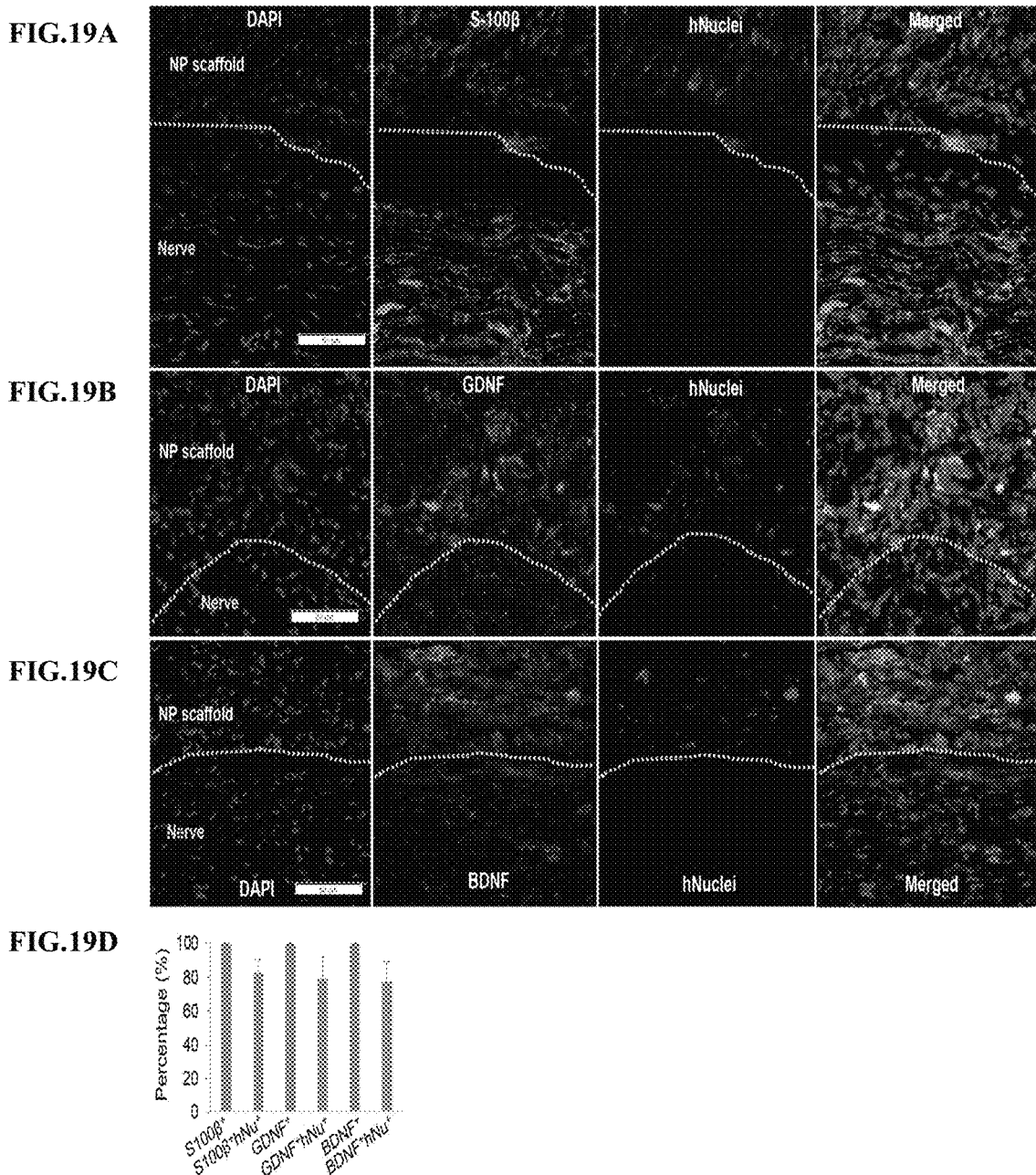

FIGS. 19A-19D depict the fate of GMSC-derived Schwann-like cells following transplantation within the functionalized nerve protectors to the crush injury site of rat sciatic nerves. The functionalized nerve protectors repopulated with GMSC-derived Schwann-like cells were implanted to wrap the injury segment of rat sciatic nerves. Four weeks post-implantation, the injured nerves were harvested and cryosections were prepared for immunofluorescence studies. The longitudinal cryosections were incubated with a specific mouse monoclonal antibody for human nuclei in combination with a rabbit polyclonal antibody for S-100β (FIG. 19A), GDNF (FIG. 19B), or BDNF (FIG. 19C) followed by incubation with Alexa Fluor 488- and 594-conjugated secondary antibodies. Nuclei were counterstained with 4',6-diamidino-2-phenylindole (DAPI). FIG. 19D, Quantification of the percentage of S-100β⁺, GDNF⁺, and BDNF⁺ cells co-immunostained with human nuclei by using ImageJ, which were designated as S-100β⁺hNu⁺, GDNF⁺hNu⁺, and BDNF⁺hNu⁺, respectively, whereby the percentage of total cells stained with green color was arbitrarily set as 100%. Images were captured under a fluorescence microscope. Scale bars, 50 μm. The dashed lines separated the longitudinally sectioned nerve tissues (the lower side) and implanted nerve protector (NP) scaffolds (the upper side).

Figures 20A, 20B, 20C, 20D, 20E, 20F:
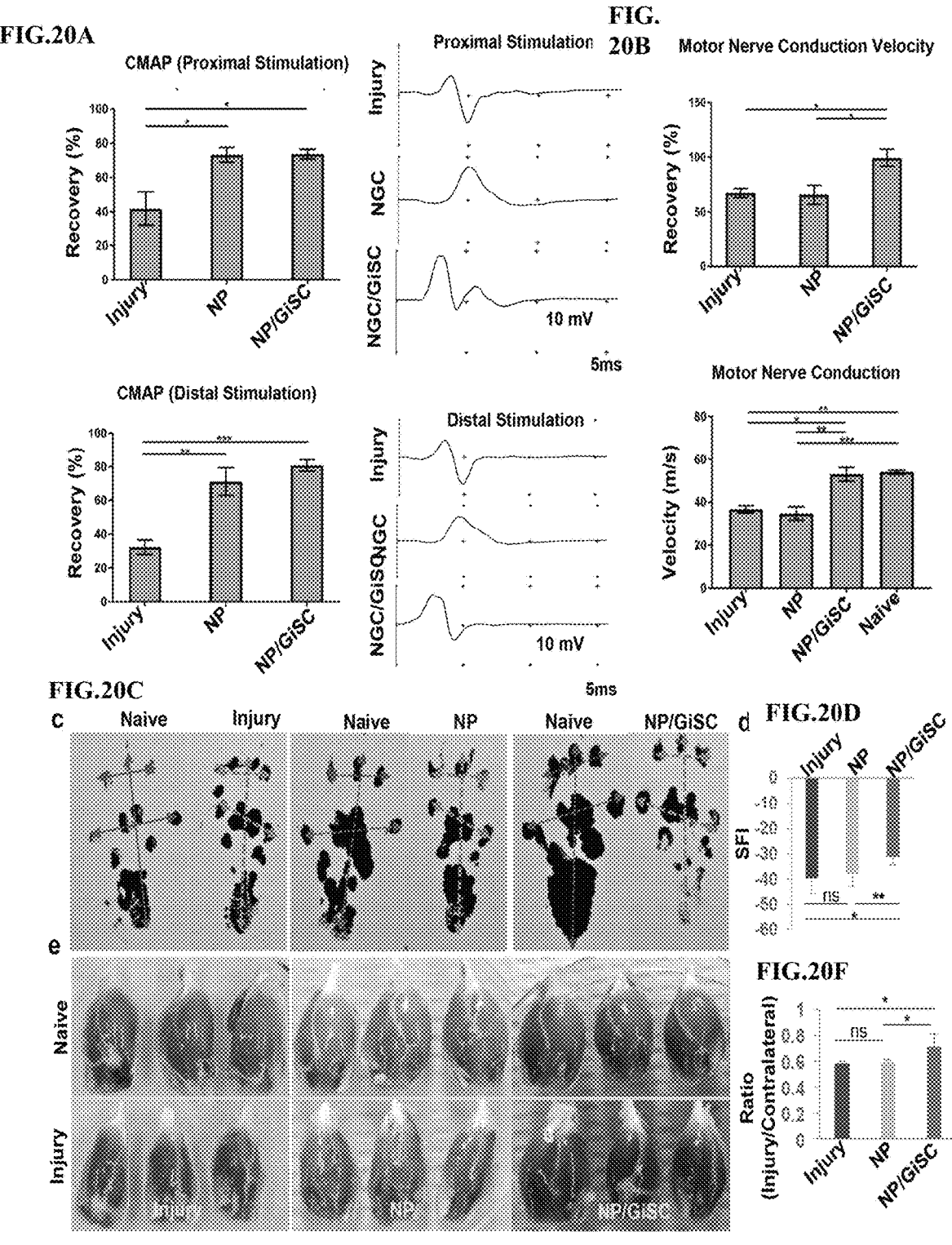

FIGS. 20A-20F show that implantation of nerve protectors repopulated with GMSC-derived Schwann-like cells improves functional recovery of crush-injured rat sciatic nerves. At 4 weeks post-injury and implantation, functional recovery of crush-injured sciatic nerves was analyzed. FIG. 20A, Compound muscle action potential (CMAP) recordings of the gastrocnemius muscles of both the injury site and the contralateral naive side of rats (n=4 for each group) following stimulation from either proximal or distal to the injury site. FIG. 20B, Analysis of motor nerve conduction velocity of both the injury side and the contralateral normal side of rats (n=4 for each group). FIGS. 20C-20D, Measurement of foot printings and sciatic functional index (SFI). FIG. 20E-20F, Measurement of the wet weight of gastrocnemius muscles of all animals from different groups, and the ratio was calculated individually (ratio=the weight of the injury side/the weight of contralateral naive side; n=6). Data are shown as the mean±SD. *p<0.05; p<0.01; *p<0.001; ns, no significance. One-way ANOVA with Tukey's posttest. Abbreviations: NP, nerve protector; NP/GiSCs, nerve protector repopulated with GMSC-derived Schwann-like cells (GiSC).

Figures 21A, 21B, 21C, 21D, 21E:
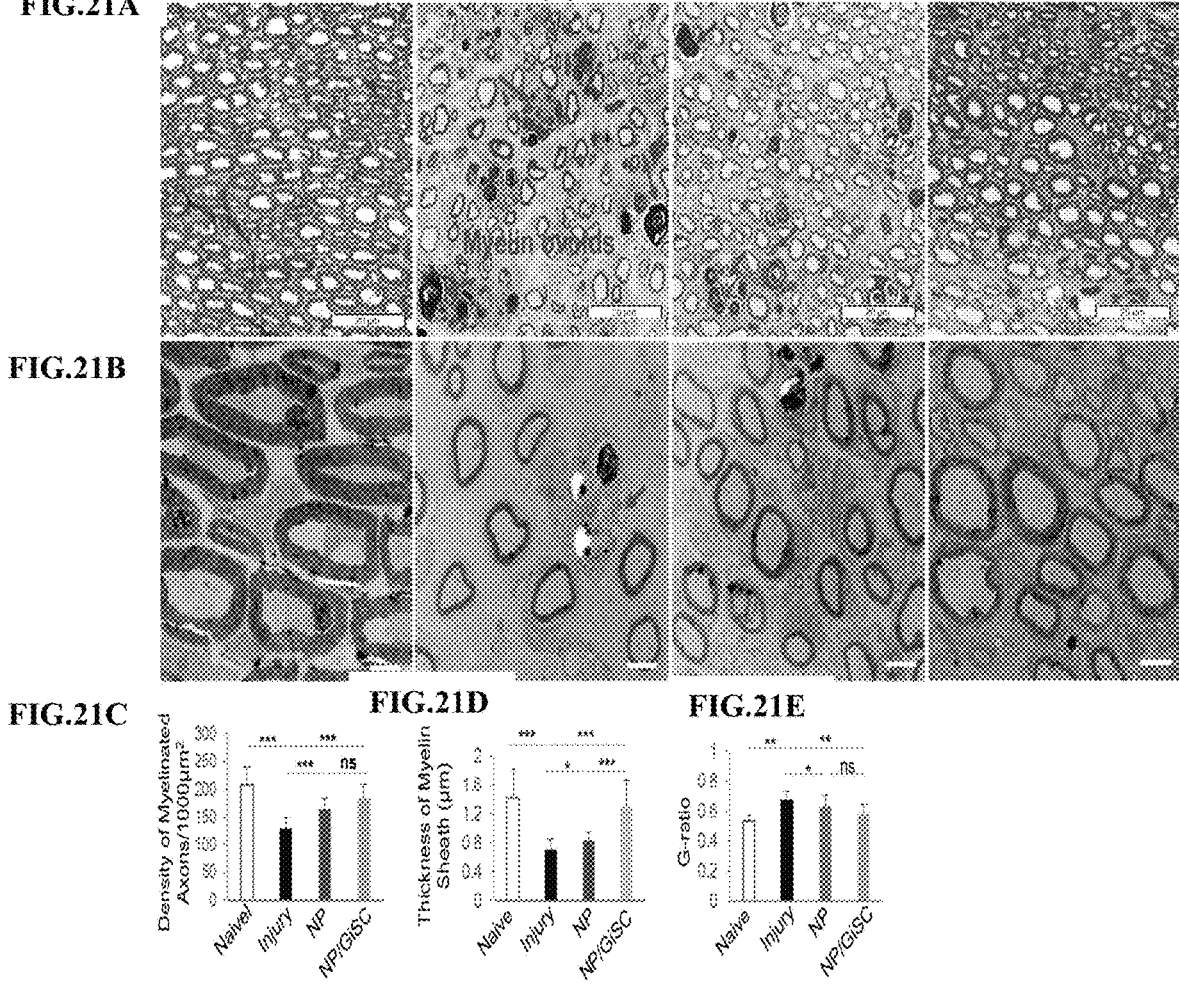

FIGS. 21A-21E show that implantation of nerve protectors repopulated with GMSC-derived Schwann-like cells promotes axonal regeneration and remyelination of crush-injured rat sciatic nerves. FIG. 21A, Toluidine blue staining of semi-thin sections of the injured nerves from different groups of rats at 4 weeks post-injury and implantation. Scale bars, 20 μm. FIG. 21B, Transmission electron microscopy (TEM) of ultrathin sections of the injured sciatic nerves from different groups of rats at 4 weeks post-injury and implantation. Scale bars, 4 μm. FIG. 21C, Quantification of the density of myelinated axons (the number of myelinated axons/1000 μm2). FIG. 21D, Quantification of the thickness of the myelin sheaths. FIG. 21E, Calculation of the G-ratios (the inner axonal diameter/the outer myelinated fiber diameter). Data are shown as the mean±SD. *p<0.05, **p<0.01,

***p<0.001; ns, no significance. One-way ANOVA with Tukey's posttest. Abbreviations: NP, nerve protector; NP/GiSCs, nerve protectors repopulated with GMSC-derived Schwann-like cells (GiSC).

Figures 22A, 22B, 22C, 22D:
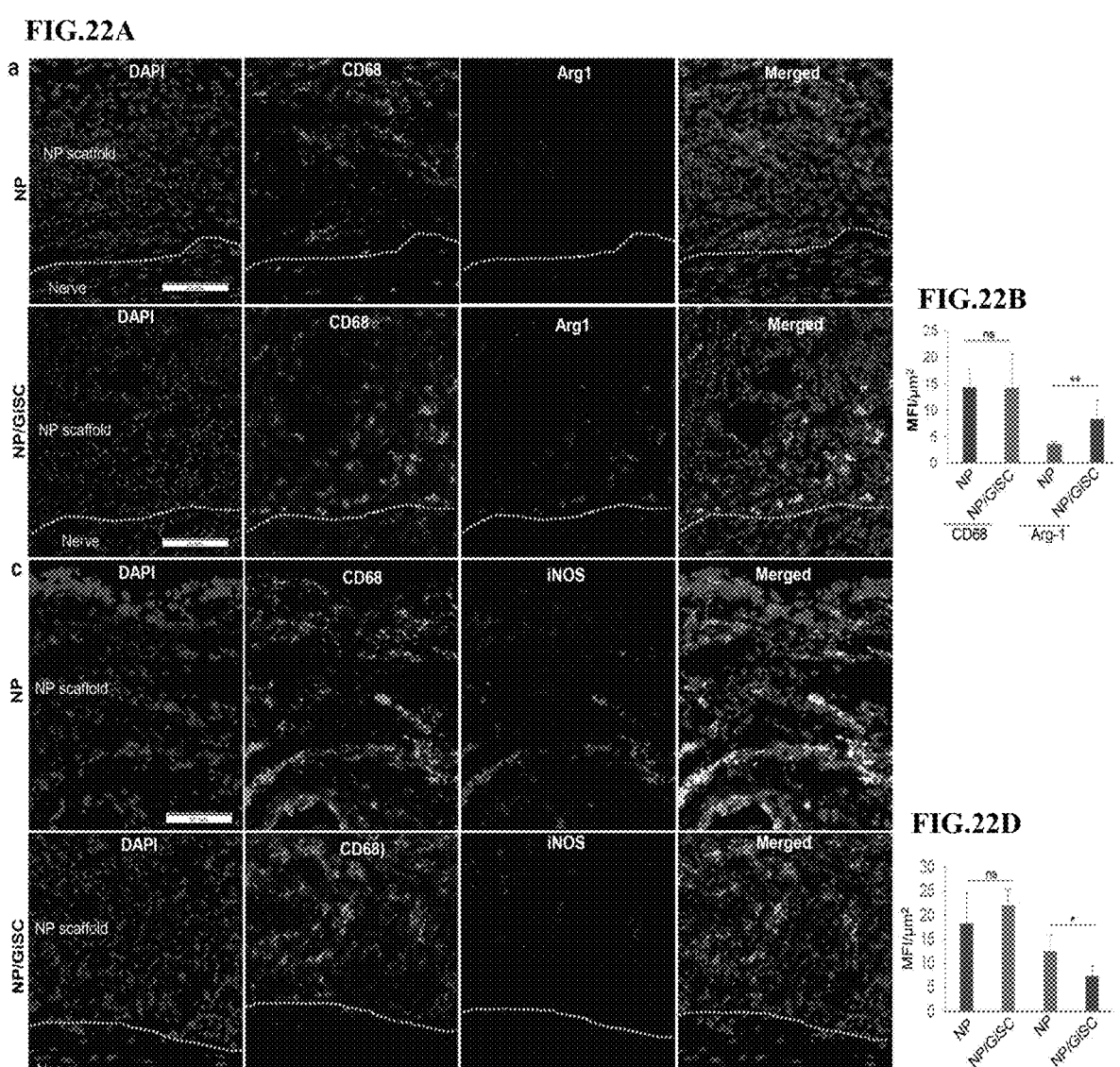

FIGS. 22A-22D show immunomodulatory effects of GMSC-derived Schwann-like cells on pro-inflammatory (M1)/pro-regenerative (M2) macrophages in peripheral regions of crush-injured rat sciatic nerves. The functionalized nerve protectors repopulated with GMSC-derived Schwann-like cells were implanted to wrap the injured regions of rat sciatic nerves. Four weeks post-implantation, the injured nerves were harvested and cryosections were prepared for immunofluorescence studies. FIG. 22A, The cryosections were incubated with a specific mouse monoclonal antibody for rat CD68 in combination with a rabbit polyclonal antibody for arginase-1 followed by incubation with Alexa Fluor 488- and 594-conjugated secondary antibodies. Nuclei were counterstained with 4',6-diamidino-2-phenylindole (DAPI). Images were captured under a fluorescence microscope. Scale bars, 50 μm. The dashed lines separated the longitudinally sectioned nerve tissues (the lower side) and implanted nerve protector (NP) scaffolds (the upper side). FIG. 22B, Semi-quantification of the integrated mean fluorescence intensity (MFI) for CD68 and arginase-1. Data are shown as the mean±SD. ns, no significance; p<0.01; Student's two-tailed unpaired t test. FIG. 22C, The cryosections were incubated with a specific mouse monoclonal antibody for rat CD68 in combination with a rabbit polyclonal antibody for iNOS followed by incubation with Alexa Fluor 488- and 594-conjugated secondary antibodies. Nuclei were counterstained with (DAPI). Images were captured under a fluorescence microscope. Scale bars, 50 μm. The dashed lines separated the longitudinally sectioned nerve tissues (the lower side) and implanted nerve protector (NP) scaffolds (the upper side). FIG. 21D**, Semi-quantification of the integrated mean fluorescence intensity (MFI) for CD68 and iNOS. Data are shown as the mean±SD. ns, no significance; *p<0.05; Student's two-tailed unpaired t test. Abbreviations: NP, nerve protector; NP/GiSC, nerve protector repopulated with GMSC-derived Schwann-like cells (GiSC); Arg1, arginase-1; iNOS, inducible nitric oxide synthase.

Figures 23A, 23B, 23C:
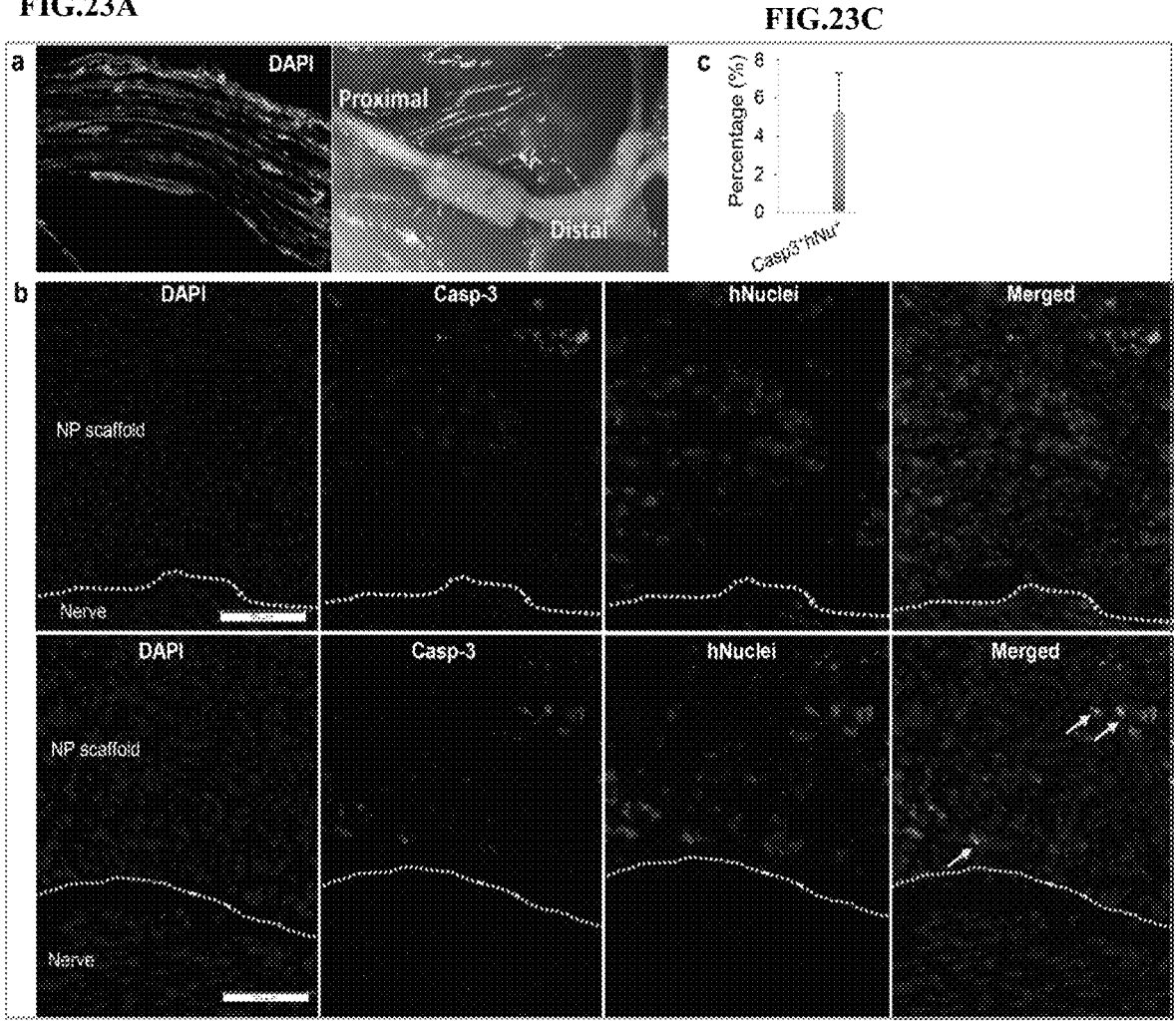

FIGS. 23A-23C show survival ability of GMSC-derived Schwann-like cells following transplantation within the functionalized nerve proctor to the crush injury site of rat sciatic nerves. FIG. 23A, The functionalized nerve protectors repopulated with GMSC-derived Schwann-like cells were implanted to wrap the injury segment of rat sciatic nerves. 4 weeks post-implantation, the injured nerves were harvested and cryosections were prepared for immunofluorescence studies. FIG. 23B, The cryosections were incubated with a specific mouse monoclonal antibody for human nuclei (hNu) in combination with a rabbit polyclonal antibody for the active form of caspase 3 (Casp-3) followed by incubation with Alexa Fluor 488- and 594-conjugated secondary antibodies. Nuclei were counterstained with 4', 6-diamidino-2-phenylindole (DAPI). Arrows indicate cells co-immunostaining with human nuclei and Casp-3 (green) (Casp3+hNu+). FIG. 23C, Quantification of the percentage of apoptosis in transplanted human MSCs presented by co-immunostaining with human nuclei and the active Casp-3 (green color) by using ImageJ. Images were captured under a fluorescence microscope. Scale bars, 50 μm. The dashed lines separated the longitudinally sectioned nerve tissues (the lower side) and implanted neurol protector (NP) scaffolds (the upper side).

Figures 24A, 24B, 24C:
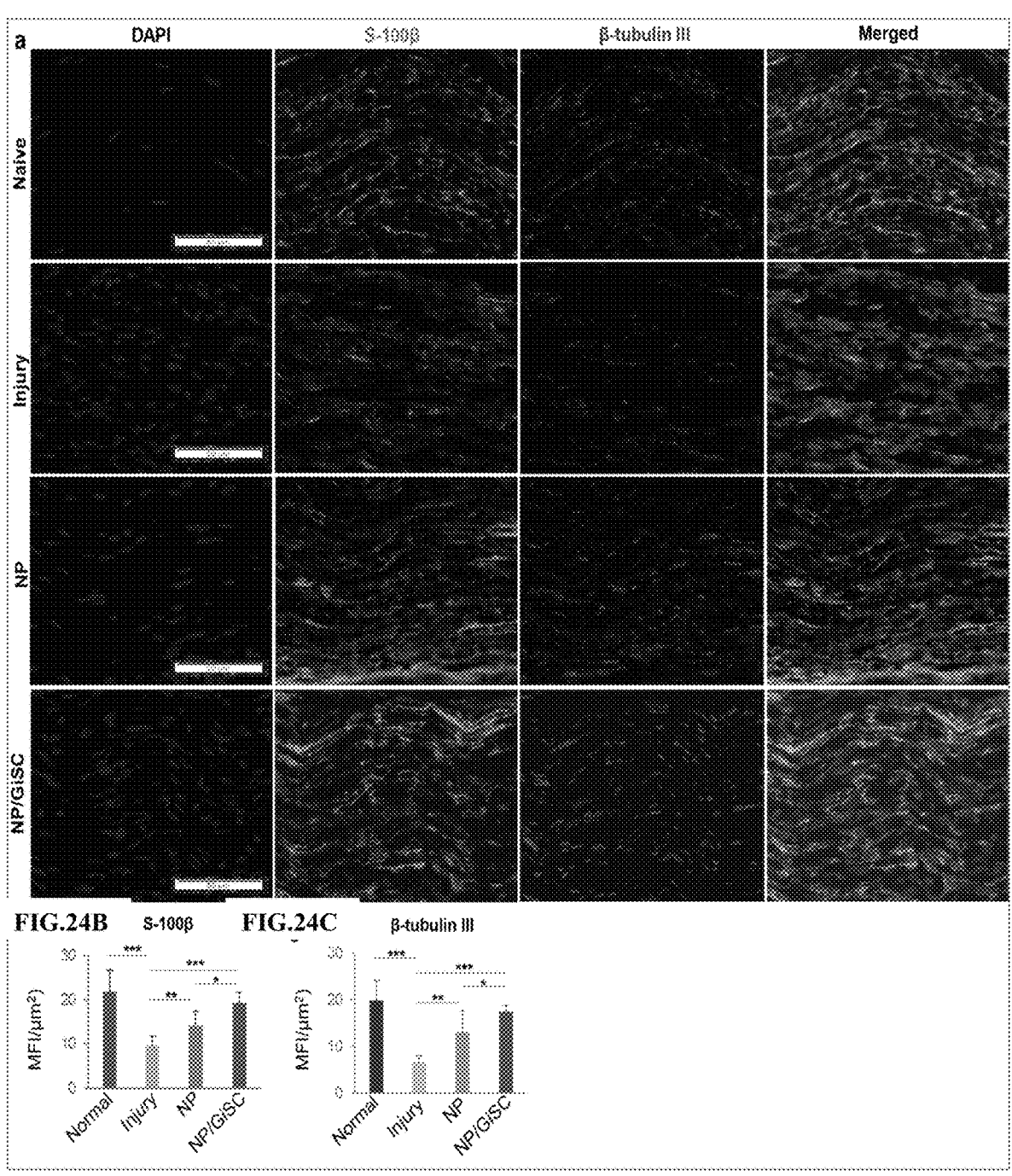

FIGS. 24A-24C show implantation of nerve protectors repopulated with GMSC-derived Schwann-like cells promote axonal regeneration of crush-injured rat sciatic nerves. The functionalized nerve protectors repopulated with GMSC-derived Schwann-like cells were implanted to wrap the injured regions of rat sciatic nerves. 4 weeks post-implantation, the injured nerves were harvested and cryosections were prepared for immunofluorescence studies. FIG. 24A, The cryosections were incubated with a specific mouse monoclonal antibody for β-tubulin III in combination with a rabbit polyclonal antibody for S-100β followed by incubation with Alexa Fluor 488- and 594-conjugated secondary antibodies. Nuclei were counterstained with 4', 6-diamidino-2-phenylindole (DAPI). Images were captured under a fluorescence microscope. Scalebars, 50 μm. FIGS. 24B-24C, Semi-quantification of the integrated mean fluorescence intensity (MFI) for S-100β and β-tubulin III. Data are shown as the mean±SD. *p<0.05, p<0.01, *p<0.01. Student's two-tailed unpaired t-test. Abbreviations: NP, nerve protector; NP/GiSC, nerve protector repopulated with GMSC-derived Schwann-like cells (GiSC).

Figures 25A, 25B:
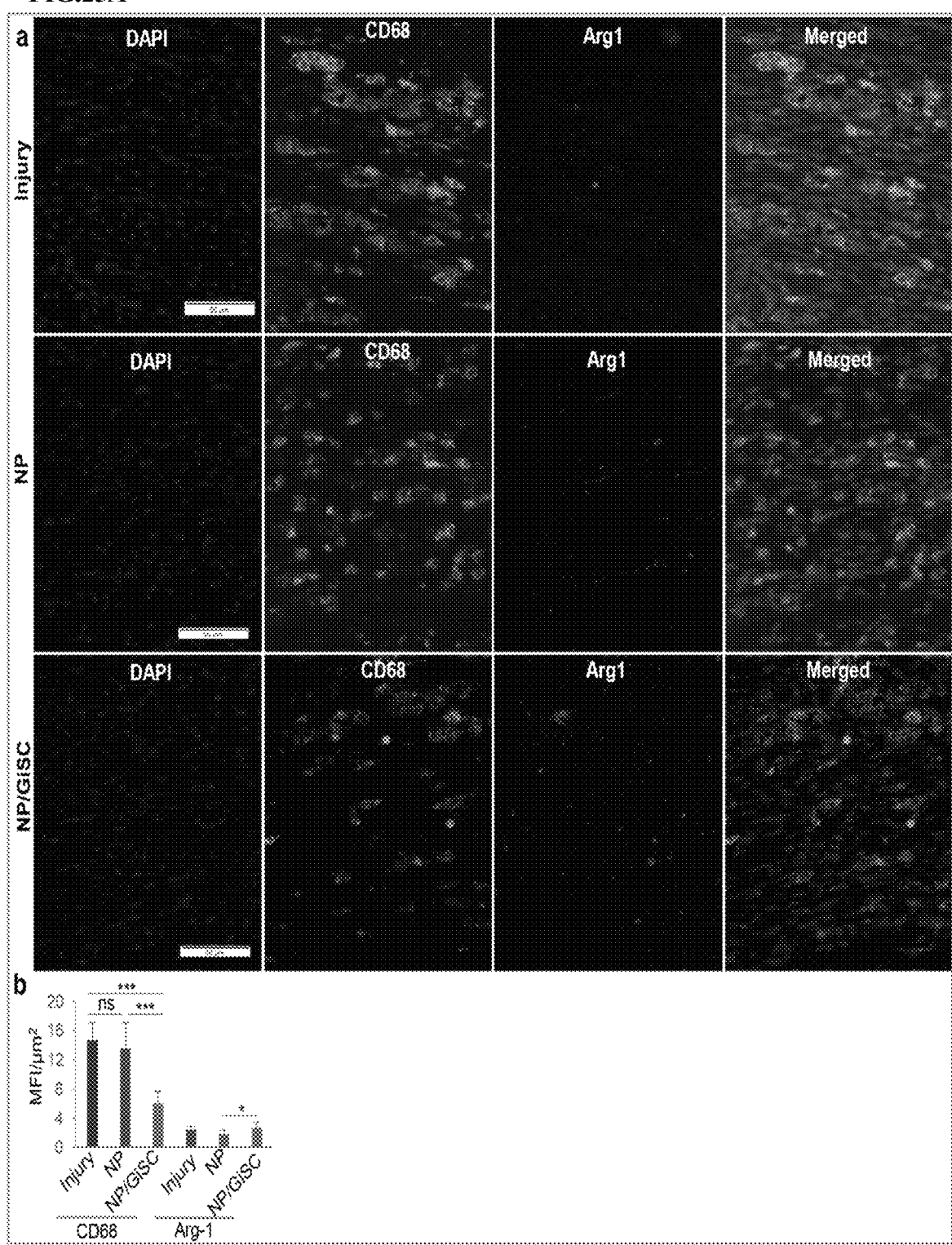

FIGS. 25A-25B show immunomodulatory effects of GMSC-derived Schwann-like cells on M2 macrophages within crush-injured rat sciatic nerves. The functionalized nerve protectors repopulated with GMSC-derived Schwann-like cells were implanted to wrap the injured regions of rat sciatic nerves. Four weeks post-implantation, the injured nerves were harvested and cryosections were prepared for immunofluorescence studies. FIG. 25A, The cryosections were incubated with a specific mouse monoclonal antibody for rat CD68 in combination with a rabbit polyclonal antibody for arginase-1 followed by incubation with Alexa Fluor488- and 594-conjugated secondary antibodies. Nuclei were counterstained with 4', 6-diamidino-2-phenylindole (DAPI). Images were captured under a fluorescence microscope. Scale bars, 50 μm. FIG. 25B, Semi-quantification of the integrated mean fluorescence intensity (MFI) for CD68 and iNOS. Data are shown as the mean±SD. ns, no significance; *p<0.05; ***p<0.001. Student's two-tailed unpaired t test. Abbreviations: NP, nerve protector; NP/GiSC, nerve protector repopulated with GMSC-derived Schwann-like cells (GiSC); Arg-1, arginase-1.

Figures 26A, 26B:
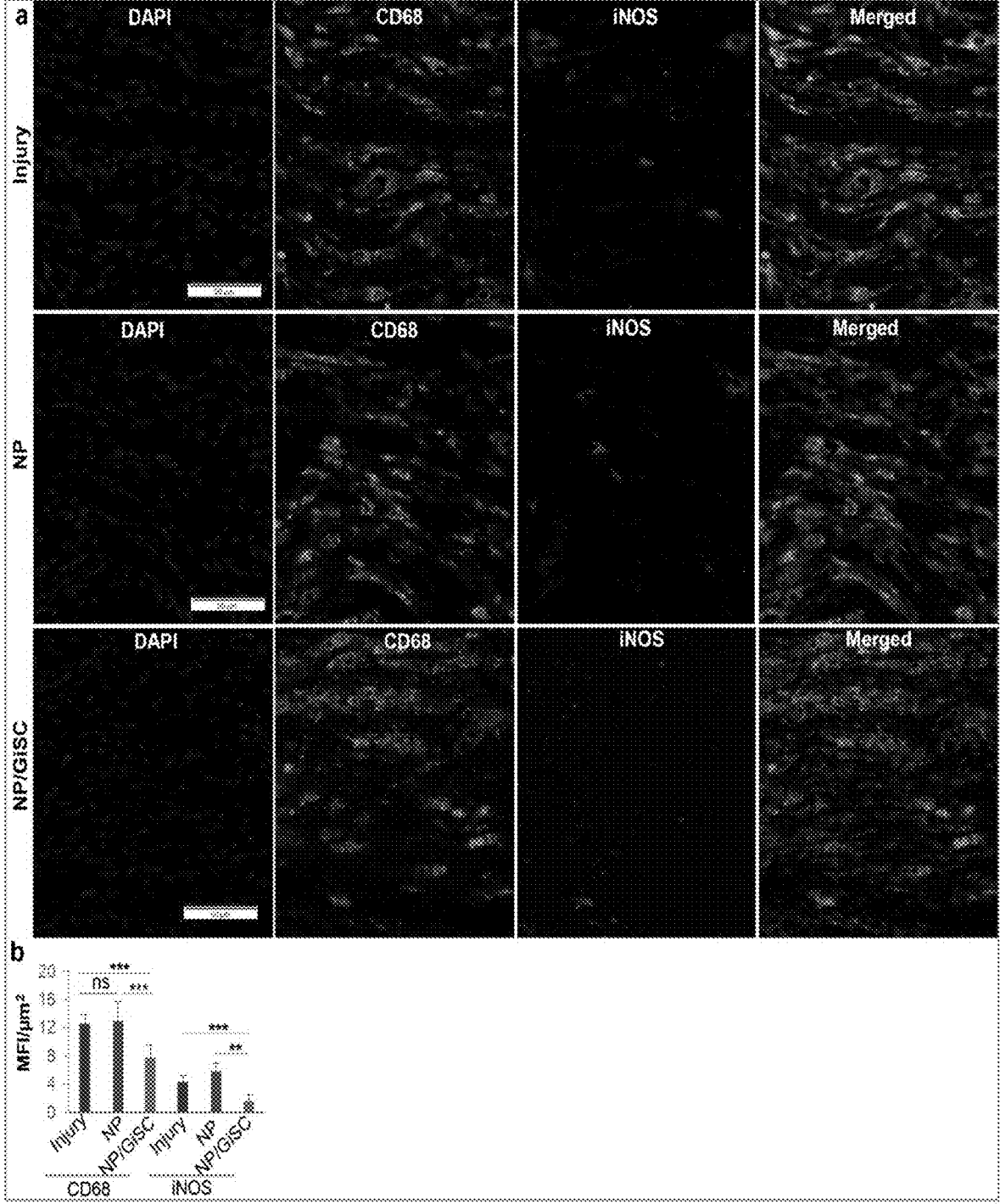

FIGS. 26A-26B show immunomodulatory effects of GMSC-derived Schwann-like cells on M1 macrophages within crush-injured rat sciatic nerves. The functionalized nerve protectors repopulated with GMSC-derived Schwann-like cells were implanted to wrap the injured regions of rat sciatic nerves. 4 weeks post-implantation, the injured nerves were harvested and cryosections were prepared for immunofluorescence studies. FIG. 26A, The cryosections were incubated with a specific mouse monoclonal antibody for rat CD68 in combination with a rabbit polyclonal antibody for iNOS followed by incubation with Alexa Fluor488- and 594-conjugated secondary antibodies. Nuclei were counterstained with 4', 6-diamidino-2-phenylindole (DAPI). Images were captured under a fluorescence microscope. Scale bars, 50 μm. FIG. 26B, Semi-quantification of the integrated mean fluorescence intensity (MFI) for CD68 and iNOS. Data are shown as the mean±SD. ns, no significance; *p<0.05; ***p<0.001. Student's two-tailed unpaired t-test. Abbreviations: NP, nerve protector; NP/GiSC, nerve protector repopulated with GMSC-derived Schwann-like cells (GiSC); iNOS, inducible nitric oxide synthase.

DETAILED DESCRIPTION

In one aspect, the invention provides a functionalized nerve guidance conduit (NGC) comprising a wall matrix comprising: a decellularized extracellular matrix; and neurotrophic factor-expressing neural crest stem-like cells (NCSC) and/or Schwann cell precursor-like (SCP) cells embedded in the wall matrix.

In another aspect, the invention provides a functionalized nerve protector (NP) comprising a wall matrix comprising: a decellularized extracellular matrix; and neurotrophic factor-expressing neural crest stem-like cells (NCSC) and/or Schwann cell precursor-like (SCP) cells embedded in the wall matrix.

In another aspect, the invention provides a method of making neurotrophic factor-expressing neural crest stem-like cells (NCSC) and/or Schwann cell precursor-like (SCP) cells, the method comprising: providing gingival-derived mesenchymal stem cells (GMSCs); and culturing the GMSCs in a 3D-collagen hydrogel, thereby making neurotrophic factor-expressing NCSC and/or SCP cells.

In another aspect, the invention provides a method of making a functionalized nerve guidance conduit, the method comprising: providing gingival-derived mesenchymal stem cells (GMSCs); culturing the GMSCs in a 3D-collagen hydrogel, thereby making neurotrophic factor-expressing neural crest stem-like cells (NCSC) and/or Schwann cell precursor-like (SCP) cells; filling a nerve guidance conduit with the neurotrophic factor-expressing NCSC and/or SCP cells; and culturing the nerve guidance conduit in vitro, thereby forming a functionalized nerve guidance conduit.

In another aspect, the invention provides a method of treating a nerve injury in a subject in need thereof, the method comprising implanting a functionalized nerve guidance conduit (NGC) at a site of nerve injury in the subject, wherein the NGC comprises a wall matrix comprising: a decellularized extracellular matrix; and neurotrophic factor-expressing neural crest stem-like cells (NCSC) and/or Schwann cell precursor-like (SCP) cells embedded in the wall matrix, thereby treating the nerve injury.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Nerve guidance conduit" or "NGC" or "nerve protector" as used herein means conduits/protectors made from decellularized multi-laminar extracellular matrix (ECM). The ECM may be autogenic, allogeneic, or xenogeneic with respect to a subject receiving the NGC/NP. Various ECMs are commercially available.

"Neurotrophic factor-expressing neural crest stem-like cells (NCSC) and/or Schwann cell precursor-like cells" (referred to herein as "GiSCs") means gingiva-derived mesenchymal stem cell (GMSC)-derived GiSCs with increased expression of GDNF and BDNF as compared with the parental GMSCs.

The term "subject" is intended to include living organisms in which an immune response can be elicited (e.g., mammals). A "subject" or "patient," as used therein, may be a human or non-human mammal. Non-human mammals include, for example, non-human primates as well as livestock and pets, such as simian, ovine, bovine, porcine, canine, feline, and murine mammals. Preferably, the subject is human.

To "treat" a disease as the term is used herein, means to reduce the frequency or severity of at least one sign or symptom of a disease or disorder experienced by a subject.

As used herein, the term "treatment" or "treating" encompasses prophylaxis and/or therapy. Accordingly, the compositions and methods of the present invention are not limited to therapeutic applications and can be used in prophylaxis ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Without wishing to be limited by theory, the invention is based in part on the unexpected discovery that mesenchymal stem cells obtained from gingival tissue (i.e., gingiva-derived mesenchymal stem cells (GSMCs)) differentiate into neurotrophic factor-expressing neural crest stem-like cells (NCSC) and/or Schwann cell precursor-like (SCP) cells when cultured in a 3D-collagen hydrogel, and that the neurotrophic factor-expressing NCSC and/or SCP cells spontaneously transmigrate into an extracellular matrix when cultured. Accordingly, in one aspect the invention provides a functionalized nerve guidance conduit (NGC) comprising a wall matrix comprising a decellularized extracellular matrix and neurotrophic factor-expressing neural crest stem-like cells (NCSC) and/or Schwann cell precursor-like (SCP) cells embedded in the wall matrix.

In various embodiments, the neurotrophic factor-expressing neural crest stem-like cells (NCSC) and/or Schwann cell precursor-like (SCP) cells are generated from gingiva-derived mesenchymal stem cells (GMSCs). In comparison to the parental GMSCs, this GMSC-derived NCSC and/or SCP cells showed increased expression of glial cell-derived neurotrophic factor (GDNF) and brain-derived neurotrophic factor (BDNF) at the protein level (as determined by immunofluorescence studies). Unexpectedly, the GMSC-derived NSCS and/or SCP cells were further characterized by increased expression of p75$^{NTR}$ (also known as p75 or Low Affinity Nerve Growth Factor Receptor (NGFR)), SRY-Box Transcription Factor (Sox9), ERBB Receptor Feedback Inhibitor 1 (Errfi1), Neurotrophin 3 (Ntf3), and Twist Family BHLH Transcription Factor 1 (Twist 1). The GMSC-derived NCSC and/or SCP cells positively expressed glial/Schwann cell-related genes, such as S-100β, Glial Fibrillary Acidic Protein (GFAP), and SOX10, and display increased expression of NOTCH signaling components, such as NOTCH3 signaling pathway components DLL1, DLL4, JAG2, Notch3, Hes1, and Hey1. Additionally, in comparison to the parental GMSCs, the GMSC-derived NCSC and/or SCP cells showed decreased expression of mesenchymal genes, such as type I collagen (ColI), vinculin (VCL), β-actin, Cd90, and Cd73, as determined by qRT-PCR. Further, GMSCs cultured in 3D collagen hydrogel underwent morphological changes including reduced cell volume, nuclear size, and relaxation of cytoskeleton. Additionally, the GMSCs cultured in 3D collagen hydrogel lost their multipotent differentiation capacities into adipocytes and osteocytes.

In various embodiments, the neurotrophic factor-expressing NCSC and/or SCP cells express at least one neurotrophic factor selected from GDNF and BDNF. In various embodiments, the neurotrophic factor-expressing NCSC and/or SCP cells further express at least one marker selected from the group consisting Low Affinity Nerve Growth Factor Receptor (NGFR), SRY-Box Transcription Factor 9 (Sox9), ERBB Receptor Feedback Inhibitor I (ERRFI1), Neurotrophin 3 (Ntf3), Twist Family BHLH Transcription Factor 1 (Twist 1), S-100β, SRY-Box Transcription Factor 10 (Sox10), and Glial Fibrillary Acidic Protein (GFAP). In various embodiments, the neurotrophic factor-expressing NCSC and/or SCP cells further express at least one NOTCH signaling pathway marker selected from the group consisting of DLL1, DLL4, JAG2, Notch3, Hes1, and Hey1. In various embodiments, the neurotrophic factor-expressing NCSC and/or SCP cells express all or any combination of these markers.

In various embodiments, in vitro, co-culture of GMSCs encapsulated in the 3D-collagen hydrogel with macrophages increase the secretion of IL-10, an anti-inflammatory cytokine characteristic of pro-regenerative (M2) macrophages, but robustly reduce LPS-stimulated secretion of TNF-1α and IL-1β, two cytokines characteristic of pro-inflammatory (M1) macrophages.

The wall matrix refers to the outer surface of the nerve guidance conduit (NGC) that surrounds the damaged nerve when the NGC is implanted into a subject. In various embodiments, the wall matrix comprises decellularized extracellular matrix material that forms the structure of the NGC. It has been unexpectedly discovered that neurotrophic factor-expressing NCSC and/or SCP cells spontaneously transmigrate into decellularized extracellular matrix and integrate well with the aligned matrix structure. This generates a NGC functionalized with neurotrophic factor-expressing NCSC and/or SCP cells embedded in the wall matrix of the NGC.

In another aspect, the invention provides a method of making neurotrophic factor-expressing NCSC and/or SCP cells, the method comprising providing gingiva-derived mesenchymal stem cells (GMSCs); and culturing the GMSCs in a 3D-collagen hydrogel, thereby making neurotrophic factor-expressing NCSC and/or SCP cells. In various embodiments, providing the GMSCs comprises isolating the GMSCs from gingival tissue. The gingival tissue itself may be obtained by any method known in the art. In various embodiments, the gingival tissue is human gingival tissue.

In various embodiments, the 3D-collagen hydrogel comprises about 3-5 mg/mL collagen in mesenchymal stem cell culture medium. In various embodiments, the 3D-collagen hydrogel comprises 4 mg/mL collagen in mesenchymal stem cell culture medium. A person of skill in the art is able to devise a suitable medium for culturing mesenchymal stem cells. All such medium is contemplated for use in the various aspects and embodiments of the invention. In various embodiments, the mesenchymal stem cell medium comprises alpha-Minimum Essential Medium (α-MEM) and Fetal Bovine Serum (FBS). In various embodiments, the 3D-collagen hydrogel is methacrylated. Tunable methacrylated Type I collagen (commercially available; in various embodiments from ADVANCED BIOMATRIX®) was utilized to encapsulate GMSCs. The methacrylated Type I collagen solution was mixed with neutralizing solution and the tested cell suspension in PBS at defined ratios to achieve a final concentration of collagen gel at about 4 mg/mL. Following incubation at 37° C. for 20 min, the solidified Type I collagen encapsulated with specific density of GMSCs was designated as 3D collagen hydrogel. As described above, in various embodiments, the neurotrophic factor-expressing NCSC and/or SCP cells express various markers.

In another aspect, the invention provides a method of making a functionalized nerve guidance conduit, the method comprising providing gingiva-derived mesenchymal stem cells (GMSCs); culturing the GMSCs in a 3D-collagen hydrogel, thereby making neurotrophic factor-expressing NCSC and/or SCP cells; filling a nerve guidance conduit with the neurotrophic factor-expressing NCSC and/or SCP cells; and culturing the nerve guidance conduit in vitro, thereby forming a functionalized nerve guidance conduit. The nerve guidance conduit is functionalized in the sense that the neurotrophic factor-expressing NCSC and/or SCP cells have migrated and become embedded in the wall matrix. Providing mesenchymal stem cells obtained from gingival tissue (GMSCs) and culturing the GMSCs in a 3D-collagen hydrogel are described above. Likewise, the various markers expressed by the neurotrophic factor-expressing NCSC and/or SCP cells are also described above. In various embodiments the NGC is specifically generated for this purpose. In various embodiments the NGC to be functionalized is a commercially available NGC. In various embodiments, the NGC is an AXOGUARD® NGC. In various embodiments the NGC is an Acellular allogeneic nerve graft (ANGs) by way of non-limiting example an Avance® Nerve Graft, a semi-permeable type 1 collagen NGC by way of non-limiting example a NeuraGen® Nerve Guide, a porcine type I & III collagen NGC by way of non-limiting example Orthod Revolnerv®, a Type I collagen NGC by way of non-limiting example Neuroflex®, Neuromatrix®, or Neuromend®, a Chitosan NGC by way of non-limiting example Reaxon® Nerve Guide, porcine small intestine submucosa (SIS) by way of non-limiting example AxoGuard® Nerve Connector, a Polyvinyl alcohol (PVA) NGC by way of non-limiting example Salutunnel™, a Polyglycolic Acid (PLA) NGC by way of non-limiting example Neurotube®, a polycaprolactone (PCL) NGC by way of non-limiting example Neurolac®, or a porcine urinary bladder matrix (UBM) by way of non-limiting example Gentrix® Surgical Matrix Plus. In various embodiments the NGC is an AxoGuard® Nerve Connector or a Gentrix® Surgical Matrix Plus.

In another aspect, the invention provides a method of making a functionalized nerve protector (NP). Functionalized nerve protectors were generated using a method similar to that used making the functionalized nerve guidance conduit. For example, methacrylated collagen hydrogel encapsulated with GMSCs is filled into customized nerve protectors (NPs) made of for example, porcine small intestine submucosal extracellular matrix (SIS ECM) (and incubated at 37° C. for 20 min, followed by continuously culturing in complete α-MEM medium for about 24 h).

In another aspect, the invention provides a method of treating a nerve injury in a subject in need thereof, the method comprising implanting the functionalized nerve guidance conduit or NPs according to various aspects and embodiments of the invention at a site of nerve injury in the subject, thereby treating the nerve injury. In various embodiments, the nerve injury is a peripheral nerve injury.

In various embodiments, in vivo, implantation of functionalized NGCs laden with GMSC-derived NCSC/SCP-like cells described herein (designated as GiSCs), significantly improved the functional recovery and axonal regeneration in a segmental facial nerve defect model in rats.

In various embodiments, in vivo, implantation of functionalized NPs laden with GMSC-derived Schwann-like cells (NP/GiSCs) facilitated functional recovery and axonal regeneration at the crush-injured site of rat sciatic nerves

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples, therefore, specifically point out the preferred embodiments of the present invention, and are not to be construed as limiting in any way the remainder of the disclosure.

The materials and methods employed in these experiments are now described.

Animals

Female Sprague-Dawley rats aged 6-8 weeks old (weighing 200-250 g) were purchased from Charles River Laboratories. Rats were group-housed in polycarbonate cages in the animal facilities with controlled temperature (23° C.±2° C.), 40-65% of humidity and a 12-hour light/dark cycle, fed with a standard laboratory diet and allowed ad libitum access to drinking water.

Cell Culture

Gingival tissues were obtained as remnants of discarded tissues from healthy human subjects aged from 20-40 years old, who underwent a dental procedure following informed consents. Primary GMSCs were isolated, cultured and ex vivo expanded in complete alpha-minimum essential medium (α-MEM) supplemented with 1% L-glutamine, 10% FBS (Zen Bio) and 1% penicillin/streptomycin at 37° C. with 5% $CO_2$ as previously described by us[26]. Human bone marrow-derived mesenchymal stem cells (hBMSCs) were derived from bone marrow aspirations from healthy donors and cultured in complete alpha-minimum essential medium (α-MEM) supplemented with 1% L-glutamine, 10% FBS (Zen Bio), and 1% penicillin/streptomycin at 37° C. with 5% $CO_2$. Cells less than 6 passages were used for experiments.

Culture of GMSCs in 3D Collagen Hydrogel

According to a preliminary screening conducted herein, a purified methacrylated Type I bovine collagen (>98%) was used as the scaffold in the following experiments because of the following unique properties of this commercially available product from Advanced Biomatrix, Inc. (Carlsbad, CA): 1) The collagen is produced from telo-peptide intact bovine collagen and modified by reacting the free amines, primarily the ε-amine groups of the lysine residues as well as the α-amine groups on the N-termini, whereby approximately 40% of the total lysine residues of the collagen molecule have been methacrylated; 2) It can be easily prepared to form native-like 3D scaffolds with varying degree of stiffness by simply altering collagen concentrations; 3) Collagen methacrylate is both thermo-reversible and photo-cross-linkable, being used as a rapidly self-assembling type I collagen to form cross-linked hydrogels for various tissue engineering applications, including in 3D bioprinting.

3D collagen hydrogel was prepared according to the manufacturer's instructions. Briefly, 100 mg of the lyophilized methacrylated type I bovine collagen was dissolved in 16.7 mL of 20 mM acetic acid and mixed on a shaker at 2-10° C. until fully solubilized to make a stock gel solution at a concentration of 6 mg/mL. Then, the required volume of chilled neutralization solution (NS) was added into the calculated volume of the chilled collagen stock solution (85 μl NS: 1 mL collagen) and mixed quickly and thoroughly by pipetting. Afterwards, GMSCs resuspended in a calculated volume of chilled PBS were added into the collagen mixture and mixed quickly and thoroughly by pipetting to achieve a final collagen concentration at 4 mg/mL and a cell density at $2 \times 10^6$/mL. Then, the collagen mixture encapsulated with GMSCs was dispensed in the desired culture plates and incubated at 37° C. for 20 minutes for gel formation followed by culturing in complete α-MEM medium for different time periods. Afterwards, the constructs were harvested and cryosections were prepared for further immunofluorescence studies. Under certain conditions, the 2D plastic 4-well chambered cell culture slides (Nunc® Lab-Tek® Chamber Slide™ system; Cat. #: C6932; Sigma) were pre-coated with 4 mg/mL methacrylated collagen hydrogel. Then, GMSCs were seeded on the top surface of the solidified hydrogel and cultured under the same condition for 48 h. To recover cells from 3D-collagen hydrogels, the cell-laden scaffolds following culture for 48 h were digested with collagenase I (2 mg/mL) at 37° C. on a shaker for 30 minutes. Single cells were collected for further analysis.

Osteogenic Differentiation

GMSCs from 2D-cultures or recovered from 3D-collagen hydrogel were plated at $5 \times 10^5$ cells/well in 6-well plates in MSC growth medium, allowed to adhere overnight, and replaced with osteogenic induction medium supplemented with dexamethasone, L-glutamine, ascorbic acid, and β-glycerophosphate. 4-5 weeks later, the in vitro mineralization was assayed by Alizarin Red S (Sigma-Aldrich) staining and quantified by an acetic acid extraction method.

Adipogenic Differentiation

GMSCs from 2D-cultures or recovered from 3D-collagen hydrogel were plated at $5\times10^5$ cells/well in 6-well plates in MSC growth medium, allowed to adhere overnight, and replaced with adipogenic induction medium supplemented with 10 μM human insulin, 1 μM dexamethasone, 200 μM indomethacin, and 0.5 mM 3-isobutyl-1-methylxanthine (Sigma-Aldrich). Two weeks later, intracellular lipid vacuoles characteristic of adipocytes was determined by Oil Red O staining and the dye content was quantified by isopropanol method.

Calcein-AM Staining

Nerve guidance conduits (NGC) filled with GMSC-laden 3D collagen gels (2, 4, or 6 mg/ml) at a cell density of $2\times10^6$/mL) were cultured in complete α-MEM for 24 h. Before harvesting, Calcein-AM (Cat. #564061; BD Pharmingen) was added into the culture at a final concentration of 1 μM and incubated with at 37° C. for 30 minutes. Cryosections of the NGC constructs were cut, and the signal of Calcein-AM staining was observed under a fluorescence microscope.

RNA Extraction, Library Construction and RNA-Seq

RNA was extracted from the samples according to the instruction manual of the TRIzol reagent (Invitrogen, Carlsbad, Calif.). RNA concentration and purity was measured using a NanoDrop 2000 Spectrophotometer. RNA integrity was assessed using the RNA Nano 6000 Assay Kit of the Agilent Bioanalyzer 2100 system (Agilent Technologies, CA, USA). High-quality RNA was sent to LongseeMed Corporation (Guangzhou, China) for cDNA libraries construction and sequencing run on the Illumina Xten. mRNA was purified by the interaction of the poly (A) tails and magnetic oligo (dT) beads. RNA sequencing libraries were generated using the NEBNext, Ultra RNA Library Prep Kit for Illumina (New England Biolabs, Ipswich, Mass., U.S.A.) with multiplexing primers, according to the manufacturer protocol. The cDNA library was constructed with average inserts of 300 bp (250~300 bp), with non-stranded library preparation. The cDNA was purified using AMPure XP Beads (Beckman Coulter, Inc.). The short cDNA fragments were subjected to end repair, adapter ligation. Then, the suitable fragments were selected by Agen court AMPure XP beads (Beckman Coulter, Inc.) and enriched by PCR amplification.

Data Analysis for RNA-Seq

Base quality value and base distribution of raw data were detected to control quality of initial RNA-seq data by Fastp. In the trimming process, the sequencing adapters, 3 leading and 3 trailing bases were first trimmed. The reads were then scanned from both ends, using a 4 bp-wide sliding window, within which the low quality (lower than Q30) bases were trimmed. Finally, the resulting reads of length at least 50 bases were selected for further analysis. The read alignment is done using HISAT2 v.2.0.5 software with Ensembl GRCh38 genome as reference genome. Transcripts Assembly is done using StringTie v.1.3.3b software. Significant DE genes or transcripts (q-value <0.05) were extracted by edgeR (R package) for each comparison groups. Differentially expressed genes (DEGs) were analyzed with gene ontology enrichment analysis and KEGG by R software with cluster Profiler package. Significant GO or KEGG terms (FDR-value <0.05) were extracted using hypergeometric distribution. DAVID Gene Functional Classification Tool (david.ncifcrf.gov/) was employed to identify the biological functions of the genes related to neural crest stem cells, MSC property and secretome, and Notch signaling pathways.

Quantitative Real-Time Polymerase Chain Reaction (qRT-PCR)

Total RNA was extracted using the Trizol reagent (Invitrogen) and RNA concentration and purity was measured using a NanoDrop 2000 Spectrophotometer. The first strand cDNA was synthesized using the High-Capacity cDNA Reverse Transcription Kits (Applied Biosystems). The quantitative real-time PCR (qRT-PCR) was performed using cDNA as the template in a 20 μl reaction mixture containing FastStart SYBR Green Master (Qiagen), and a specific pair of primers of each cDNA on Bio-Rad CFX96 Touch Real-Time PCR Detection System. The amplification steps included denaturation at 95° C. for 15 min, followed by 40 cycles of denaturation at 94° C. for 15 s, annealing at 55° C. for 30 s, and extension at 72° C. for 30 s. Data were obtained from three independent samples. The relative gene expression was quantified using the delta-delta Ct method ($^{\Delta\Delta}CT$) with the expression of Gapdh as an internal control. The relative fold-change in a specific gene of interest from the control was calculated using the $2^{-\Delta\Delta ct}$ method.

Natural Nerve Conduits Laden with Schwann-Like Cells Reprogrammed from GMSCs in 3D Collagen Hydrogel Collagen hydrogel (40 μl) at a final concentration of 4 mg/ml encapsulated with GMSCs ($2\times10^6$/mL) was filled into the commercially available AxoGuard Nerve protector or connector (customized with 2 mm in internal diameter×10 mm length) made of porcine small intestine submucosal extracellular matrix (SIS-ECM) (Cook Biotech) and incubated at 37° C. for 20 min for gel formation followed by culturing in complete α-MEM medium for 24 h. Afterwards, the constructs were used for further in vivo studies.

Immunofluorescence Studies i. Cryosections prepared from 3D-collagen gel or GMSC-seeded nerve conduits were blocked and permeabilized for 1 h at room temperature in PBS with 2.5% goat serum and 0.5% Triton X-100, followed by incubation with the following primary antibodies at the appropriate dilution overnight at 4° C.: p75 (mouse IgG, 1:200, Sigma), SOX-9 (rabbit IgG, 1:200, Cell Signal Tech), SOX-10 (mouse IgG, 1:200, R & D), S-100β (rabbit IgG, 1:200, Boster Biological Tech), NOTCH3 (rabbit IgG, 1:200, Abcam), HES1 (rabbit IgG, 1:200, Cell Signaling Tech), vinculin (mouse IgG, 1:400, Millipore), TRITC-conjugated phalloidin (1:400, Millipore), BDNF (rabbit IgG, 1:200, Abcam), GDNF (rabbit IgG, 1:200, Abcam), or NGF (rabbit IgG, 1:200, Abcam). After washing with PBS, cells were incubated with appropriate secondary antibodies at room temperature for 1 h: goat anti-rabbit IgG-AlexaFluo-488 (1:300, BioLegend). Isotype-matched control antibodies (BioLegend) were used as negative controls. Nuclei were counterstained with 4', 6-diamidino-2-phenylindole (DAPI). Images were captured using Olympus inverted fluorescence microscope (IX73). For semi-quantitative analysis, at least six randomly selected regions of interesting (ROI) were visualized and the integrated immunofluorescence intensity was measured using Olypus cellSens™ imaging software.

ii. Cryosections (10 μm thickness) prepared from the 3D-collagen hydrogel encapsulated with GMSCs were permeabilized in 0.5% Triton X-100 for 20 min and blocked with 2.5% goat serum in PBS at room temperature for 1 h. Then, the sections were incubated with the following primary antibodies at 4° C. overnight: S-100β (M00979-1; rabbit monoclonal IgG, 1:200; Boster, Pleasanton, Calif.), p75 (AHP1014; rabbit IgG, 1:200; BioRad), BDNF (ab108319; rabbit IgG, 1:200; Abcam), and GDNF (ab18956; rabbit IgG, 1:200; Abcam). Following washing twice with PBS, sections were incubated with Alexa FluorR 488 Donkey anti-rabbit IgG (minimal x-reactivity) antibody (406,416; 1:300, BioLegend) at room temperature for 1 h, while an isotype-matched control antibody, FITC Donkey anti-rabbit IgG (minimal x-reactivity) antibody (BioLegend), was used as a negative control. Nuclei were counterstained with 4',6-diamidino-2-phenylindole (DAPI). Images were captured using Olympus inverted fluorescence microscope (IX73). For semiquantitative analysis, cells with positive signals in at least six random high-power fields (HPF) were visualized, counted, and expressed as the percentage of total DAPI-positive cells.

Western Blot

Cells cultured in the 3D-collagen gel were recovered following enzymatic dissociation with collagenase 1 (2 mg/mL) and whole cell lysates were prepared by incubation with radioimmunoprecipitation (RIPA) assay buffer (Santa Cruz) supplemented with a cocktail of protease inhibitors (Santa Cruz) and the total protein concentrations were determined using bicinchoninic acid (BCA) method (Bio-Vision). Then 30 μg of proteins were subjected to SDS-polyacrylamide gel electrophoresis before being electroblotted onto a 0.2 μm nitrocellulose membrane (GE Healthcare). After blocking with 5% nonfat dry milk in TBST [25 mmol/L Tris (pH, 7.4), 137 mmol/L NaCl, 0.5% Tween20], membranes were incubated at 4° C. overnight with following primary antibodies: p75 (1:1000, Cell Signaling), NOCTH3 (1:1000, Abcam), HES1 (1:1000, Cell Signaling). GAPDH (1;2000, Cell Signaling) was used as a loading control. After extensively washing, membranes were incubated with horseradish peroxidase (HRP)-conjugated secondary antibodies (Santa Cruz) and blot signals were developed with ECL™ Western Blotting Detect Reagents (GE Health Care). All blots were derived from the same experiment and processed in parallel. Uncropped Western blotting images are provided in FIG. 16 with the size markers labeled.

Flow Cytometry 2D-cultured GMSCs or GMSCs recovered from 3D-collagen gels via digestion with collagenase I were immunostained with specific antibodies for human CD90, CD44, CD73 (1:200, BioLegend) or p75 (1:200, Sigma) or an isotype control, followed by incubation with Alexa Fluor 488-conjugated secondary antibodies. The cell samples were analyzed by BD FACSCalibur Flow Cytometer. Data were processed and analyzed by FlowJo software.

Surgical Procedures of Facial Nerve Transection

Transected facial nerve defects were created in adult Sprague-Dawley rats. Briefly, a 6-mm gap was made in buccal branch of the facial nerve and the proximal and distal stumps were bridged by an 8-mm long nerve autograft, empty nerve guidance conduit (NGC) or NGC laden with GMSC-derived NCSC/SCP-like cells (NGC/GiSC). Two 8-0 Ethilon interrupted sutures were applied at each side of the gap to stabilize the grafts. To block the signal to the whisker pad, a 6-mm defect was created in the marginal mandibular branch and ligated with 8/0 Ethilon interrupted sutures.

Facial Functional Analysis Using the Facial Palsy Score

Facial palsy scores were blindly evaluated from animals in different treatment groups at every week until the termination of the study. The facial palsy score was valued based on the following functional evaluation: 1) Symmetry of the vibrissae at rest (0, asymmetry; 0.5, slightly; 1, normal); 2) Motion of the vibrissae (0, no motion; 1, minor trembling;

2, effective movement; 3, normal); 3) Symmetry of the nose at rest (0, asymmetry; 0.5, slightly; 1, normal); 4) Motion of the nose (0, asymmetry; 1, slightly; 2, normal). A maximum seven-point indicates a normal midface without facial palsy, while a zero-point indicate complete facial palsy of the midface.

Electrophysiological Analysis i. Electrophysiological analysis was performed at 14-weeks post transection of facial nerves of rats. At the terminal time point, the nerve was transcutaneously stimulated using a monopolar stimulating electrode positioned proximal or distal to the repair site. Compound muscle action potential (CMAP) recordings were obtained following stimulation from the active monopolar electrode placed in the muscle belly of the vibrisal muscles and reference electrode in the corresponding tendon. A train of 5 pulses were averaged to reduce background noise. The peak-to-baseline CMAP amplitude and latency were measured, and the nerve conduction velocity (NCV) was calculated using the onset latency and distance relative to the recording electrode for the two stimulation sites. CMAP latency was measured as the initial depolarization from the baseline after the stimulus artifact. To calculate percent recovery, CMAP values were normalized to the contralateral side.

ii. Electrophysiological analysis was performed at 4 weeks post-crush injury of sciatic nerves of rats. Bipolar stimulating electrodes were placed percutaneously either proximal or distal to the sciatic nerve injury, and a subdermal recording electrode was placed in the tibialis anterior muscle with a reference electrode placed in the tendon. After determining the initial threshold for an evoked muscle response, the supramaximal compound muscle action potential (CMAP) was obtained by doubling the current until the waveform plateaued and then averaged over a train of 5 pulses (0-5 mV; 100×gain; 10-10,000 Hz bandpass and 60 Hz notch filters; Natus Viking EDX). CMAP amplitude and the time latency following proximal or distal stimulation were measured. Motor nerve conduction velocity (NCV) was calculated based on the difference in latency and distance between the two different stimulation points across the crush injury site of the sciatic nerve. CMAP latency was estimated as the time between the stimulus artifact and the first depolarization at the start of the CMAP. CMAP percent recovery was calculated by normalizing the ipsilateral response to the contralateral, uninjured side.

Immunohistochemical Studies i. The facial nerves were harvested 14 weeks post-injury and implantation of nerve conduits. The tissue samples were fixed in 4% PFA for 24 h and cryoprotected in 10%, 20%, and 30% sucrose and embedded in O.C.T. and 10 μm-thick cryostat sections were cut. After blocking and permeabilization in PBS containing 2.5% goat serum and 0.5% Triton X-100 at room temperature for 1 h, the sections were incubated with primary antibodies for S-100β (1:200) and neurofilament (1:200) overnight at 4° C., followed by incubation with fluorescein-conjugated secondary antibodies for 1 h at room temperature. Isotype-matched control antibodies (BioLegend) were used as negative controls. Nuclei were counterstained with DAPI. The images were captured under a fluorescence microscope and the integrated immunofluorescence intensity for both NFL and S-100β in six randomly selected regions of interesting (ROI) was quantified using Olympus cellSens™ imaging software.

ii. The gastrocnemius muscles of both hindlimbs were harvested and weighed at 4 weeks post-injury and implantation of nerve protectors. The dissected nerve tissue samples were fixed in 4% PFA for 24 h and cryoprotected in 10%, 20%, and 30% sucrose and embedded in O.C.T., and 10-μm-thick cryosections were cut. After permeabilization in 0.5% Triton X-100 for 20 min and blocking with 2.5% goat serum in PBS at room temperature for 1 h, the sections were incubated with primary antibodies at 4° C. overnight: S-100β (M00979-1; rabbit monoclonal IgG, 1:200; Boster), β-tubulin III (MCA2047; mIgG1, 1:200; BioRad), human nuclei (GTX82624; mIgG, 1:200; GenTex), BDNF (ab108319; rabbit IgG, 1:200; Abcam), GDNF (ab18956; rabbit IgG, 1:200; Abcam), active caspase-3 (AB3623; rabbit IgG, 1:200; Millipore), CD68 (MCA341GA; mouse IgG, 1:200; BioRad), arginase-1 (16,001-1-AP; rabbit IgG, 1:200; Proteintech), iNOS (18,985-1-AP; rabbit IgG, 1:200; Proteintech), and CD206 (18,704-1-AP; rabbit IgG, 1:200; Proteintech). After washing twice with PBS, the sections were incubated at room temperature for 1 h with Alexa FluorR 488 Donkey anti-rabbit IgG (minimal x-reactivity) antibody (406,416; 1:300, BioLegend) and Alexa FluorR 588 goat anti-mouse IgG (minimal x-reactivity) antibody (405,326; 1:300, BioLegend), while corresponding isotype-matched control antibodies (BioLegend) were used as negative controls. Nuclei were counterstained with 4',6-diamidino-2-phenylindole (DAPI). Images were captured using an Olympus inverted fluorescence microscope (IX73), and the integrated immunofluorescence intensity for each protein expression in six randomly selected regions of interest (ROI) was quantified using the Olympus cellSens Dimension software. To quantify the expression of S-100β, GDNF, and BDNF in transplanted human GMSCs, the area of colocalized immunolabeling signals) of these proteins and human nuclei in the merged files was measured using ImageJ program and presented as the percentage of colocalization=the area of pixels for colocalized immunolabeling signals/total area of protein pixels. To quantify the apoptosis of transplanted human MSCs, the area of colocalized immunolabeling signals of active caspase-3 (in green color) and human nuclei in the merged files was measured using ImageJ program and presented as the percentage of colocalization=the area of pixels for colocalized immunolabeling signals/total area of pixels of human nuclei.

Morphological Evaluation of Rat Facial Nerves i. The facial nerves were isolated and fixed with 2.5% glutaraldehyde overnight at 4° C., and then post-fixed with 1% osmium tetroxide (OsO$_4$) for 2 h, dehydrated, and embedded in epoxy resin. Semi-thin sections (1-μm) were cut vertically with an ultramicrotome (EM UC7i, Leica Microsystems, Denver, CO), stained with 1% toluidine blue solution, and examined under a light microscope (Olympus IX-73). The density of the myelinated fibers (fibers/1000 μm$^2$) was analyzed from six non-overlapping visual fields per specimen. Ultra-thin sections (60-nm) were stained with lead citrate and uranyl acetate, and then examined under a transmission electron microscope (TEM; JEM-1400; JEOL, Tokyo, Japan). The diameter of myelinated fibers, axons, and the thickness of the myelin sheath were evaluated by cellSens Dimension software (Olympus) and the G-ratio was calculated as the ratio of the inner axonal diameter to the total outer diameter of the fiber.

ii. Morphological Evaluation of Rat Sciatic Nerves

The dissected sciatic nerves were fixed with 2.5% glutaraldehyde overnight at 4° C. and postfixed with 1% osmium tetroxide (OsO4) for 2 h, dehydrated, and embedded in epoxy resin. Semi-thin sections (1 μm) were cut vertically with an ultramicrotome (EM UC7i, Leica Microsystems, Denver, CO, www.leica-microsystems.com) and stained with 1% toluidine blue solution, and images were captured under a light microscope (Olympus IX-73). The density of the myelinated fibers (fibers/1000 μm2) was analyzed from six non-overlapping visual fields per specimen. On the other hand, ultrathin sections (60 nm) were stained with lead citrate and uranyl acetate, and images were captured under a transmission electron microscope (TEM, JEM-1400). All these services were provided by the Electron Microscopy Resource Lab of Perelman School of Medicine at UPenn. The diameter of myelinated fibers, axons, and the thickness of the myelin sheath was evaluated by cellSens Dimension software (Olympus), and the G-ratio was calculated as the ratio of the inner axonal diameter to the total outer diameter of the fiber.

Co-Culture of GMSCs and THP-1 Macrophages

THP-1 cells were seeded into a 6-well culture plate (1×106/well), followed by treatment with 100 nM phorbol 12-myristate 13-acetate (PMA; Sigma) in RPMI-1640 culture media for 6 h to induce differentiation of THP-1 cells into M0 macrophages. Then, the media was removed, and cells were washed twice with PBS. Following resting for 24 h in serum-free RPMI-1640, differentiated THP-1 macrophages were indirectly co-cultured with 5×105 of GMSCs at a cell ratio of 1:2 (GMSC/THP-1 cells) that were seeded onto the top cell insert with 1-μm-sized pores (Fisher Scientific). Otherwise, GMSCs (5×105) encapsulated in the 3D-collagen hydrogel (4 mg/mL) at a final cell density of 2×106/mL were directly placed into a 6-well culture plate containing differentiated THP-1 macrophages (1×106/well). Cells were continuously cultured in complete RPMI-1640 culture media for 48 h, followed by stimulation with 100 ng/mL of lipopolysaccharide (LPS) for 3 h. Then, the conditioned culture media were harvested for ELISA on the secretion of IL-10, IL-1β, and TNF-α. Under certain conditions, THP-1 cells were co-cultured with GMSCs for 24 h followed by stimulation with 100 ng/mL of LPS for 24 h to induce M1 macrophages. For all experiments, GMSCs and THP-1 macrophages cultured alone served as controls.

Enzyme-Linked Immunosorbent Assay (ELISA)

The secretion level of IL-10, IL-1β, and TNF-α in the supernatants of co-cultured cells was detected using the ELISA MAX™ Deluxe Sets according to the manufacturer's protocols (BioLegend; San Diego, CA).

Generation of a Functionalized Nerve Protector Laden with GMSC-Derived Schwann-Like Cells Functionalized nerve protectors were generated according to the established procedures as described previously. Briefly, about 40 μl of methacrylated collagen hydrogel (4 mg/mL) encapsulated with GMSCs (2×106/mL) was filled into customized nerve protectors (NPs) (2 mm in internal diameter×10 mm length) made of porcine small intestine submucosal extracellular matrix (SISECM) (Cook Biotech, West Lafayette, IN) and incubated at 37° C. for 20 min, followed by continuously culturing in complete α-MEM medium for 24 h.

Crush Injury of Rat Sciatic Nerves and Implantation of Functionalized Nerve Protector Rats were anesthetized by intraperitoneal injection of a mixture of ketamine/xylazine (100/10 mg/kg body weight). An incision was made from the right sciatic notch to the distal thigh, and the subcutaneous tissue was bluntly dissected to expose the bicep femoris muscle. The sciatic nerve was exposed and crushed at a point 5 mm distal to the sciatic notch with a type 5 watchmaker forceps for 30 s as previously described. Then, the empty or functionalized NPs (10 mm in length) laden with GiSCs were wrapped around the injury site, while rats with crush injuries alone served as the control. Four weeks following nerve injury and implantation of nerve protectors, the animals were killed and the sciatic nerves were harvested for further analysis.

Rat Sciatic Functional Index (SFI) Analysis

At 4 weeks post-injury and implantation of nerve conduits, rats with hind paws dipped in black ink were guided to walk across a narrow track, and footprints were recorded on white paper. Afterward, the following parameters on both the normal (N) and the experimental (E) hind legs were measured: print length (PL), the distance from the heel to the toe; toe spread (TS), the distance from the first to the fifth toes; and intermediary toe spread (ITS), the distance from the second to the fourth toes. SFI was calculated according to the following formula: $SFI = -38.3 \times (EPL-NPL)/NPL + 109.5 \times (ETS-NTS)/NTS + 13.3 \times (EITS-NITS)/NITS - 8.8$. The SFI varies from 0 to −100: scores at about 0 represent a normal nerve function, while scores at about −100 represent a complete loss of function.

Statistical Analysis i. Quantifications were performed from at least three independent experiments (biological replicates or donors) for cell studies in vitro and from three to six animals for in vivo experiments. Unpaired two-tailed Student's t-test and one-way analysis of variance (ANOVA) with the Tukey's post test were performed for pairwise and multi-group comparisons, respectively. Data were represented as mean±SD and a P value of less than 0.05 ($p<0.05$) was considered statistically significant. All analyses were performed with Excel data analysis or SPSS Statistics version 18.0 (IBM, Inc., Armonk, NY, USA).

ii. All data were expressed as mean±standard error of measurement (SEM), and all statistical analyses were carried out using SPSS Statistics version 18.0 (IBM, Inc., Armonk, NY, USA). Direct comparisons between experimental and control groups were analyzed by paired Student's t test. One-way analysis of variance (ANOVA) was employed for multiple comparisons. Post hoc pairwise comparison between individual groups was performed using Tukey's test. A P value of less than 0.05 was considered statistically significant.

Example 1: 3D-Collagen Hydrogel Drives the Conversion of GMSCs into NCSC/SCP-Like Cells Human gingiva-derived mesenchymal stem cells (GMSCs) were routinely isolated and characterized by the expression of several MSC-associated cell surface markers, e.g. CD44, CD73, and CD90, but negative for hematopoietic cell markers, e.g. CD45 (FIGS. 9A and 9B), as well as their multipotent differentiation capacities into adipocytes (FIGS. 9C and 9D) and osteocytes (FIGS. 9E and 9F).

Figures 1A, 1B, 1C, 1D:
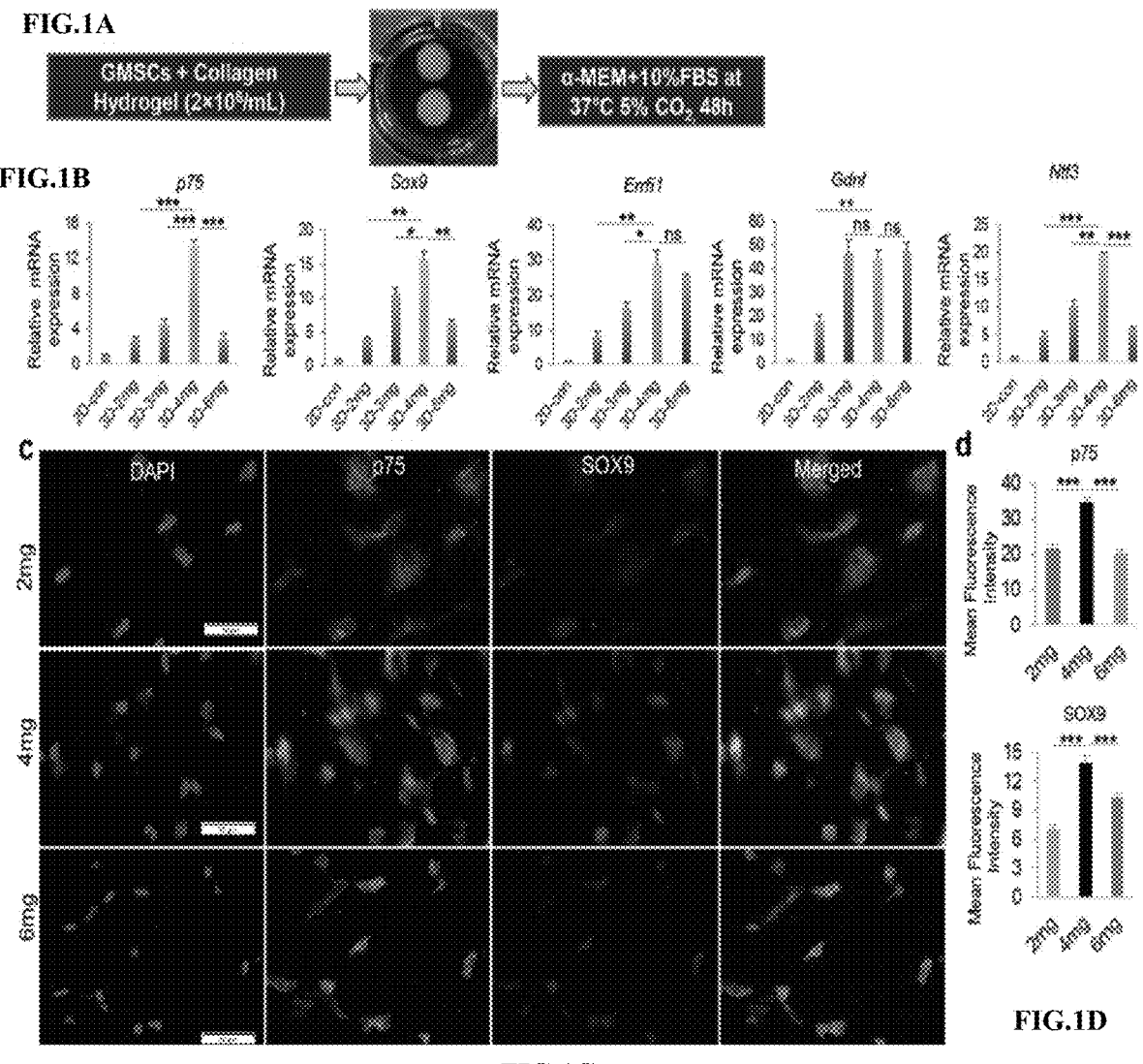
FIGS. 1A-1D show upregulation of NCSC/SCP-related genes in gingiva-derived mesenchymal stem cells (GMSCs) cultured in methacrylated 3D-collagen hydrogel.

Several lines of evidence have shown that the physical properties of the 3D-scaffolds or substrate, e.g. its porosity and stiffness (a combined single parameter known as matrix density) can mechanically influence phenotypic conversion or differentiation of stem cells toward a special cell lineage. Herein, GMSCs were initially cultured for 48 h in methacrylated 3D-collagen hydrogel with different matrix densities or stiffness achieved by varying collagen concentrations (2, 3, 4, 6 mg/mL) with regular MSC culture medium (α-MEM+10% FBS) (FIG. 1A), and then mRNA expression of NCSC/SCP-related genes was determined by qRTPCR. Unexpectedly, the results obtained herein showed that GMSCs cultured in collagen gel at 4 mg/mL had the largest increase in expression of $p75^{NTR}$, Sox9, ERBB Receptor Feedback Inhibitor 1 (Errfi1), and glial cell-derived neurotrophic factor (Gdnf) as compared to those in 2D-cultured GMSCs (FIG. 1b). An optimal increase in the protein expression of $p75^{NTR}$ (NGFR) and SOX9, two common NCSC/SCP-related genes, was confirmed in GMSCs cultured in 3D collagen hydrogel at a concentration of 4 mg/mL (FIGS. 1C,1D). Based on these findings, collagen hydrogel with a concentration of 4 mg/mL was selected as the optimal matrix density for all the subsequent studies. The increased expression of $p75^{NTR}$ protein in GMSCs cultured in 3D-collagen hydrogel at 4 mg/mL was further confirmed by IF staining (FIGS. 2A,2B). Flow cytometric analysis indicated that about 80% of 3D-cultured GMSCs are positive for $p75^{NTR}$ compared to 7.6% in 2D-cultured GMSCs (FIGS. 2C,2D). Western blot showed that the expression of $p75^{NTR}$ protein started to increase at day 1 in GMSCs after cultured in 3D collagen hydrogel, which was maintained up to day 5 (FIGS. 2E,2F). Of note, when 2D plastic culture dishes were pre-coated with 4 mg/mL methacrylated collagen hydrogel and then GMSCs were seeded onto the surface of the solidified hydrogel (FIG. 10A) and cultured for 48 h, cells exhibited a more elongated morphology than those encapsulated in the hydrogel (FIG. 10B). Meanwhile, GMSCs seeded on top of the hydrogel didn't show an increased expression of $p75^{NTR}$ (FIG. 10C). In addition, the results obtained herein indicated that human bone marrow-derived mesenchymal stem cells (hBMSCs), as characterized by the expression of MSC-associated cell surface markers (FIG. 11A) and adipogenic/osteogenic differentiation potentials (FIG. 11B), didn't show an increased expression of $p75^{NTR}$ and SOX9 when encapsulated in the methacrylated 3D-collagen hydrogel and cultured under the same culture conditions as GMSCs (FIG. 11C). These results demonstrate that GMSCs encapsulated in methacrylated 3D-collagen hydrogel with an optimal stiffness could be converted toward a NCSC/SCP-like phenotype.

Example 2: Gene Expression Profiling by the Next-Generation RNA-Sea

To further characterize the phenotypic changes in GMSCs cultured under 3D-collagen hydrogel, next-generation RNA-sequencing was performed to profile the gene expression patterns in GMSCs cultured under 2D-monolayer and 3D-collagen hydrogel conditions, whereby significant differentially expressed genes (DEGs) were defined as those with a log 2 fold change (FC)≥1 (GMSC-3D v.s. GMSC-2D) and a false discovery rate (FDR) of ≤1%. A total of 5588 DEGs, including 3476 upregulated and 2112 downregulated genes were identified from GMSCs cultured in the 3D collagen hydrogel compared to 2D-cultured GMSCs (FIG. 12A). Hierarchical cluster analysis revealed a different hierarchical clustering algorithm in 3D- and 2D-cultured GMSCs as illustrated in the heatmap (FIG. 12B). These findings demonstrate that GMSCs cultured in 3D-collagen hydrogel underwent significant transcriptome changes as compared with those under regular 2D-culture conditions.

Figures 3A, 3B:
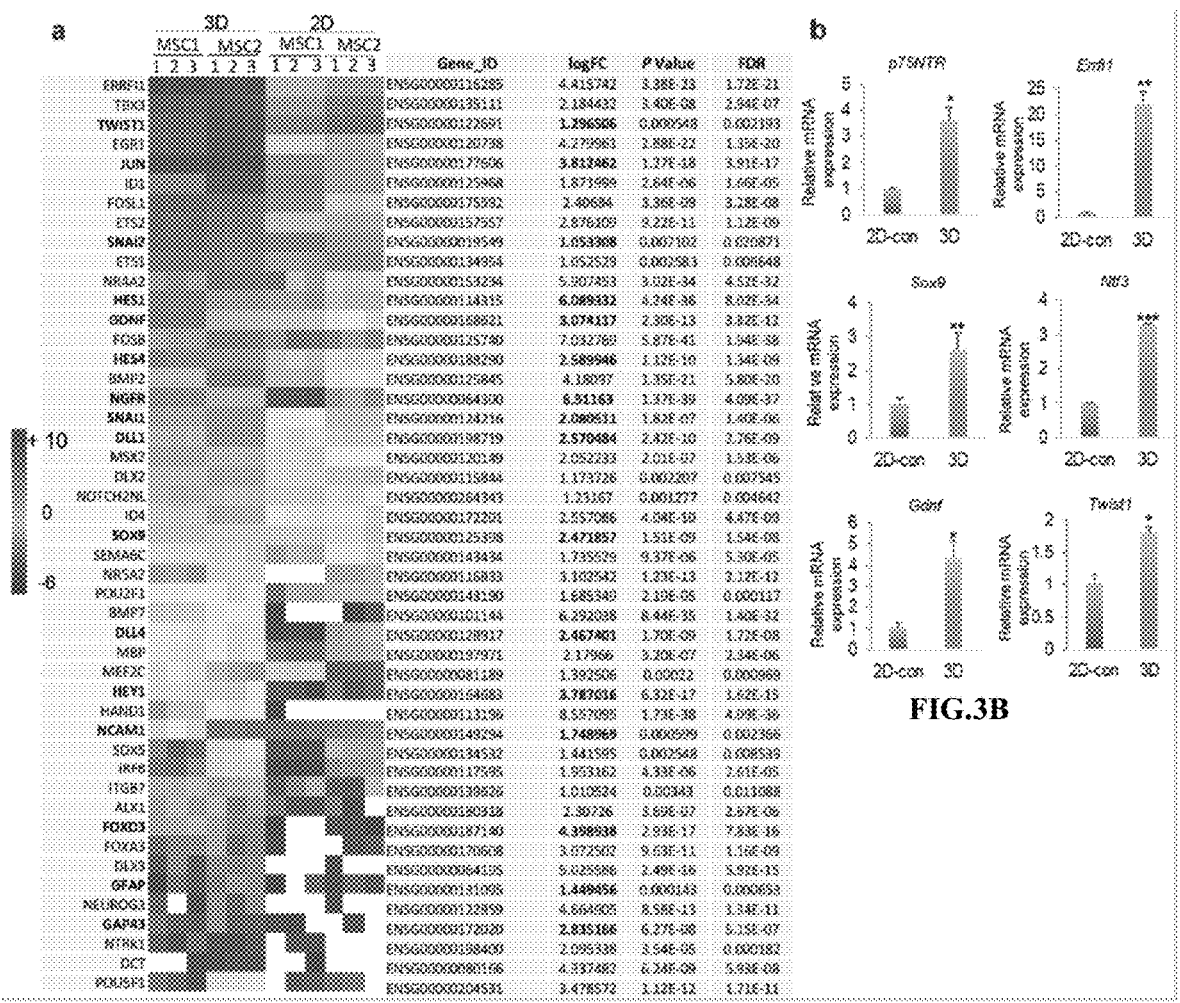
FIGS. 3A-3B show RNA-seq on the expression profile of neural crest and Schwann cell precursor cell-related genes in GMSCs cultured in methacrylated 3D-collagen hydrogel. GMSCs were encapsulated in 3D-collagenhydrogel (4 mg/mL) at a cell density of 2×10$^6$/mL and cultured in complete α-MEM for 48 h. Total RNA was extracted from 2D- and 3D-cultured GMSCs for next generation RNA-seq or qRT-PCR.

Example 3: Gene Functional Annotation/Classification of DEGs in GMSCs Cultured in 3D-Collagen Hydrogel Through DAVID Gene Functional Annotation/Classification of those significantly upregulated DEGs in 3D-cultured GMSCs, 47 genes related to specification and function of NCSC and/or SCPs were identified (FIG. 3A), which include cell surface markers such as NGFR ($p75^{NTR}$), growth factors such as GDNF, transcription factors such as TBX3, TWIST, JUN, SNAI2 (Slug), SNAIL1, ETS1, ETS2, ID1, and SOX9, and Notch signaling (FIG. 3A). Among these upregulated genes, the mRNA expression levels of several genes, including p75$^{NTR}$, Sox9, Errfi1, Gdnf Ntf3, and Twist1, were further confirmed by qRT-PCR (FIG. 3B).

Figures 4A, 4B, 4C, 4D, 4E:
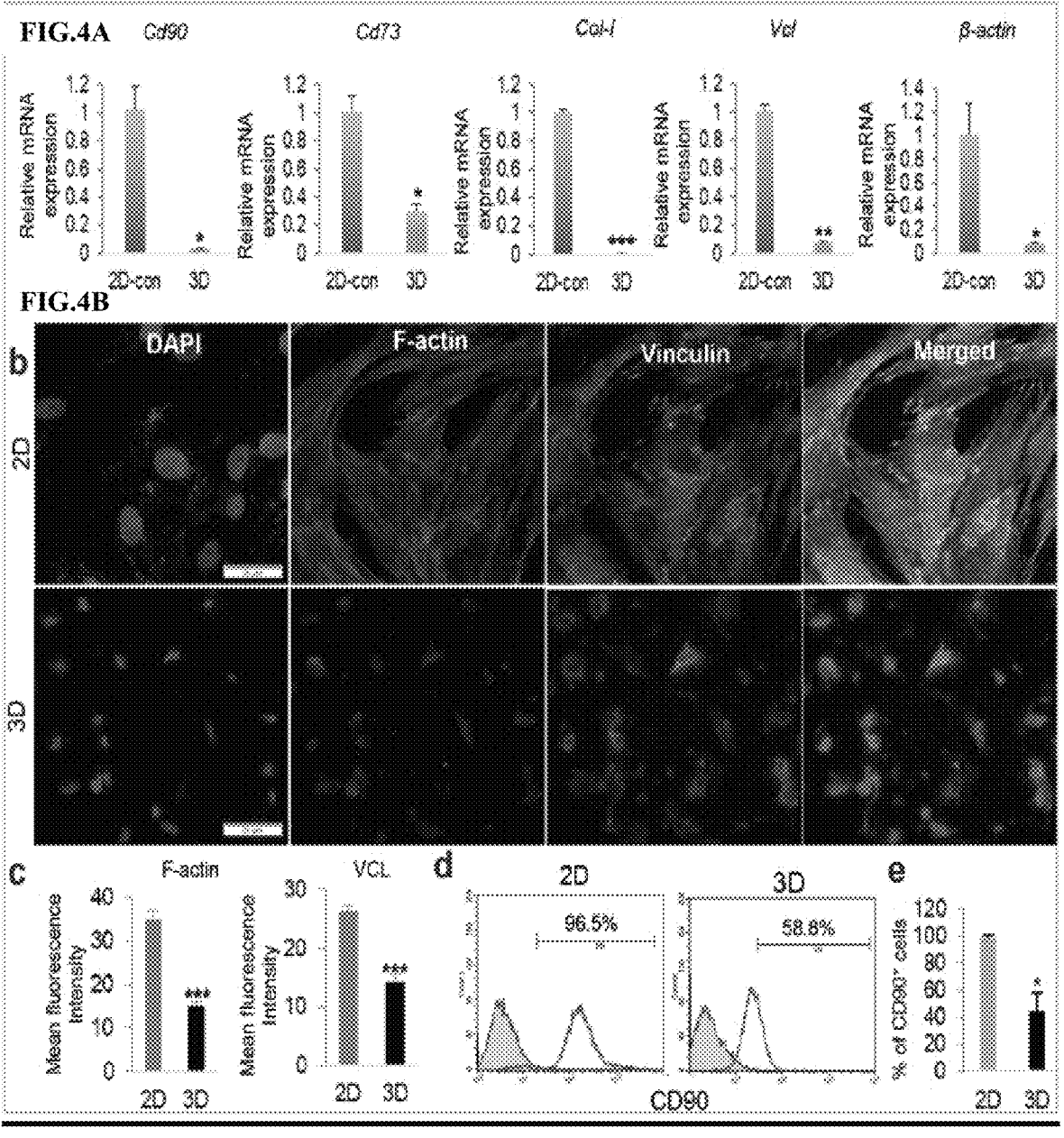
FIGS. 4A-4E show downregulation of mesenchymal cell-associated marker genes in GMSCs cultured in methacrylated 3D-collagen hydrogel.

MSCs were characterized by the expression of a panel of mesenchymal markers such as CD73, CD90, and type I collagen. Previous studies indicated that MSCs showed decreased expression of cell adhesion molecules, e.g. vinculin, and cytoskeletal proteins, e.g. F-actin, when cultured in soft substrate, and that GMSCs gradually reduced the expression of MSC-associated cell surface markers during nongenetic induction into NCSC-like cells. The results described herein indicated that GMSCs cultured in 3D-collagen hydrogel showed a significant decrease in the mRNA expression of mesenchymal genes, such as type I collagen (ColI), vinculin (VCL), β-actin, Cd90, and Cd73, as determined by qRT-PCR (FIG. 4$a$). Meanwhile, GMSCs cultured in 3D-collagen hydrogel underwent morphological changes including reduced cell volume, nuclear size, and relaxation of cytoskeleton (FIG. 4B). The decreased expression of VCL and F-actin at the protein level was further confirmed by immunofluorescence staining (FIG. 4B, FIG. FIG. 4C), while the decreased protein expression of CD90 in GMSCs cultured in 3D-collagen hydrogel was confirmed by flow cytometric analysis (FIG. 4D, FIG. 4E). Of note, the results obtained herein indicated that GMSCs recovered from 3D-collagen hydrogel lost their multipotent differentiation capacities into adipocytes (FIGS. 9C and 9D) and osteocytes (FIGS. 9E and 9F). Taken together, these findings further support that GMSCs cultured in 3D collagen hydrogel lost their mesenchymal properties.

Example 4: Upregulation of NOTCH3 Signaling Pathway in GMSCs Cultured in 3D-Collagen Hydrogel Due to the critical role of Notch signaling pathways in neural crest cell (NCC) fate determination and peripheral gliogenesis during development and differentiation of human pluripotent stem cells, as well as in dedifferentiation of myelinating Schwann cells into a repair phenotype, whether Notch signaling was upregulated in GMSCs cultured in 3D-collagen hydrogel was next tested. Through DAVID Gene Functional Annotation/Classification of those significantly upregulated DEGs in 3D-cultured GMSCs, 19 Notch signaling components were identified, including Notch ligands (DLL1, DLL4, and Jagged 2), Notch3 receptor, and canonical NOTCH-downstream transcription factors (Hes1, Hes4, Hes7, and Hey1) (FIG. 5A). The log 2(FC) for Dll1, Dll4, Jag2, Hes4, and Notch3 is ~2.5 for each gene, equals to ~5-fold change over those in 2D-GMSCs. The log 2(FC) for Hey1, Hes7, and Hes1 are 3.8, 4.8, and 6.1, respectively, which are equal to 13.8-, 27.3-, and 68.1-fold changes over 2D-cultured GMSCs, respectively (FIG. 5A). The upregulation of several major Notch signaling components at the mRNA level, e.g. Notch3, Jag2, Dll1, Dll4, Hes1, and Hey1, was further confirmed by qRT-PCR (FIG. 5B). Meanwhile, the increased expression of NOTCH3 and HES1 at the protein level was confirmed by IF staining (FIGS. 6A-6C) and Western blot (FIGS. 6D-6E), respectively. In addition, the presence of different concentrations of (2S)—N-[(3,5-Difluorophenyl) acetyl]-L-alanyl-2-phenyl] glycine 1,1-dimethylethyl ester (DAPT), a specific NOTCH inhibitor, robustly abrogated the upregulated mRNA expression of p75$^{NTR}$, Gdnf, and Errfi1 genes in GMSCs in cultured 3D-collagen hydrogel (FIG. 6F). Meanwhile, blocking NOTCH activity significantly abrogated the increased secretion of GDNF and NTF3 in GMSCs cultured in 3D-collagen hydrogel (FIGS. 6G-6H). These compelling results demonstrate that the activation of NOTCH signaling pathway may play an important role in 3D collagen hydrogel-driven conversion of GMSCs into NCSC/SCP-like cells.

Example 5: Harnessing 3D Collagen Hydrogel-Directed Conversion of GMSCs into NCSC/SCP-Like Cells to Generate Functionalized Nerve Guidance Conduits The neural crest stem/progenitor cells not only possess multipotent stem cell-like characteristics such as selfrenewal but also have potent migratory capacity. Whether this unique property could be harnessed to automatically generate functionalized nerve conduits (NGC) laden with GMSC-derived NCSC/SCP-like cells (GiSCs) directed by 3D-collagen hydrogel was next tested. To this end, GMSCs encapsulated in various 3D-collagen hydrogels with different concentrations (2, 4, 6 mg/mL) were filled into nerve connector/protector made of porcine small intestine submucosal extracellular matrix (SIS-ECM) and then cultured with regular MSC medium for 24 h (FIG. 7A). Calcein-AM staining indicated that GMSCs encapsulated in 3D-collagen hydrogel at 4 mg/mL exhibited the maximal transmigration into the wall matrix of the NGC as compared to other two concentrations of hydrogel (FIGS. 7B-7C). The transmigration of GMSCs encapsulated in 3D-collagen hydrogel at 4 mg/mL into the wall matrix of NGCs was further confirmed by the positive expression of human nuclei (FIG. 7D). Meanwhile, GMSCs transmigrated into wall matrix of NGCs positively express glial/Schwann cell-related genes, such as S-100β, GFAP, and SOX10 (FIG. 7D), but also neurotrophic factors, GDNF and BDNF, but not NGF (FIGS. 13A-13C). Taken together, these results demonstrated the feasibility of readily generating functionalized NGCs laden with GiSCs by harnessing the unique behavior and fate of GMSCs directed by 3D-collagen hydrogel.

Example 6: Implantation of Functionalized Nerve Conduits Laden with GiSCs Facilitated Functional Recovery and Axonal Regeneration of Transected Rat Facial Nerves Next, the regenerative potentials of functionalized nerve conduits laden with GiSCs were evaluated in a transected facial nerve defect model in rats. Clinically, longitudinal nerve function assessment indicated that both groups of animals implanted with nerve autografts and NGC/GiSCs showed significantly and comparably improved facial palsy scores as compared to those implanted with empty NGCs (FIG. 8A) (p<0.01). At 14 weeks postsurgery, EMG analysis showed that implantation of nerve autografts and NGC/GiSCs exhibited comparable beneficial effects on the recovery of the compound muscle action potential (CMAP) of the vibrissal muscle and nerve conduction velocity (NCV), both of which were much more pronounced than those implanted with empty NGC (CMAP: AG or GiSC vs eNGC, p<0.01; NCV: AG or GiSC vs eNGC, p<0.05; (FIGS. 8B, 8C). Histologically, expression of Schwann cell and axonal markers, (S-100β and neurofilament, respectively) was significantly elevated in the graft site following repair with an autograft or NGC/GiSCs compared to empty NGC alone (FIGS. 14A-14C). Toluidine blue staining and electron microscopy (EM) analyses showed that the newly regenerated facial nerves from animals implanted with either nerve autografts or NGC/GiSCs harbored well-organized nerve fibers, increased number of myelinated axons, and thicker myelin sheaths than those implanted with empty NGCs (FIGS. 8D-8H). Of note, even following implantation and surgery for 14 weeks, GiSCs survived and were located on the periphery of newly regenerated nerves as identified by the positive immunostaining signals for human nuclei and GDNF (FIG. 15). Accordingly, functionalized nerve conduits laden with GiSCs significantly facilitate axonal regeneration and functional recovery of transected facial nerves of rats.

Example 7

In the present study, it is shown that when cultured in soft 3D methacrylated Type I bovine collagen hydrogel at 4 mg/mL, GMSCs of the NC-origin could be rapidly and consistently converted into NCSC/SCP-like state characterized by increased expression of a panel of NCSC/SCP-related genes and a simultaneous decrease in the expression of MSC-related genes. These findings have demonstrated a novel approach for the efficient generation of NCSC/SCP-like cells by culturing GMSCs in 3D collagen hydrogel with an optimal stiffness. Several masters signaling pathways, such as WNT, Sonic Hedgehog, bone morphogenetic proteins (BMPs), fibroblast growth factor (FGF), transformation growth factor (TGF)-β, and NOTCH signaling, have been identified as major nodes of the regulatory networks that control NC fate determination and different lineage specialization during embryonic development and induction of iPSCs toward NC fate. Meanwhile, several lines of evidence have implicated the critical role of NOTCH signaling in governing the fate determination of NCSCs to glial cell lineages in the developing peripheral nervous system as well as in the conversion of myelinating Schwann cells into a repair phenotype. In the present study, a significant upregulation of a panel of Notch signaling components, particularly, DLL1, DLL4, JAG2, Notch3, Hes1, and Hey1, was identified during 3D collagen hydrogel-directed conversion of NC-derived GMSCs into NCSC/SCP-like state. These findings suggest that the intrinsic Notch signaling pathway imprinted in NC precursors and their derivatives could be harnessed to convert adult NC-derived cells, e.g., GMSCs, toward their precursor state.

To date, there is still lack of efficient therapies that ensure full regeneration and functional recovery of peripheral nerve injury (PNI) due to the limited understanding of the pathophysiology of PNI and mechanisms underlying nerve repair/regeneration. Currently, nerve autografts remain the gold standard for the treatment of injured nerves with a gap, but major short comings such as the limited availability, donor site morbidity, and the suboptimal clinical outcome, have significantly compromised their clinic use. In the last two decades, much progress has been made in fabricating different types of nerve guide conduits (NGCs) as potential alternatives to nerve autografts, including the combinatory use of supportive cells and biological factors, in peripheral nerve repair/regeneration, but large variations exist in the clinical outcomes due to the differences in cell delivering strategies. Herein, it was found that GMSCs encapsulated in 3D collagen hydrogel were converted into NCSC/SCP-like phenotype, which could spontaneously transmigrate into multilayered wall matrix of natural nerve conduits and express neurotrophic factors. Moreover, implantation of functionalized nerve conduits laden with GiSCs significantly facilitated regeneration and functional recovery of transected facial nerves of rats. These findings have demonstrated the feasibility to rapidly generate functionalized NGC by harnessing 3D collagen hydrogel-driven conversion of GMSCs into NCSC/SCP like cells. In conclusion, it is demonstrated that adult NC tissue derived GMSCs encapsulated in 3D-collagen hydrogel could be rapidly converted into NCSC/SCP-like cells, which can spontaneously transmigrate and integrate into the wall matrix of natural nerve conduits made of porcine small intestine submucosal matrix (SIS-ECM), leading to rapid generation of functionalized NGCs with significantly improved therapeutic potentials in peripheral nerve repair/regeneration following implantation in vivo. Therefore, the present study has provided a platform for rapid, reproducible, and efficient fabrication of functionalized NGCs with translational potentials in clinic settings.

Example 8: GMSCs Encapsulated in the 3D-Collagen Hydrogel Retained their Immunomodulatory Effects on Macrophages It is demonstrated that the methacrylated 3D-collagen hydrogel with an optimal stiffness drives the direct conversion of GMSCs into Schwann cell precursor-like cells (designated as GiSCs). Herein, immunofluorescence studies further showed that GMSCs displayed a significant increase in the protein expression of S-100β and p75$^{NTR}$, two common markers for Schwann cell precursors when they were encapsulated and cultured in the methacrylated 3D-collagen hydrogel at a concentration of 4 mg/mL for 48 h compared to their counterparts under 2D-culture conditions (FIGS. 17A-17B). Meanwhile, 3D-cultured GMSCs also had a remarkably increased expression of neurotrophic factors, brain-derived neurotrophic factor (BDNF), and glial cell-derived neurotrophic factor (GDNF), compared with 2D-cultured counterparts (FIGS. 17C-17D). These findings further support that GMSCs encapsulated in the 3D-collagen hydrogel can be directly converted into Schwann-like cells with increased expression of neurotrophic factors.

Example 9: GMSCs Encapsulated in the 3D-Collagen Hydrogel Retained their Immunomodulatory Effects on Macrophages Macrophages play a critical cooperative role with Schwann cells in nerve regeneration after injury. It was shown that GMSCs can potently promote the polarization of pro-regenerative (M2) macrophages while suppressing the activation of pro-inflammatory (M1) macrophages. It was then sought whether Schwann-like cells converted from GMSCs encapsulated in the 3D-collagen hydrogel retained their immunomodulatory effects on macrophages. For this purpose, the methacrylated 3D-collagen hydrogel encapsulated with 5×105 of GMSCs (at a cell density of 2×10$^6$) was directly placed into a 6-well culture plate seeded with THP-1 derived M0 macrophages (1×10$^6$/well) (FIG. 18A). Otherwise, the same number of GMSCs was indirectly co-cultured with 1×10$^6$ of THP-1 derived M0 macrophages (1:2) in a trans-well system as previously described. Following co-culture for 48 h, with GMSCs either in the transwell or encapsulated in the 3D-collagen hydrogel, THP-1 macrophages displayed elongated cellular morphology characteristic of a pro-regenerative M2-like phenotype. Concomitantly, co-culture with GMSCs under two conditions led to a comparable increase in the secretion of IL-10, a signature anti-inflammatory cytokine of pro-regenerative (M2) macrophages, compared with THP-1 macrophages or GMSCs cultured alone (FIG. 18B). Under certain conditions, THP-1 M0 macrophages were co-cultured with GMSCs under two conditions for 48 h and then stimulated with 100 ng/mL of LPS in fresh culture media for 3 h. The results indicated that co-culture with GMSCs in the trans-well or with 3D-GMSCs not only increased IL-10 secretion (FIG. 18C) but also significantly reduced the secretion of TNF-α and IL-1β (FIG. 18D,18E), two common pro-inflammatory cytokines secreted by anti-inflammatory (M1) macrophages. These results suggest that Schwann-like cells converted from GMSCs encapsulated in the 3D-collagen hydrogel retained their potent capability to promote polarization of pro-regenerative (M2) macrophages and suppress the activation of pro-inflammatory (M1) macrophages.

Example 10: The Fate of GMSC-Derived
Schwann-Like Cells Following Transplantation In
Vivo The feasibility to generate functionalized neural guidance conduits by harnessing the 3D collagen hydrogel-directed conversion of GMSCs into Schwann-like cells (GiSCs) was demonstrated earlier. Using the same approach, herein the successful fabrication of functionalized nerve protectors (NPs) made of porcine small intestine submucosal (SIS) extracellular matrix was confirmed, whereby the decellularized wall matrix of NPs were repopulated with GiSCs as evidenced by the positive expression of S-100β in cells that have transmigrated into the wall matrix. Next, the in vivo fate and behavior of GiSCs repopulating the wall matrix of NPs following implantation to wrap the crush injury site of rat sciatic nerves was observed (FIG. 23A). Four weeks postimplantation, the NPs were not absorbed and then harvested together with the nerves for further analysis (FIG. 23A). This is in consistent with previous studies, whereby SIS nerve guidance conduits (NGCs) stably maintained their shape without collapsing for up to 8 weeks and showed minimal-to-mild resorption by up to 12 weeks following implantation in vivo. Immunofluorescence (IF) studies indicated that those transplanted GMSCs integrated into the wall matrix of NPs and localized in the peripheral areas outside of the injured nerves as recognized by the positive expression of human nuclei, whereas only about 5% of them were positively stained for the active form of caspase-3 (FIG. 23B, 23C), a specific marker for apoptotic cells. In addition, it was noticed that in the neural protector scaffold occupied area, about 80% of those infiltered cells positively expressing the Schwann cell marker S-100β (FIG. 19A), and neurotrophic factors, GDNF and BDNF (FIGS. 19B,C), were co-immunostained with human nuclei (designated as S-100β+huNu+, GDNF+hNu+, and BDNF+hNu+ cells, respectively) (FIG. 19D). Taken together, these findings have demonstrated the high survivability and secretion of neurotrophic factors of GiSCs integrated into the wall matrix of NPs following transplantation into the nerve injury site.

Example 11: Implantation of Functionalized Nerve
Protectors Laden with GMSC-Derived
Schwann-Like Cells Facilitated Functional
Recovery and Axonal Regeneration of
Crush-Injured Rat Sciatic Nerves The therapeutic potentials of the functionalized NP repopulated with GiSCs (NP/GiSC) following implantation to the crush-injured site of rat sciatic nerves (FIG. 23A) was determined. At 4 weeks postinjury and implantation, EMG analysis indicated that implantation of NP/GiSCs and NP alone showed comparable beneficial effects on the recovery of compound muscle action potential (CMAP) with both proximal and distal stimulation (p<0.05 vs injury control) (FIG. 20A). Interestingly, implantation of NP/GiSC showed much better effects on the recovery of motor nerve conduction velocity (p<0.05, NP/GiSC vs NP) or the percentage of conduction velocity than NP alone (p<0.01, NP/GiSC vs NP) (FIG. 20B). Consistently, walking track analysis showed that rats implanted with NP/GiSCs exhibited a significant improvement in the sciatic functional index (SFI) as compared to animals implanted with empty NP alone (p<0.01, NP/GiSC vs NP) (FIG. 20C,20D). In addition, it was observed that an overall loss of gastrocnemius muscle mass in all groups of animals at 4 weeks post-injury (FIG. 20E), and then the ratio of gastrocnemius muscle weight of the injured side to that of the contralateral side was calculated. The results showed that there was no significant difference in the average muscle ratios between the injury and empty NP groups (p>0.05); however, the average muscle ratio of the NP/GiSC group was higher than that of either injury or empty NP groups (p<0.05) (FIG. 20F), suggesting that implantation of NP/GiSC had better effects to prevent atrophy of gastrocnemius muscle than empty NP. Histological examination of longitudinal sections of the injured sciatic nerves indicated that the nerve fibers at the injured sites in both empty NP and NP/GiSC implantation groups displayed a more organized and aligned axonal arrangement as compared with a random pattern of axonal growth presenting in the injury control group (FIG. 24A). IF staining showed a decreased expression of S-100β and β-tubulin III in the injured nerve as compared to the intact normal nerve (p<0.001) (FIGS. 24A-24C). Implantation of empty NP or NP/GiSCs increased the expression of S-100β and β-tubulin III as compared with the injury control (p<0.001, NP/GiSC vs injury; p<0.01, empty NP vs injury), whereby implantation of NP/GiSC exhibited a more pronounced beneficial effect than empty NP (FIGS. 24A-24C). Next, the remyelination of nerve fibers was evaluated by toluidine blue staining and transmission electron microscopy (TEM) (FIGS. 21A,21B). Morphologically, both toluidine blue staining and TEM showed that the control injured nerves revealed poorly regenerated nerves composed of thin, dispersed myelinated and non-myelinated nerve fibers in comparison with the normal control (FIGS. 21A,21B). As expected, crush injury led to a significant decrease in the density of myelinated nerve fibers and the average thickness of myelin sheath as compared to normal nerves (p<0.001), but a relatively higher G-ratio (p<0.01) as compared to the normal control (FIGS. 21C,21E). However, implantation of either empty NP or NP/GiSC significantly increased the density of myelinated nerve fibers as compared with the injury control (p<0.001; NP or NP/GiSC vs injury), whereby NP/GiSC showed relatively better effects than empty NP at the border statistical significance (p=0.064, NP/GiSC vs empty NP) (FIG. 21C). Further analysis showed that the myelin sheaths in empty NP and NP/GiSC groups were significantly thicker than those of the injury control (p<0.05, empty NP vs injury; p<0.001, NP/GiSC vs injury), while the myelin sheaths of NP/GiSC group were even thicker than those of empty NP group (p<0.001, NP/GiSC vs empty NP) (FIGS. 21D, 21E). Taken together, these findings demonstrated the regenerative therapeutic potentials of functionalized NPs laden with GiSCs (NP/GiSC) in the rat sciatic nerve crush injury model.

Example 12: Immunomodulatory Effects of
GMSC-Derived Schwann-Like Cells on
Macrophages in Rat Sciatic Nerves after Crush
Injury It is demonstrated that GMSC-derived Schwann-like cells (GiSCs) possess potent in vitro modulatory functions to promote the polarization of pro-regenerative (M2) macrophages, and concomitantly, inhibit the activation of pro-inflammatory (M1) macrophages, which are comparable to those conferred by their parental GMSC counterparts (FIGS. 18A-18E). Next, the effects of GiSCs on pro-inflammatory (M1)/pro-regenerative (M2) macrophages in the crush-injured sciatic nerves of rats were determined. CD68 is a common marker for total macrophages, while arginase-1 (Arg-1) and inducible nitric oxide synthase (iNOS) are commonly used as signature genes for pro-regenerative (M2) and pro-inflammatory (M1) macrophages, respectively. The infiltration of CD68$^+$iNOS$^+$ pro-inflammatory (M1) and CD68$^+$Arg1$^+$ pro-regenerative (M2) macrophages in the wall matrix of implanted NPs was then observed. The results indicated that there was no obvious difference in the infiltration of total CD68$^+$ macrophages in the wall matrix of empty NPs and that of GiSC-repopulated NPs at week 4 post implantation (p>0.05; FIGS. 22B,22D). However, there were a significant increase in the infiltration of CD68$^+$Arg1$^+$ pro-regenerative (M2) macrophages (p<0.01; FIGS. 22A, 22B) but a decrease in the infiltration of CD68$^+$iNOS$^+$ pro-inflammatory (M1) macrophages (p<0.05; FIGS. 22C, 22D) in the wall matrix of GiSC-repopulated NPs compared to those in empty NPs. In addition, the infiltration of CD68$^+$iNOS$^+$ proinflammatory (M1) and CD68$^+$Arg1$^+$ pro-regenerative (M2) macrophages within the injured nerve tissues was also observed. The results showed that there was no significant difference in the infiltration of total CD68$^+$ macrophages within injured nerve controls compared with those wrapped with empty NPs at week 4 post-implantation (p>0.05; FIGS. 25A-B;26A-B). On the contrary, the infiltration of total CD68$^+$ macrophages was significantly reduced within injured nerves wrapped with GiSC-repopulated NPs compared to that in injured nerve controls or those wrapped with empty NPs (p<0.001; FIGS. 25A-B;26A-B). Additionally, the results indicated that there was a relatively higher infiltration of CD68+Arg1+ pro-regenerative (M2) macrophages (p<0.05; FIGS. 25A-B) but a lower infiltration of CD68$^+$iNOS$^+$ pro-inflammatory (M1) macrophages (p<0.01; FIGS. 26A-B) within the injured nerves wrapped with GiSC-repopulated NPs compared to that in injured nerve controls or those wrapped with empty NPs. Taken together, these findings suggest that GMSC derived Schwann-like cells retained potent capabilities to promote pro-regenerative (M2) macrophage polarization while suppressing pro-inflammatory (M1) macrophage activation in crush-injured sciatic nerves.

Example 13

In summary, Schwann-like cells converted from GMSCs retained potent immunomodulatory functions to promote pro-regenerative (M2) macrophage polarization and suppress pro-inflammatory (M1) macrophage activation. Implantation of functionalized nerve protectors repopulated GMSC-converted Schwann-like cells to accelerate axonal regeneration and functional recovery of crush-injured rat sciatic nerves accompanied by increased infiltration of pro-regenerative (M2) macrophages while a decreased infiltration of pro-inflammatory (M1) macrophages. These findings suggest that Schwann-like cells converted from GMSCs represent a promising source of supportive cells for regenerative therapy of PNI through their dual functions, neurotrophic effects, and immunomodulation of pro-inflammatory (M1)/pro-regenerative (M2) macrophages.

32

ENUMERATED EMBODIMENTS

The following exemplary embodiments are provided, the numbering of which is not to be construed as designating levels of importance:

Embodiment 1 provides a functionalized nerve guidance conduit (NGC) comprising:
a wall matrix comprising a decellularized extracellular matrix; and
neurotrophic factor-expressing neural crest stem-like cells (NCSC) and/or Schwann cell precursor-like (SCP) cells embedded in the wall matrix.

Embodiment 2 provides the functionalized nerve guidance conduit according to embodiment 1, wherein the neurotrophic factor-expressing NCSC and/or SCP cells are generated from gingiva-derived mesenchymal stem cells (GMSCs).

Embodiment 3 provides the functionalized nerve guidance conduit according to embodiment 1 or embodiment 2, wherein the neurotrophic factor-expressing NCSC and/or SCP cells express at least one neurotrophic factor selected from glial cell-derived neurotrophic factor (GDNF) and brain-derived neurotrophic factor (BDNF).

Embodiment 4 provides the functionalized nerve guidance conduit according to any one of embodiments 1-3, wherein the neurotrophic factor-expressing NCSC and/or SCP cells further express at least one marker selected from the group consisting of Low Affinity Nerve Growth Factor Receptor (NGFR), SRY-Box Transcription Factor 9 (Sox9), ERBB Receptor Feedback Inhibitor I (ERRFI1), Neurotrophin 3 (Ntf3), Twist Family BHLH Transcription Factor 1 (Twist 1), S-100β, SRY-Box Transcription Factor 10 (Sox10), and Glial Fibrillary Acidic Protein (GFAP).

Embodiment 5 provides the functionalized nerve guidance conduit according to any one of embodiments 1-4, wherein the neurotrophic factor-expressing NCSC and/or SCP cells further express at least one NOTCH signaling pathway marker selected from the group consisting of DLL1, DLL4, JAG2, Notch3, Hes1, and Hey1.

Embodiment 6 provides the functionalized nerve guidance conduit according to any one of embodiments 1-5, wherein the neurotrophic factor-expressing NCSC and/or SCP cells are generated from GMSCs by culturing the GMSCs in a 3D-collagen hydrogel.

Embodiment 7 provides the functionalized nerve guidance conduit according to embodiment 6, wherein the 3D-collagen hydrogel comprises about 3-5 mg/mL collagen in mesenchymal stem cell culture medium.

Embodiment 8 provides the functionalized nerve guidance conduit according to embodiment 7, wherein the 3D-collagen hydrogel comprises about 4 mg/mL collagen in mesenchymal stem cell culture medium.

Embodiment 9 provides the functionalized nerve guidance conduit according to embodiment 7 or embodiment 8, wherein the mesenchymal stem cell culture medium comprises alpha-Minimum Essential Medium (α-MEM) and Fetal Bovine Serum (FBS).

Embodiment 10 provides the functionalized nerve guidance conduit according to any one of embodiments 6-8, wherein the 3D-collagen hydrogel is methacrylated.

Embodiment 11 provides the functionalized nerve guidance conduit according to any one of embodiments 1-10, wherein the decellularized extracellular matrix comprises a porcine small intestine submucosal extracellular matrix (SIS-ECM).

Embodiment 12 provides a method of making neurotrophic factor-expressing neural crest stem-like cells (NCSC) and/or Schwann cell precursor-like (SCP) cells, the method comprising:

providing gingiva-derived mesenchymal stem cells (GMSCs); and culturing the GMSCs in a 3D-collagen hydrogel, thereby making neurotrophic factor-expressing NCSC and/or SCP cells.

Embodiment 13 provides the method according to embodiment 12, wherein the 3D-collagen hydrogel comprises about 3-5 mg/mL collagen in mesenchymal stem cell culture medium.

Embodiment 14 provides the method according to embodiment 13, wherein the 3D-collagen hydrogel comprises about 4 mg/mL collagen in mesenchymal stem cell culture medium.

Embodiment 15 provides the method according to embodiment 13 or embodiment 14, wherein the mesenchymal stem cell culture medium comprises alpha-Minimum Essential Medium (α-MEM) and Fetal Bovine Serum (FBS).

Embodiment 16 provides the method according to any one of embodiments 12-15, wherein the 3D-collagen hydrogel is methacrylated.

Embodiment 17 provides the method according to any one of embodiments 12-16, wherein the neurotrophic factor-expressing NCSC and/or SCP cells express at least one neurotrophic factor selected from glial cell-derived neurotrophic factor (GDNF) and brain-derived neurotrophic factor (BDNF).

Embodiment 18 provides the method according to any one of embodiments 12-17, wherein the neurotrophic factor-expressing NCSC and/or SCP cells further express at least one marker selected from the group consisting of Low Affinity Nerve Growth Factor Receptor (NGFR), SRY-Box Transcription Factor 9 (Sox9), ERBB Receptor Feedback Inhibitor I (ERRFI1), Neurotrophin 3 (Ntf3), Twist Family BHLH Transcription Factor 1 (Twist 1), S-100β, SRY-Box Transcription Factor 10 (Sox10), and Glial Fibrillary Acidic Protein (GFAP).

Embodiment 19 provides the method according to any one of embodiments 12-18, wherein the neurotrophic factor-expressing NCSC and/or SCP cells further express at least one NOTCH signaling pathway marker selected from the group consisting of DLL1, DLL4, JAG2, Notch3, Hes1, and Hey 1.

Embodiment 20 provides a method of making a functionalized nerve guidance conduit (NGC), the method comprising:

providing gingiva-derived mesenchymal stem cells (GMSCs);

culturing the GMSCs in a 3D-collagen hydrogel, thereby making neurotrophic factor-expressing neural crest stem-like cells (NCSC) and/or Schwann cell precursor-like (SCP) cells;

filling a nerve guidance conduit with the neurotrophic factor-expressing NCSC and/or SCP cells; and culturing the nerve guidance conduit in vitro, thereby forming a functionalized nerve guidance conduit.

Embodiment 21 provides the method according to embodiment 20, wherein the 3D-collagen hydrogel comprises about 3-5 mg/mL collagen in mesenchymal stem cell culture medium.

Embodiment 22 provides the method according to embodiment 21, wherein the 3D-collagen hydrogel comprises about 4 mg/mL collagen in mesenchymal stem cell culture medium.

Embodiment 23 provides the method according to embodiment 21 or embodiment 22, wherein the mesenchymal stem cell culture medium comprises alpha-Minimum Essential Medium (α-MEM) and Fetal Bovine Serum (FBS).

Embodiment 24 provides the method according to any one of embodiments 20-23, wherein the 3D-collagen hydrogel is methacrylated.

Embodiment 25 provides the method according to any one of embodiments 20-24, wherein the decellularized extracellular matrix comprises a porcine small intestine submucosal extracellular matrix (SIS-ECM).

Embodiment 26 provides the method according to any one of embodiments 20-25, wherein the neurotrophic factor-expressing NCSC and/or SCP cells express at least one neurotrophic factor selected from glial cell-derived neurotrophic factor (GDNF) and brain-derived neurotrophic factor (BDNF).

Embodiment 27 provides the method according to any one of embodiments 20-26, wherein the neurotrophic factor-expressing NCSC and/or SCP cells further express at least one marker selected from the group consisting of Low Affinity Nerve Growth Factor Receptor (NGFR), SRY-Box Transcription Factor 9 (Sox9), ERBB Receptor Feedback Inhibitor I (ERRFI1), Neurotrophin 3 (Ntf3), Twist Family BHLH Transcription Factor 1 (Twist 1), S-100β, SRY-Box Transcription Factor 10 (Sox10), and Glial Fibrillary Acidic Protein (GFAP).

Embodiment 28 provides the method according to any one of embodiments 20-27, wherein the neurotrophic factor-expressing NCSC and/or SCP cells further express at least one NOTCH signaling pathway marker selected from the group consisting of DLL1, DLL4, JAG2, Notch3, Hes1, and Hey 1.

Embodiment 29 provides a method of treating a nerve injury in a subject in need thereof, the method comprising implanting the functionalized nerve guidance conduit according to any one of embodiments 1-11 or 20-28 at a site of nerve injury in the subject, thereby treating the nerve injury.

Embodiment 30 provides the method according to embodiment 29, wherein the nerve injury is a peripheral nerve injury.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A functionalized nerve guidance conduit (NGC) comprising:

a decellularized extracellular matrix; and neurotrophic factor (NTF)-expressing cells generated from gingiva-derived mesenchymal stem cells (GMSCs), wherein the NTF-expressing cells are embedded in the decellularized extracellular matrix.

2. The functionalized nerve guidance conduit according to claim 1, wherein the NTF-expressing cells express at least one neurotrophic factor selected from glial cell-derived neurotrophic factor (GDNF) and brain-derived neurotrophic factor (BDNF).

3. The functionalized nerve guidance conduit according to claim 1, wherein the NTF-expressing cells further express at least one marker selected from the group consisting of Low Affinity Nerve Growth Factor Receptor (NGFR), SRY-Box Transcription Factor 9 (Sox9), ERBB Receptor Feedback Inhibitor I (ERRFI1), Neurotrophin 3 (Ntf3), Twist Family BHLH Transcription Factor 1 (Twist 1), S-100β, SRY-Box Transcription Factor 10 (Sox10), p75NTR, and Glial Fibrillary Acidic Protein (GFAP).

4. The functionalized nerve guidance conduit according to claim 1, wherein the NTF-expressing cells |further express at least one NOTCH signaling pathway marker selected from the group consisting of DLL1, DLL4, JAG2, Notch3, Hes1, and Hey1.

5. The functionalized nerve guidance conduit according to claim 1, wherein the NTF-expressing cells are generated from GMSCs by culturing the GMSCs in a 3D-collagen hydrogel.

6. The functionalized nerve guidance conduit according to claim 5, wherein the 3D-collagen hydrogel comprises about 3-5 mg/mL collagen in mesenchymal stem cell culture medium.

7. The functionalized nerve guidance conduit according to claim 6, wherein the 3D-collagen hydrogel comprises about 4 mg/mL collagen in mesenchymal stem cell culture medium.

8. The functionalized nerve guidance conduit according to claim 6, wherein the mesenchymal stem cell culture medium comprises alpha-Minimum Essential Medium (α-MEM) and Fetal Bovine Serum (FBS).

9. The functionalized nerve guidance conduit according to claim 5, wherein the 3D-collagen hydrogel is methacrylated.

10. The functionalized nerve guidance conduit according to claim 1, wherein the decellularized extracellular matrix comprises a porcine small intestine submucosal extracellular matrix (SIS-ECM).

* * * * *